United States Patent
Greaves et al.

(10) Patent No.: US 9,770,398 B2
(45) Date of Patent: Sep. 26, 2017

(54) PH-SENSITIVE COMPOUND, USE, COMPOSITION AND TREATMENT PROCESS USING SAME

(71) Applicant: L'Oreal, Paris (FR)

(72) Inventors: Andrew Greaves, Magny-le-Hongre (FR); Gustavo Luengo, Montévrain (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/350,007

(22) PCT Filed: Oct. 5, 2012

(86) PCT No.: PCT/EP2012/069750
§ 371 (c)(1),
(2) Date: Apr. 4, 2014

(87) PCT Pub. No.: WO2013/050547
PCT Pub. Date: Apr. 11, 2013

(65) Prior Publication Data
US 2014/0316006 A1   Oct. 23, 2014

Related U.S. Application Data

(60) Provisional application No. 61/553,979, filed on Nov. 1, 2011.

(30) Foreign Application Priority Data

Oct. 6, 2011 (FR) .................................. 11 59035

(51) Int. Cl.
| | |
|---|---|
| *A61K 8/46* | (2006.01) |
| *C07C 323/60* | (2006.01) |
| *A61Q 5/00* | (2006.01) |
| *A45D 19/02* | (2006.01) |
| *C07C 323/25* | (2006.01) |

(52) U.S. Cl.
CPC ............. *A61K 8/46* (2013.01); *A45D 19/02* (2013.01); *A61Q 5/00* (2013.01); *A61Q 5/002* (2013.01); *C07C 323/25* (2013.01); *C07C 323/60* (2013.01)

(58) Field of Classification Search
CPC ............................... A61K 8/46; C07C 323/60
See application file for complete search history.

(56) References Cited

U.S. PATENT DOCUMENTS

| 2,723,972 A | 11/1955 | Herrick |
| 2003/0165450 A1 | 9/2003 | Samain |
| 2008/0025940 A1 | 1/2008 | Breton |

FOREIGN PATENT DOCUMENTS

| EP | 1 321 125 A1 | 6/2003 |
| FR | 2 881 427 A1 | 8/2006 |

OTHER PUBLICATIONS

Mathur et al. (J. Label Compd. Radiopharm 2010, 53 580-585).*
Mathur et al. (J. Label Compd. Radiopharm 2011, 54, p. 150-156).*
International Search Report mailed Dec. 7, 2012, issued in corresponding International Application No. PCT/EP2012/069750, filed Oct. 5, 2012, 2 pages.

* cited by examiner

*Primary Examiner* — Robert Havlin
(74) *Attorney, Agent, or Firm* — Christensen O'Connor Johnson Kindness PLLC

(57) ABSTRACT

The subject of the present invention is a compound of formula (I) below, the addition salts thereof, the dimer thereof and also the organic or inorganic acid salts thereof, the optical isomers thereof, the geometric isomers thereof, and the solvates thereof such as hydrates: (I) These compounds are sensitive to pH and of use for the treatment of keratin fibers, such as human keratin fibers and in particular the hair.

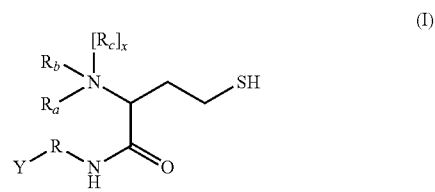

9 Claims, 1 Drawing Sheet

PH-SENSITIVE COMPOUND, USE, COMPOSITION AND TREATMENT PROCESS USING SAME

The subject of the invention is pH-sensitive compounds, which are of use for the treatment of keratin fibres, such as human keratin fibres and in particular the hair. The subject of the invention is also hair compositions comprising one or more pH-sensitive compounds, and also the use of these compounds for treating keratin fibres. Finally, the invention relates to a hair treatment process using said composition, to the use thereof and to kits containing same.

Generally, hair is sensitised, i.e. damaged and/or made brittle to varying degrees by the action of atmospheric agents, in particular by light, and also by the repeated action of various mechanical or chemical treatments, such as, for example, permanent waving, relaxing, dyeing and bleaching of the hair.

These attacks impair the keratin fibre and result in a decrease in the mechanical properties, such as tensile strength, breaking load and elasticity. The physicochemical properties are also impaired. It has been more particularly observed that this damage makes the hair more hydrophilic.

Furthermore, this hair may lose part of the scales, which is reflected by great difficulty in disentangling the head of hair and/or in styling it. The lack of softness of the hair owing to this loss of scales has also been demonstrated ("Chronological ageing of human hair keratin fibres" Int. *J. Cosmet. Science* 32, 422-434 (2010); "A Closer Look at the Complex Hydrophilic/Hydrophobic Interactions Forces at the Human Hair Surface", N. Baghdadli and G. S. Luengo*, *J. of Phys.*: Conf. Ser.s 100, 052034 (2008) and "Adsorption and Lubricating Properties of poly(L-lysine)-graft-poly(ethylene glycol) on Human-Hair Surfaces". *ACS Appl. Mater. Interfaces* 1, 1938-1945 (2009).

Thus, in order to overcome these problems, it has been proposed to use haircare compositions comprising conditioning agents, in particular cationic polymers or silicone compounds. These compositions make it possible to improve the disentangling and the softness of the hair when they are applied. However, these effects disappear rapidly following shampooing. It is therefore necessary to apply these compositions very regularly in order to preserve the benefit, which can lead to certain undesirable effects, such as the head of hair becoming heavy, or a lack of lightness of the hair.

A lack of the smoothness of the hair can also be observed, said hair not being even from the root to the end. Finally, the sheen of the fibres can prove to be insufficient.

These drawbacks are accentuated in the case of fine hair, which lacks liveliness and body. It is therefore found that the current cosmetic compositions containing conditioning agents do not give complete satisfaction regarding disentangling, softness and styling of the sensitised hair.

Document EP 1 321 125 has in particular proposed non-tacky cosmetic hair compositions capable of forming a coating resistant to shampooing, on the hair, thereby making it possible to solve some of the problems mentioned above.

However, it has been observed that the use of such polymers does not make it possible to easily modulate the mechanical and/or chemical properties of the hair.

There is therefore a real need for novel raw materials which make it possible to treat keratin materials, such as human keratin materials and in particular the hair, and which have properties which can be modulated according to prior or subsequent treatments and which withstand external attacks, such as shampooing.

The applicant has discovered that it is possible to remedy these problems by means of compounds of formula (I) below, the addition salts thereof, the solvates thereof and the dimer thereof:

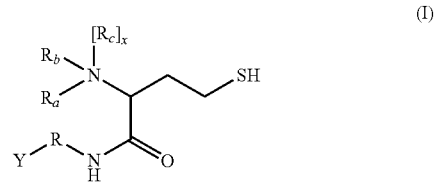

(I)

Figure 1:
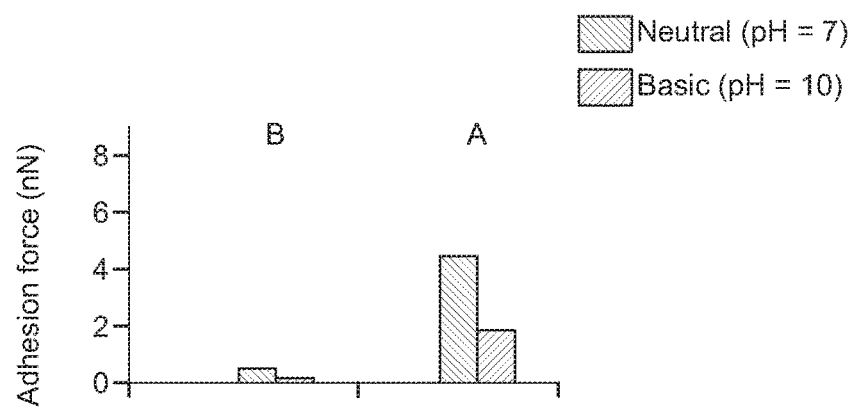
FIG. 1 illustrates results of adhesion force (indication of the hydrophobic nature) on two different types of hair at different pH values: comparative: treated with composition B represented on the left of the graph, and, according to disclosed embodiments: treated with composition A represented on the right of the graph.

The keratin fibres, and in particular the damaged keratin fibres treated with this compound, have good cosmetic properties, such as better mechanical strength and improved disentangling, while at the same time having a long-lasting effect. An increase in the hydrophobic nature of the fibre has in particular been observed.

In particular, the novel compounds and the application process have been designed so as to prevent breaking of the hair. They may quite particularly be intended for repairing and/or reinforcing the hair, especially sensitised hair, and in particular damaged or weakened hair.

One particularly advantageous characteristic is the ability to modulate the hydrophobic nature of the fibre. By modifying the pH of the surface of the fibre, it is possible to modulate the hydrophobic nature of the surface of the fibre and therefore its wettability. The wettability is an important factor in the affinity and the adsorption of other raw materials on keratin fibres, and in particular the hair, such as hair dyes, for example. Furthermore, the possibility of conferring on keratin fibres a hydrophilic nature during shampooing (in order to facilitate cleansing), and then a hydrophobic nature after cleansing (in order to facilitate disentangling) makes it possible to improve the softness and the feel of the fibres.

The subject of the invention is also the use of a compound of formula (II) below:

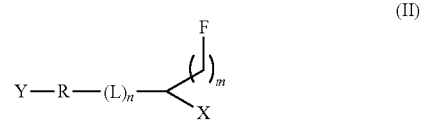

(II)

The subject of the invention is also a composition comprising one or more compounds of formula (II), a process using the composition defined above and the use of said composition for the cosmetic treatment of keratin fibres, such as human keratin fibres and in particular the hair.

Finally, the invention relates to kits containing the composition defined above.

Other characteristics, aspects, subjects and advantages of the present invention will emerge even more clearly on reading the description and the examples that follow.

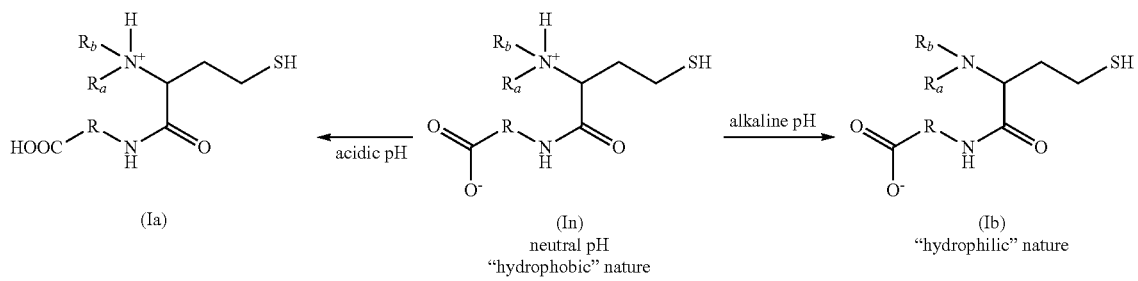

In the text hereinbelow, and unless otherwise indicated, the limits of a range of values are included in that range, in particular in the expressions "between . . . and . . . " and "ranging from . . . to . . . ".

In the text hereinbelow, the term "at least one" is equivalent to "one or more".

Compound of Formula (I)

The subject of the invention is a compound of formula (I) below, the addition salts thereof, the dimer thereof and also the organic or inorganic acid salts thereof, the optical isomers thereof, the geometric isomers thereof, and the solvates thereof such as hydrates:

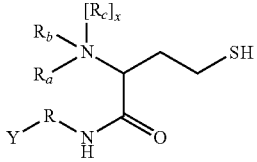

(I)

in which $R_a$, $R_b$ and $R_c$ denote, independently of one another, a hydrogen atom, or a linear or branched $C_1$-$C_4$ alkyl group, preferably a hydrogen atom or a methyl group;

R denotes a linear or branched $C_4$-$C_{18}$ alkylene or alkenylene chain, preferably a linear $C_7$-$C_{18}$ alkylene chain;

x denotes 0 or 1;

when X is 0, the amine is tertiary, then Y denotes an anionic group, preferably Y is chosen from carboxylate, phosphonate, phosphate, sulfate and sulfonate groups;

this entity is in particular present at basic pH, it is anionic;

when x is 1, the amine is quaternary,

Y can denote an anionic group, preferably Y is chosen from carboxylate, phosphonate, phosphate, sulfate and sulfonate groups;

this entity is in particular present at neutral pH, it is zwitterionic;

when x is 1, the amine is quaternary,

Y can also denote a non-ionic group, preferably Y is chosen from carboxylic acid, phosphonic acid, phosphoric acid, sulfonic acid and sulfuric acid groups;

this entity is in particular present at acidic pH, it is cationic;

it being understood that, when the compound of formula (I) contains an anionic or cationic filler, it is combined with one or more cationic or anionic counterions that afford formula (I) electrical neutrality.

The scheme below illustrates the 3 entities covered by formula (I):

For the purpose of the present invention, the term "dimer" is intended to mean the disulfide compound of formula (Id) below:

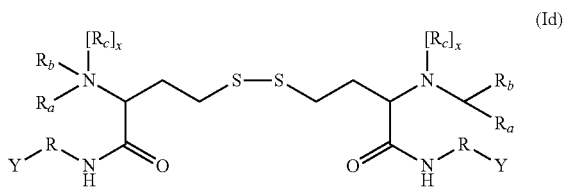

The electrical neutrality of the compounds of formula (I) is provided by an anion or a mixture of anions, denoted $An^-$, which are organic or inorganic and cosmetically acceptable, and a cation or a mixture of cations, denoted $Cat^+$, which are organic or inorganic and cosmetically acceptable.

$An^-$ denotes, for example, a halide such as chloride, bromide, fluoride or iodide; a hydroxide; a sulfate; a hydrogen sulfate; an alkyl sulfate in which the linear or branched alkyl moiety is $C_1$-$C_6$, such as the methylsulfate or ethylsulfate ion; a carbonates; a hydrogen carbonate; a carboxylic acid salt, such as formate, acetate, citrate, tartrate and oxalate; an alkyl sulfonate for which the linear or branched alkyl moiety is $C_1$-$C_6$, such as the methylsulfonate ion; an aryl sulfonate for which the aryl moiety, preferably phenyl, is optionally substituted with one or more $C_1$-$C_4$ alkyl radicals, such as, for example, 4-toluoylsulfonate; an alkyl sulfonate such as mesylate.

$Cat^+$ representing a cation of an alkali metal or alkaline-earth metal (such as sodium, lithium, potassium, calcium or magnesium), organic cations such as ammonium or an ammonium group substituted with one or more identical or different, linear or branched $C_1$-$C_4$ alkyl radicals optionally carrying at least one hydroxyl, such as tetramethylammonium, tetraethylammonium or tetra-n-butylammonium.

The compounds of general formula (I) may be in free form or in the form of salts, such as addition salts with an inorganic acid preferably chosen from hydrochloric acid, hydrobromic acid, sulfuric acid and phosphoric acid or with an organic acid such as, for example, citric acid, succinic acid, tartaric acid, lactic acid, 4-toluoylsulfonic acid, benzenesulfonic acid, acetic acid, para-toluenesulfonic acid, formic acid and methanesulfonic acid.

The compounds of general formula (I) may also be in the form of solvates, for example in the form of a hydrate or of a solvate of a linear or branched $C_1$-$C_6$ alcohol such as ethanol or isopropanol.

This type of particular structure, once applied to the keratin fibres, reacts via the thiol and disulfide functions present at the surface of the fibres, thus forming a covalent bond between the compound of formula (I) or the dimer thereof, and the keratin fibre.

This covalent bond thus allows persistence of the raw material on the hair. It has, moreover, been observed that the raw material is still present on the fibres after several shampooing operations.

It has also been observed that these raw materials produce a notable conditioning effect on the fibre, said effect having the advantage that it can be modulated according to the cosmetic treatments carried out on the head of hair.

First of all, the cosmetic effect can be modulated according to the degree of grafting of the compound of formula (I) onto the keratin fibre. Next, the particular structure of these compounds makes it possible to vary the hydrophobic nature of the keratin fibre according to the pH.

Indeed, the particular structure of the compound of formula (I) makes it possible, according to the pH of the hair composition applied to the hair, to optionally create an ionic bond between the ammonium group and the anionic group Y, when they are present, i.e. in the case of the structure (In). When this ionic bond is present, the structure then has the hydrophobic R chain in the form of a ring, thus conferring on the hair an increase in the hydrophobic nature.

Conversely, when the structure of the compound of formula (I) is in a free form, i.e. without the presence of an ionic bond between the ammonium group and the group Y, in particular in the case of the structure (Ib), the hair thus exhibits an increase in the hydrophilic nature. The group Y is then available for any interaction with the external environment. The pH of the hair composition comprising the compound of formula (I) or else, when the latter is already grafted onto the fibre, the pH of a treatment composition applied to the keratin fibres, will optionally generate the ionic bond between the ammonium group and the anionic group Y. This is why these compounds bear the name pH-sensitive compounds.

Preferably, the compounds of formula (I) are chosen from:

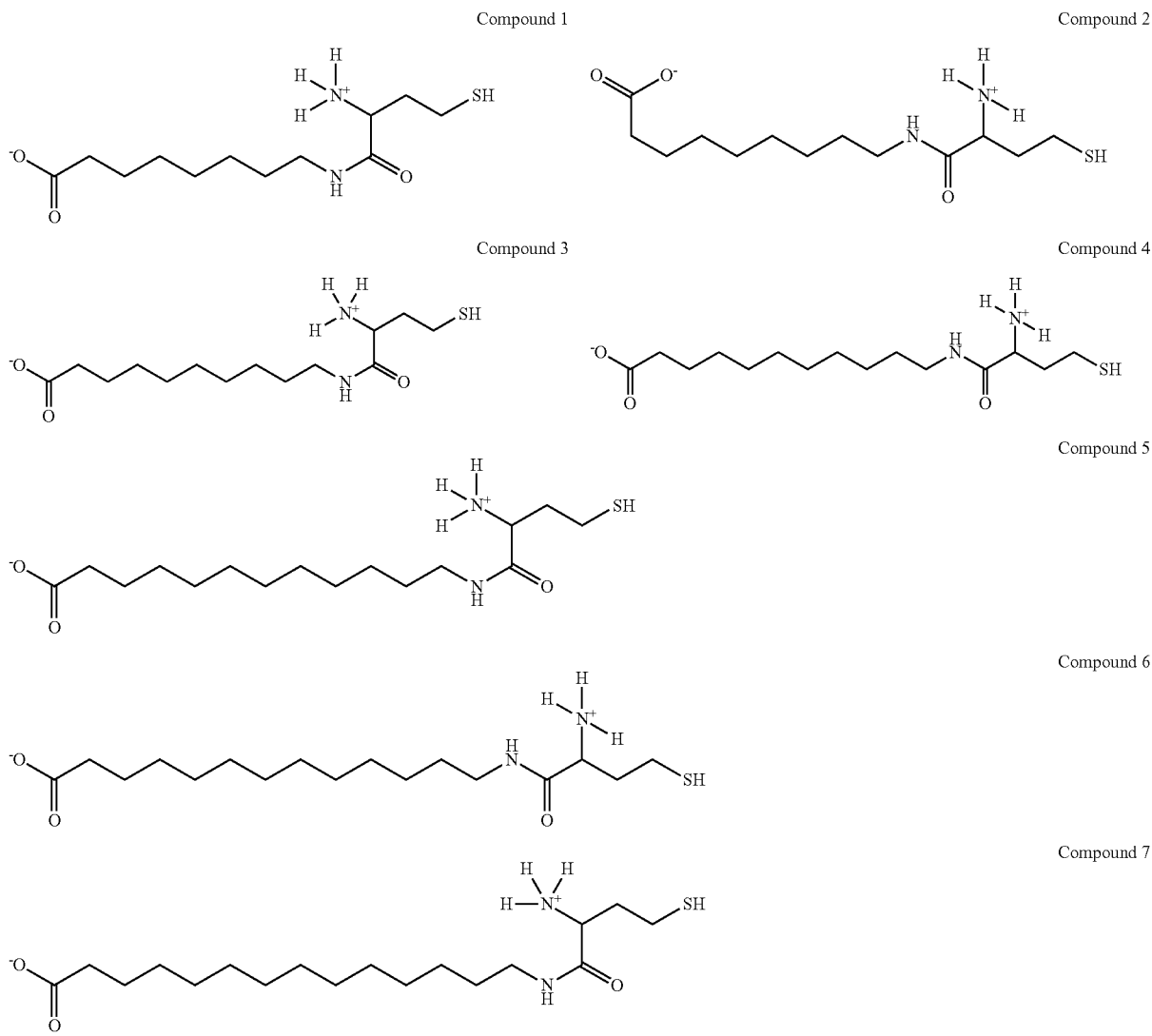

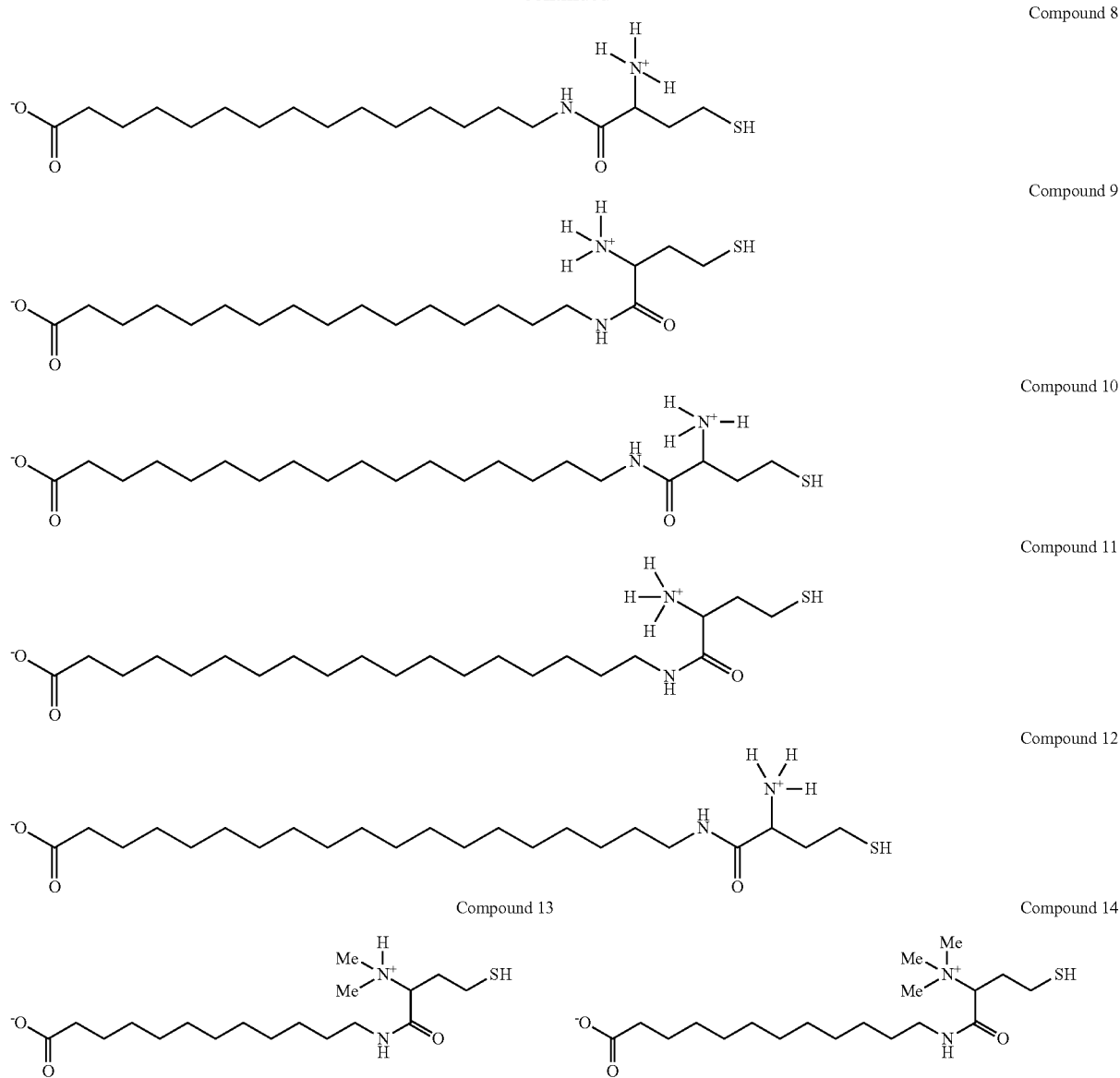

Compound 8
Compound 9
Compound 10
Compound 11
Compound 12
Compound 13
Compound 14

Use of the Compounds of Formula (II)

The subject of the invention is also the use of one or more compounds of formula (II) below, the addition salts thereof, the dimer thereof and also the organic or inorganic acid salts thereof, the optical isomers thereof, the geometric isomers thereof, and the solvates thereof such as hydrates:

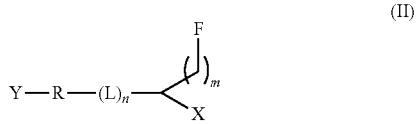

(II)

in which:

F denotes a reactive function chosen from:

thiol, epoxy, anhydride, acid chloride, ethyleneimino, aldehyde, acetal or hemi-acetal, aminal or hemi-aminal, ketone, alpha-haloketone or alpha-hydroxyketone, lactone or thiolactone, isocyanate, thiocyanate, N-hydroxysuccinimide ester, imide, imine, imidate, oxazoline, oxazolinium, oxazine or oxazinium, pyridylthio, thiosulfate, acetoalkylate corresponding to the formula: —OCO-A'-COCH$_3$, A' representing a bond, a linear or branched alkylene group comprising from 1 to 5 carbon atoms, monochlorotriazine, mono fluorochlorotriazine, dichlorotriazine, difluorochloropyrimidine, dichloroquinoxaline, trichloropyrimidine, vinylsulfone as described in document EP1 218 451 A1, vinylamide, active esters, such as succinimidyl esters, sulfosuccinimidyl esters, tetrafluorophenyl esters and sulfodichlorophenol esters, isothiocyanates, sulfonyl chloride, azides, azalactones, nitrenes, catechols, oniums, alkenes, thiolene, ascorbates, diazirines, carbornyl sulfonate, alcoxysilanes, a nitrogen-based heterocycle, as described in document WO2001/025337, hydrated aldehydes, hydrated ketones, or the hydrated form of formic acid, as described in document EP 1 218 454, 1,2-dithiolanes, 1,3-dithiolanes, thiazolines and isothiouroniums, m is 1 or 2

L denotes a carboxamide, ester, alkylamine, thioester, ether, thioether, arylamine, N-acylurea, amidine, urea, urethane, thiourea or sulfonamide function, n is 0 or 1, R has the same meaning as the group R of formula (I) described above, X denotes a group chosen from ammonium, primary amine, secondary amine, tertiary amine, phosphonium, primary phosphine, secondary phosphine and tertiary phosphine groups, and Y denotes a group chosen from carboxylic acid, carboxylate, phosphonic acid, phosphonate, phosphoric acid, phosphate, sulfuric acid, sulfate, sulfonic acid and sulfonate groups, or else X denotes a group chosen from carboxylic acid, carboxylate, phosphonic acid, phosphonate, phosphate, sulfate, sulfonic acid and sulfonate groups, and Y denotes a group chosen from ammonium, primary amine, secondary amine, tertiary amine, phosphonium, primary phosphine, secondary phosphine and tertiary phosphine groups, it being understood that, when the compound of formula (II) contains anionic or cationic fillers, it is combined with one or more cationic or anionic counterions that afford formula (II) electrical neutrality;

for treating keratin fibres, such as human keratin fibres and in particular the hair.

Preferably, the invention relates to the use of the compounds of formula (II) for modulating the hydrophobic nature of keratin fibres, such as human keratin fibres and in particular the hair.

For the purpose of the present invention, the expression "modulating the hydrophobic nature of keratin fibres" is intended to mean varying the strength of the hydrophobic nature of the fibres. The hydrophobic nature is a property that can be measured by several methods, Wilhelmy balance, contact angle or atomic force microscopy (cf. example). If the value measured via the Wilhelmy balance is between −2 and 0 micrograms, the keratin fibres have a hydrophobic nature. If the value measured via the Wilhelmy balance is greater than zero micrograms, the keratin fibres have a hydrophilic nature. The technique for measuring these values is described in the scientific publication Weigmann H. D. and Kamath, Y. K., *Cosmetics & Toiletries*, 101, 37, (1986).

The electrical neutrality of the compounds of formula (II) is provided by an anion or a mixture of anions, denoted $An^-$, which are organic or inorganic and cosmetically acceptable, and a cation or a mixture of cations, denoted $Cat^+$, which are organic or inorganic and cosmetically acceptable. The counterions are identical to those used to provide the electrical neutrality of the compounds of formula (I).

As for the compounds of formula (I), the compounds of general formula (II) may be present in free form or in the form of salts, such as those defined above for the compounds of formula (I). The compounds of general formula (II) may also be in the form of solvates.

For the purpose of the present invention, the term "ammonium group" is intended to mean an ammonium of the type $-N^+R_aR_bR_c$, $R_a$, $R_b$, $R_c$ which may be identical different, representing a hydrogen atom, or a $C_1$-$C_6$ alkyl radical which can be substituted with a hydroxyl. $R_a$ and $R_b$ can together form a heterocycle comprising 5 to 8 ring members, the radical $R_c$ then being a $C_1$-$C_6$ alkyl radical which can be substituted with a hydroxyl.

For the purpose of the present invention, the term "dimer" is intended to mean the compound of formula (IId) below:

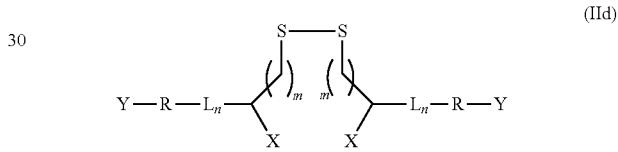

Preferably, the compounds of formula (II) are chosen from the abovementioned compounds 1 to 14 and the following compounds:

Compound 15

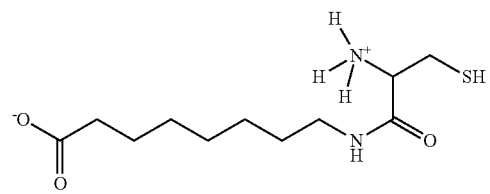

Compound 16

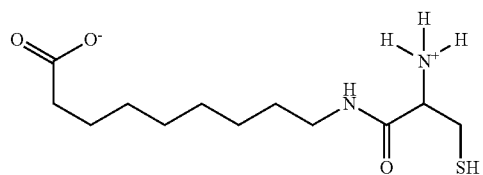

Compound 17

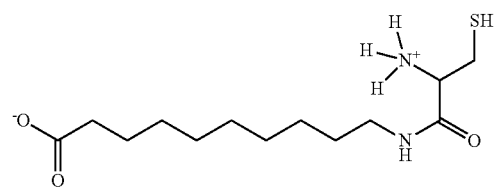

Compound 18

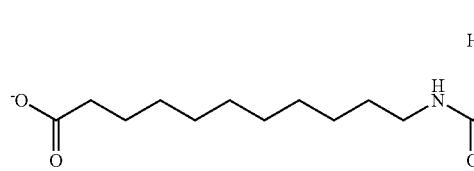

Compound 19

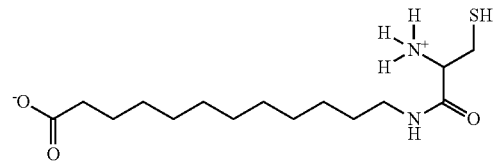

Compound 20

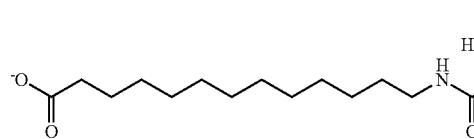

-continued
Compound 21
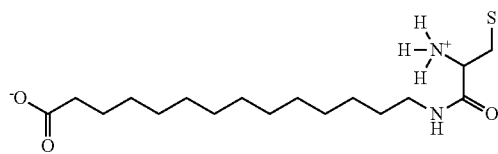
Compound 22
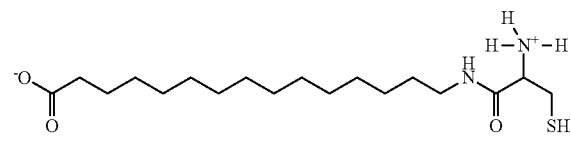
Compound 23
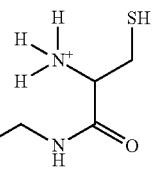
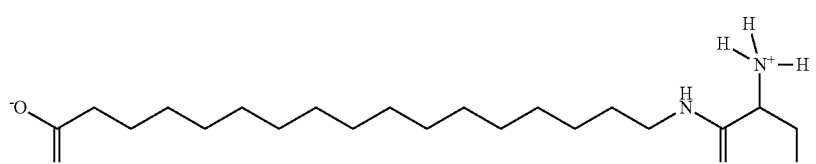
Compound 24
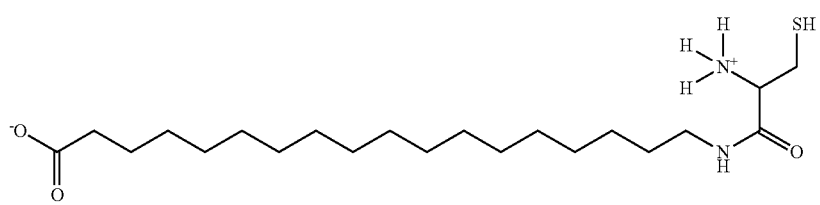
Compound 25
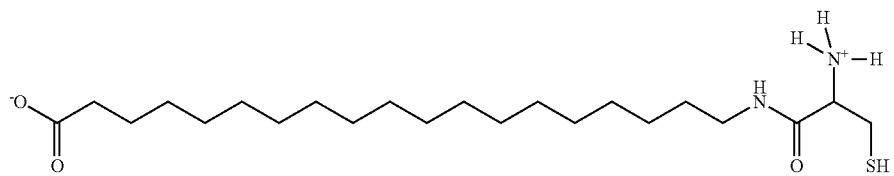
Compound 26
Compound 27
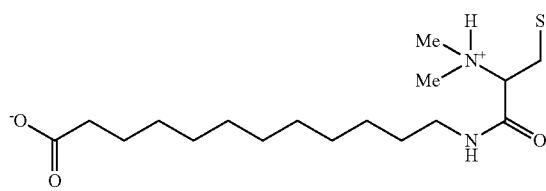
Compound 28
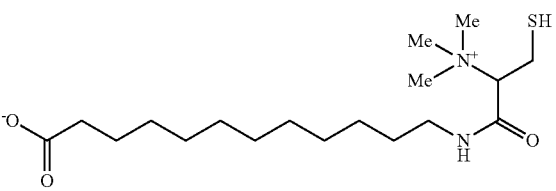
Compound 29
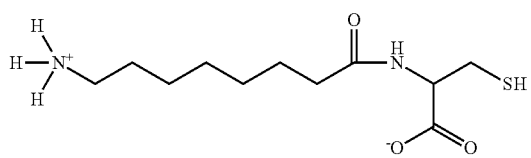
Compound 30
Compound 31
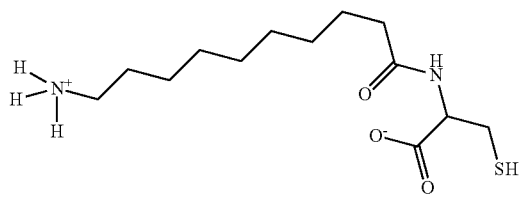
Compound 32
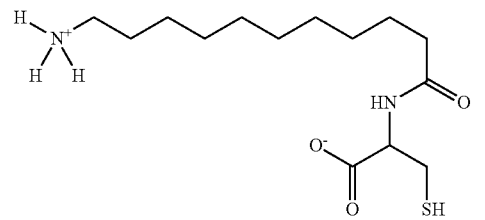

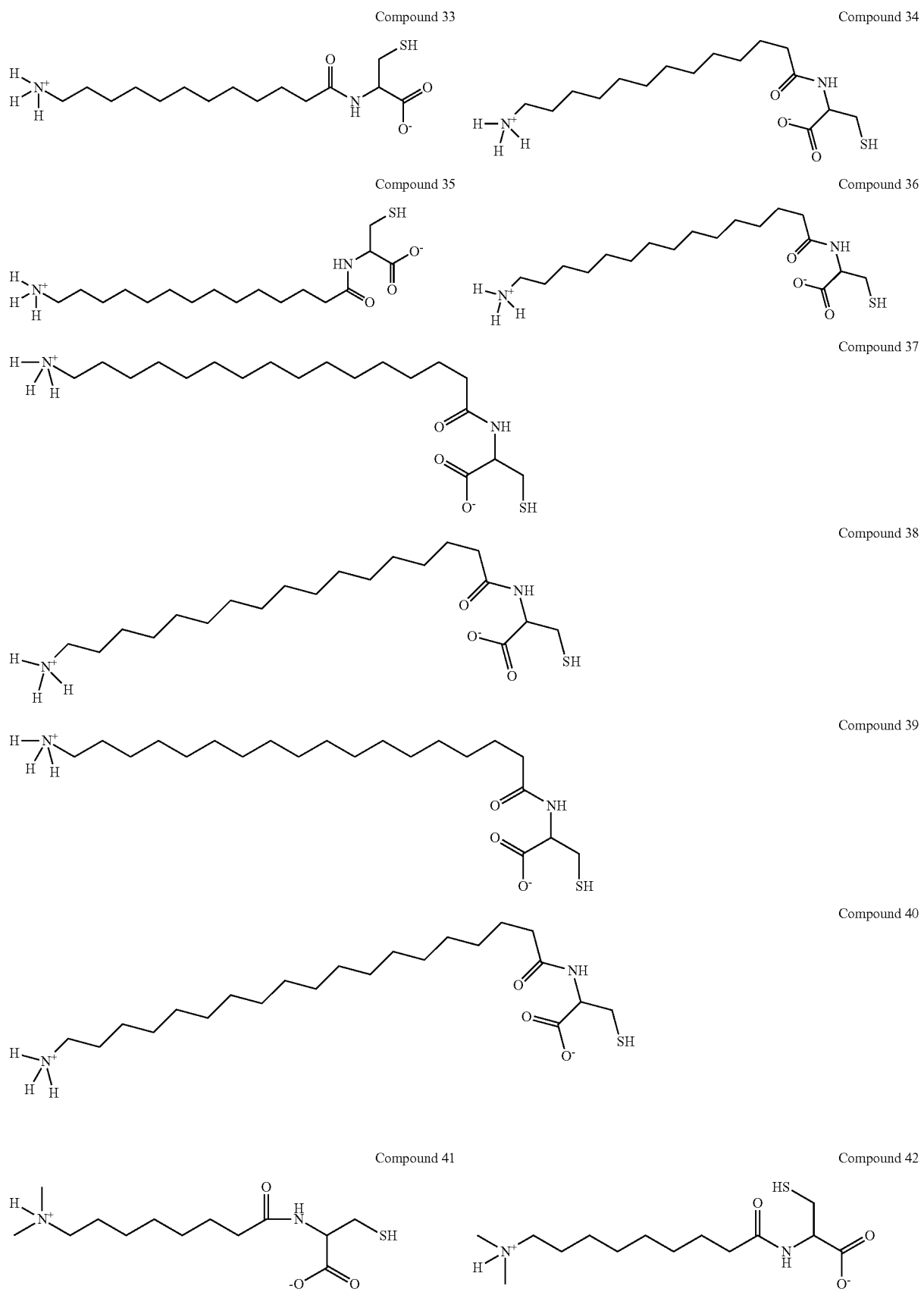

-continued
Compound 43
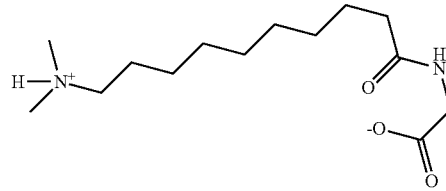
Compound 44
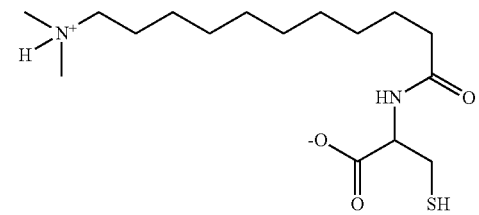
Compound 45
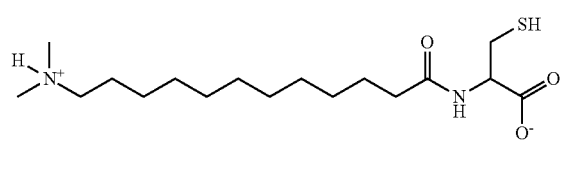
Compound 46
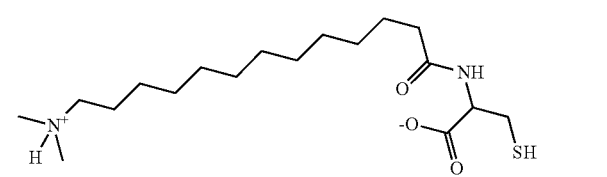
Compound 47
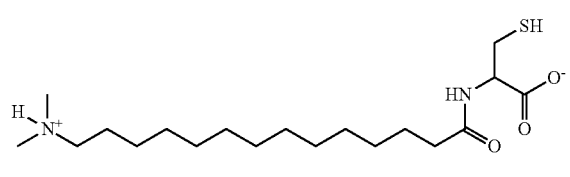
Compound 48
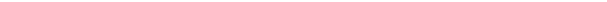
Compound 49
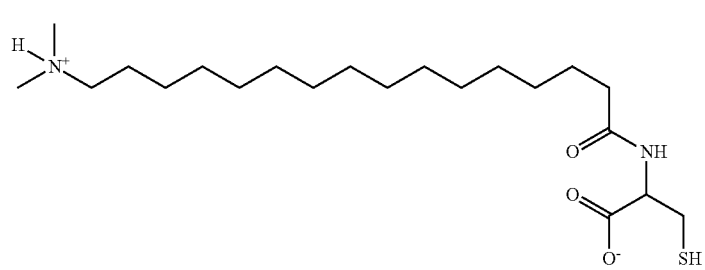
Compound 50
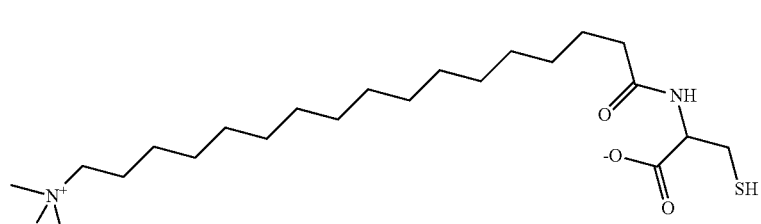
Compound 51
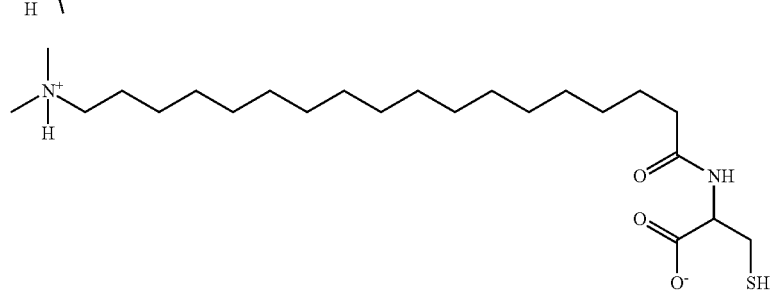
Compound 52
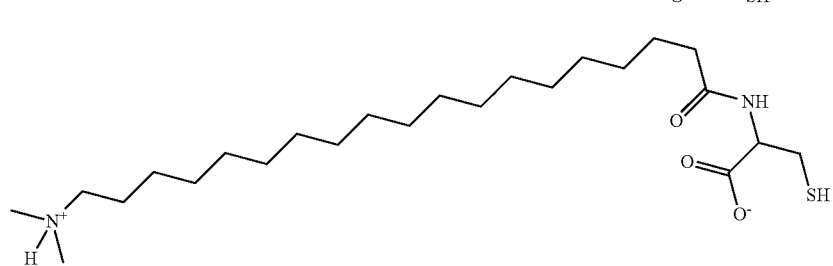

-continued
Compound 53
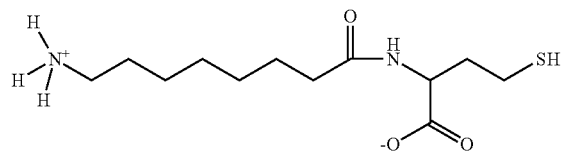
Compound 54
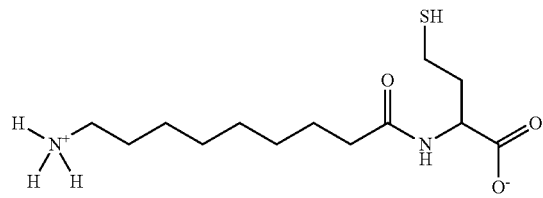
Compound 55
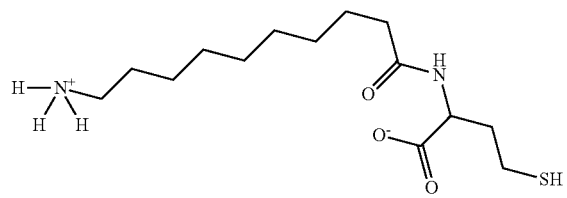
Compound 56
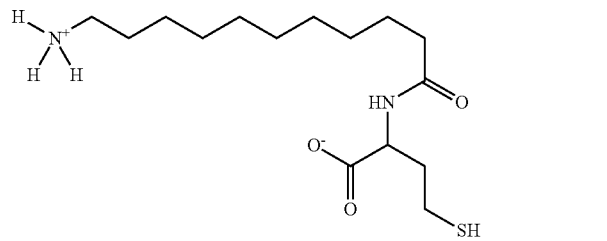
Compound 57
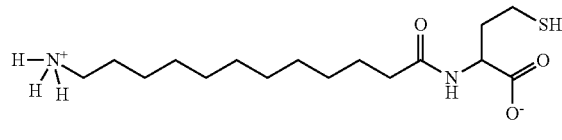
Compound 58
Compound 59
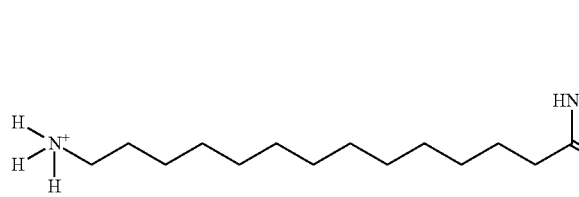
Compound 60
Compound 61
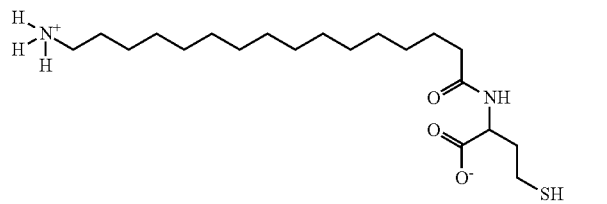
Compound 62
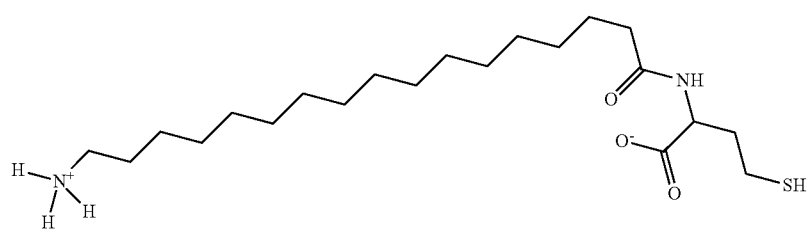
Compound 63
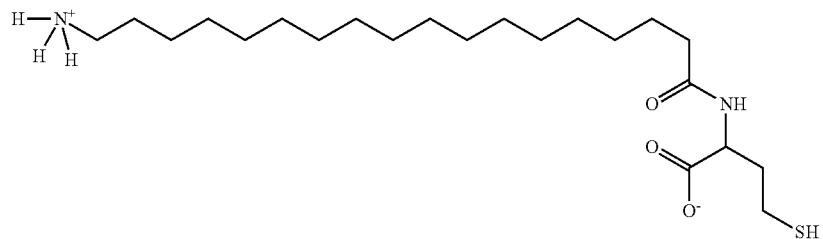

-continued
Compound 64
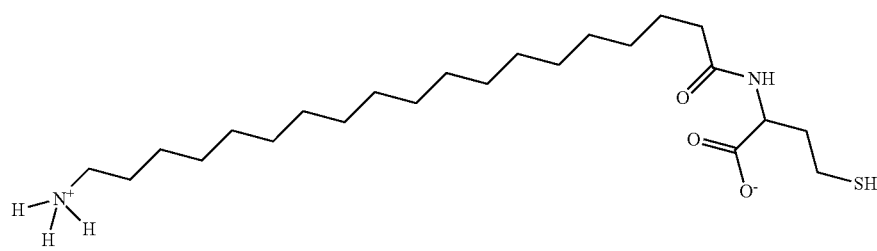
Compound 65
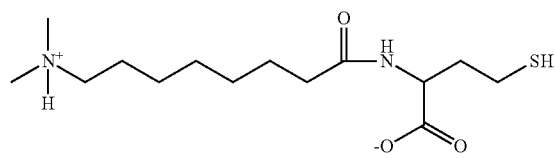
Compound 66
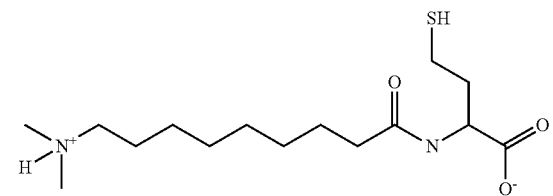
Compound 67
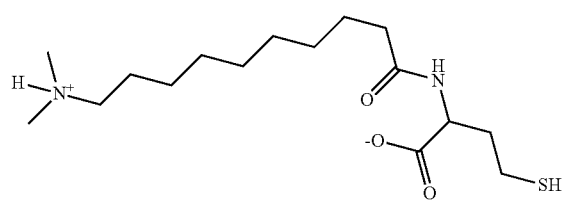
Compound 68
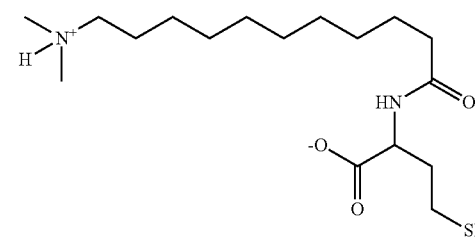
Compound 69
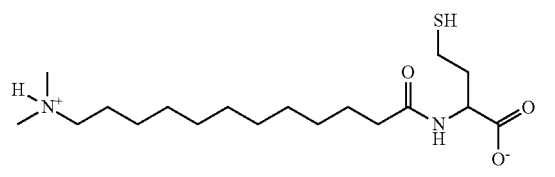
Compound 70
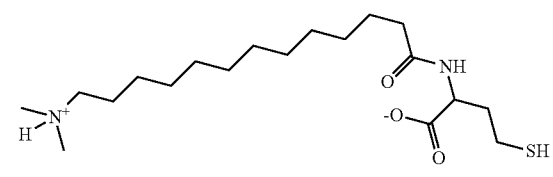
Compound 71
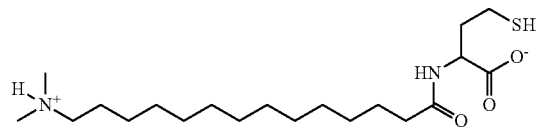
Compound 72
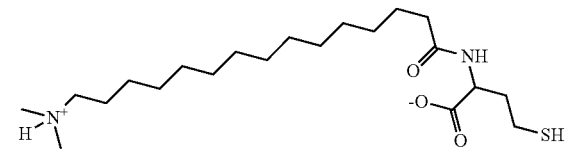
Compound 73
Compound 74

-continued
Compound 75
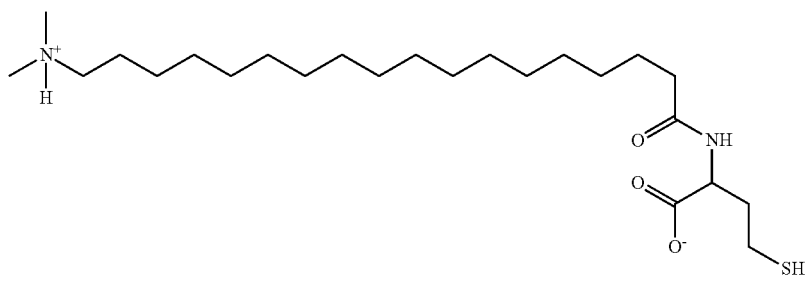
Compound 76
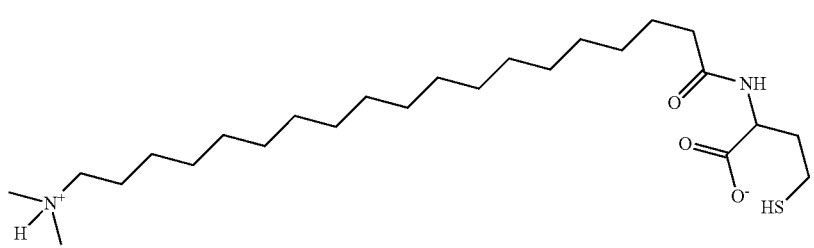
Compound 77
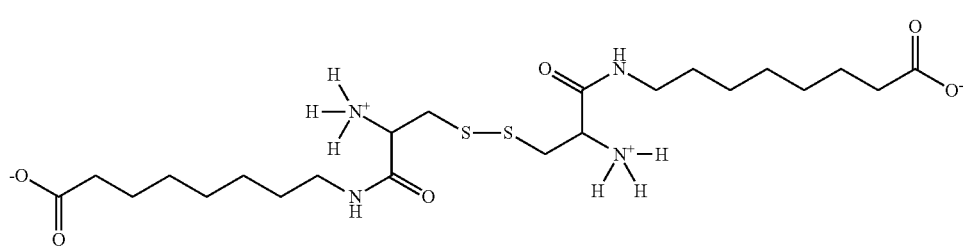
Compound 78
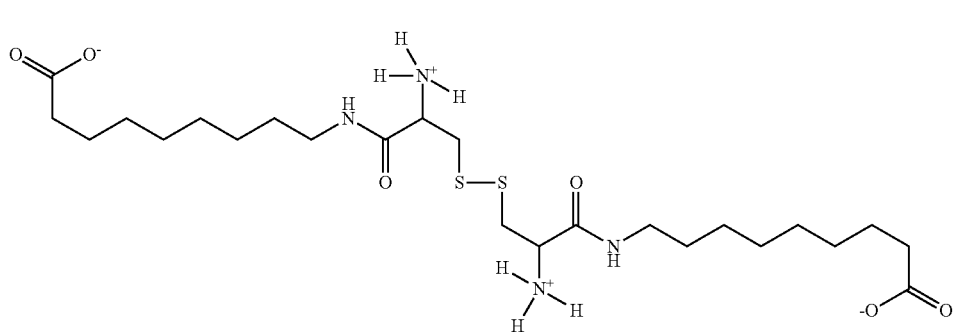
Compound 79
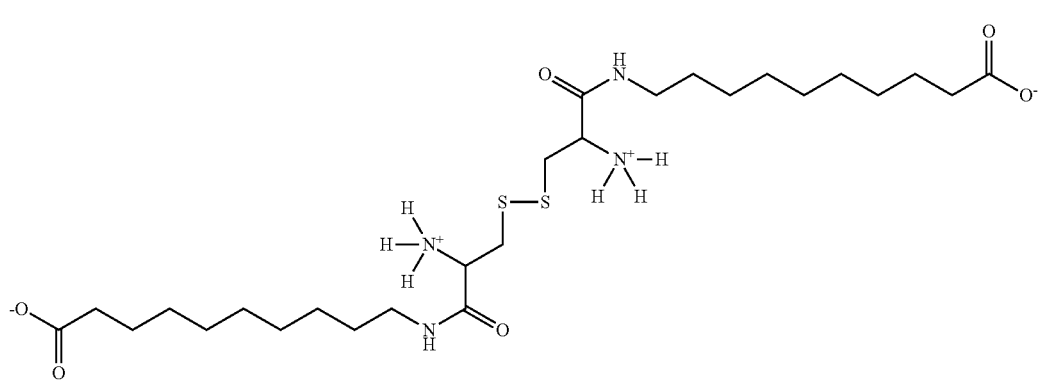

-continued
Compound 80
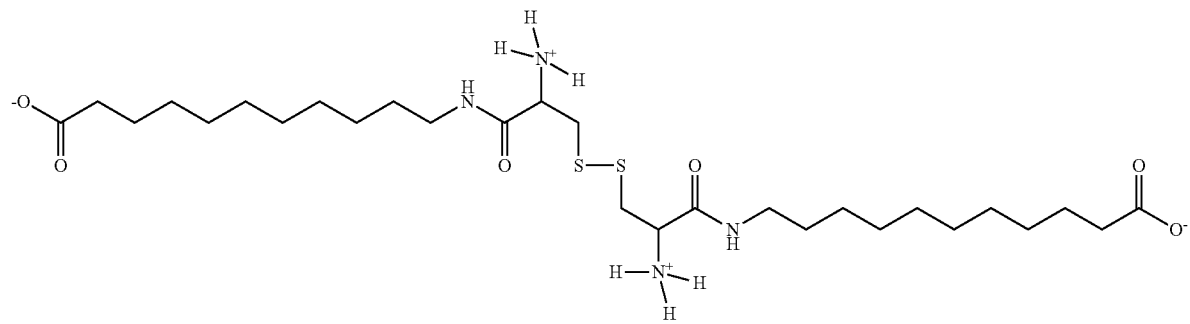
Compound 81
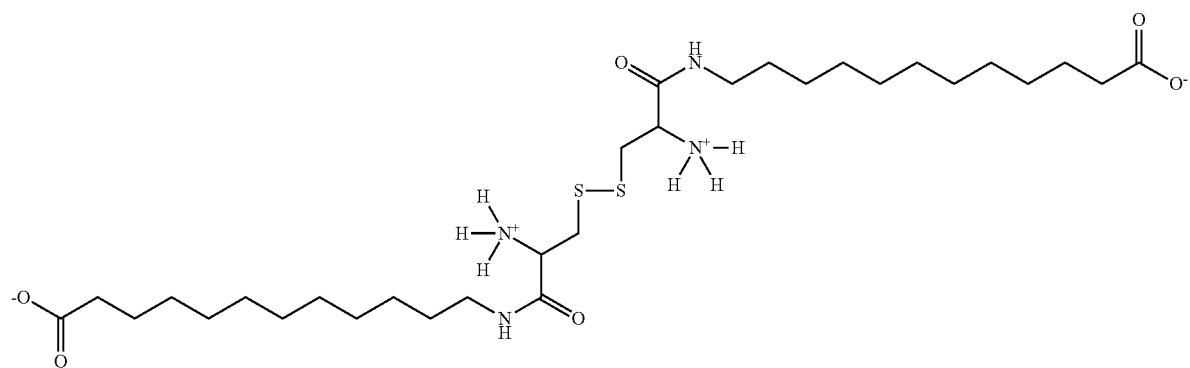
Compound 82
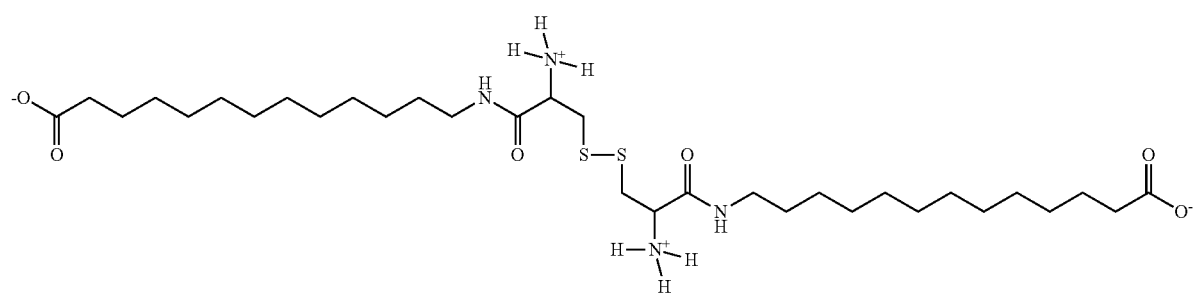
Compound 83
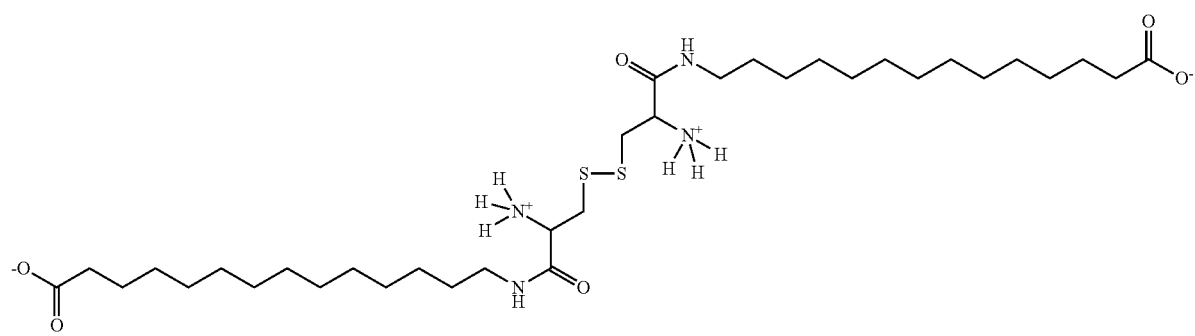

-continued
Compound 84
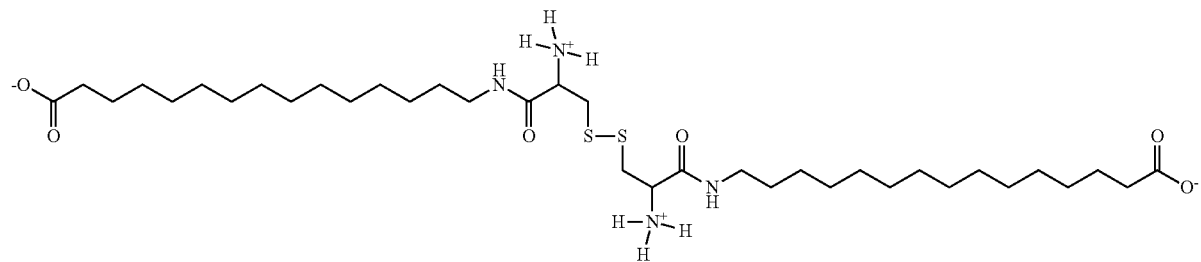
Compound 85
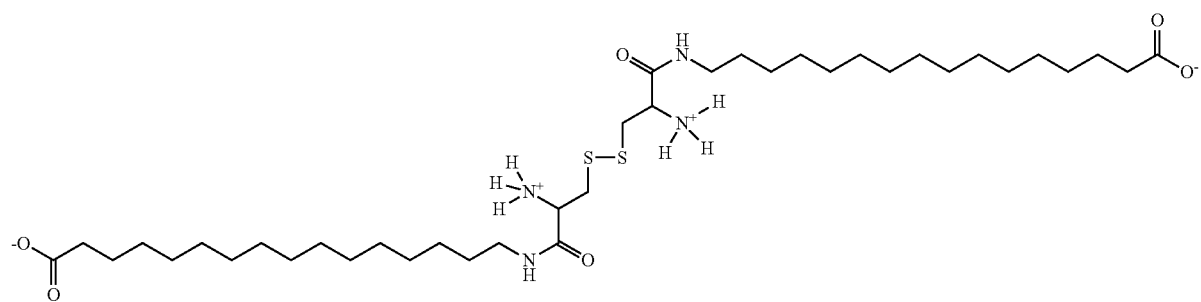
Compound 86
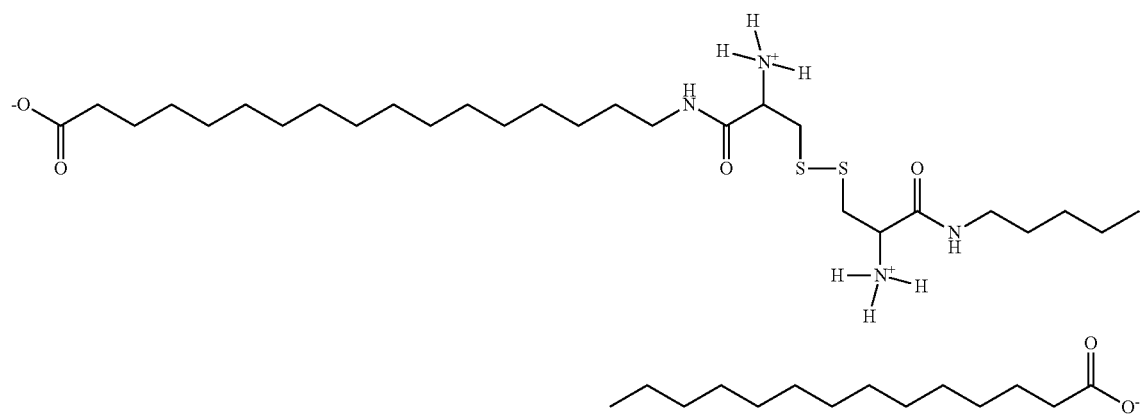
Compound 87
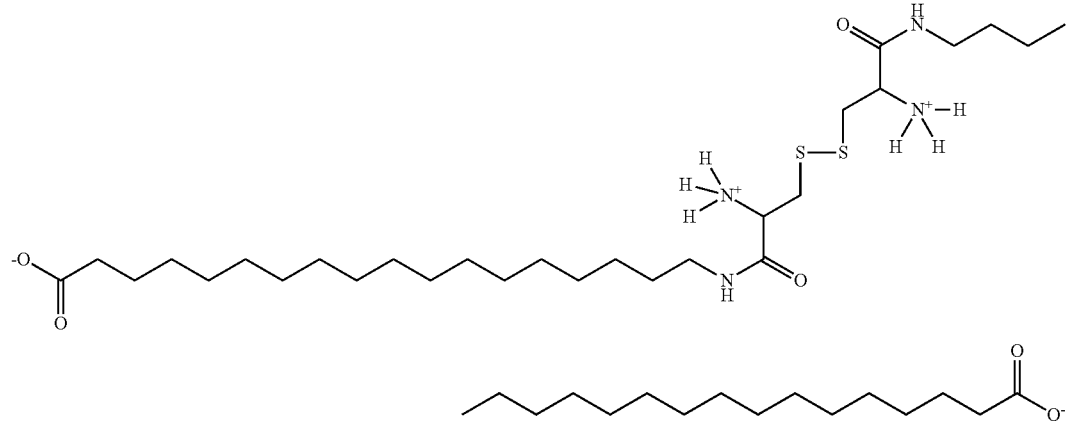

-continued
Compound 88
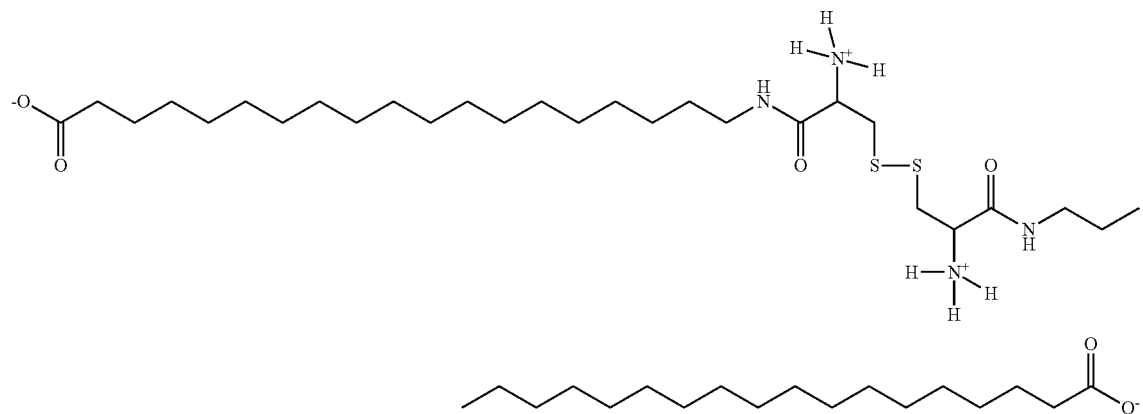
Compound 89
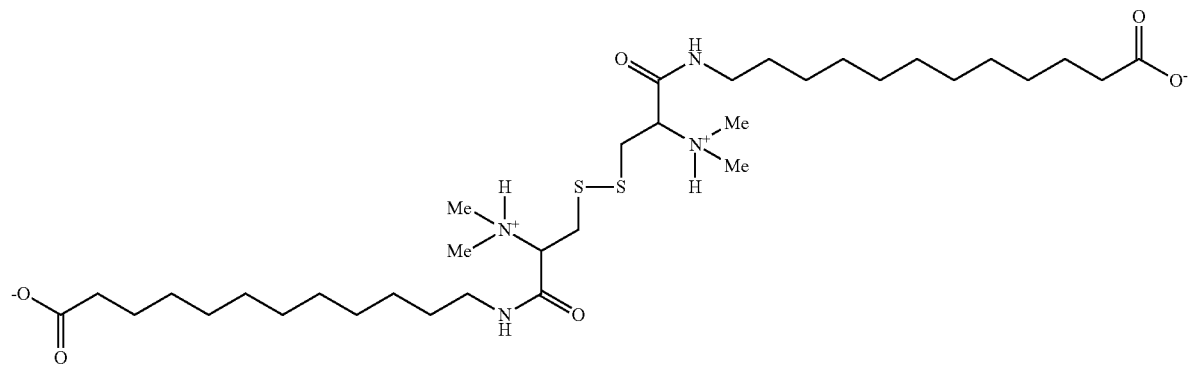
Compound 90
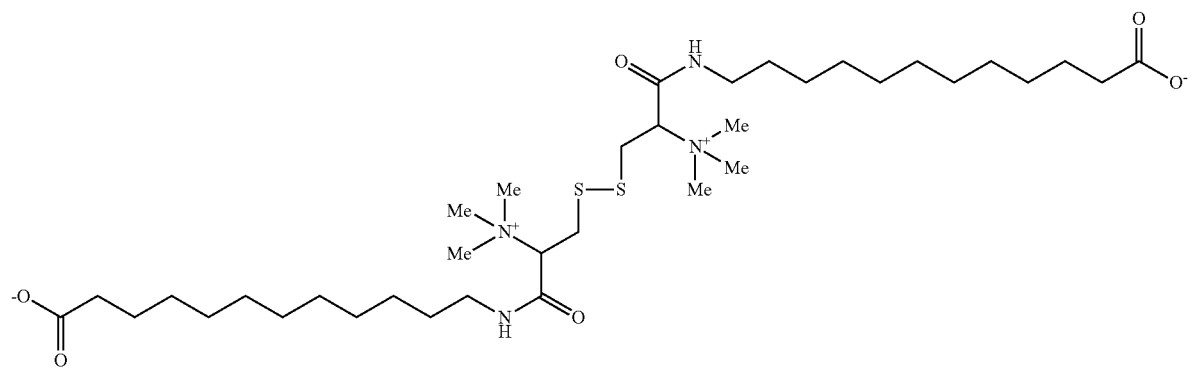
Compound 91
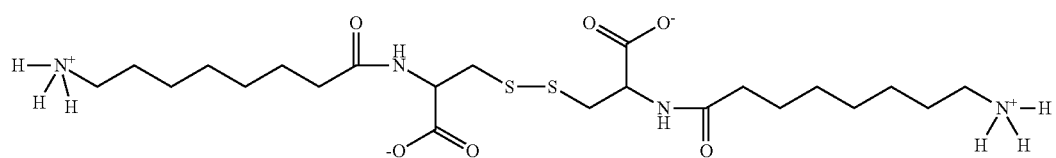

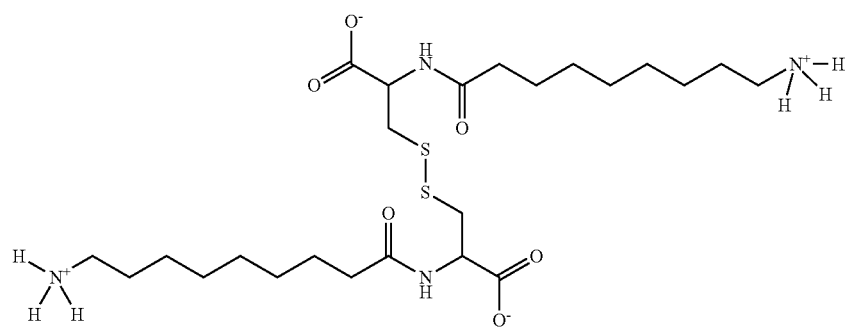
Compound 92
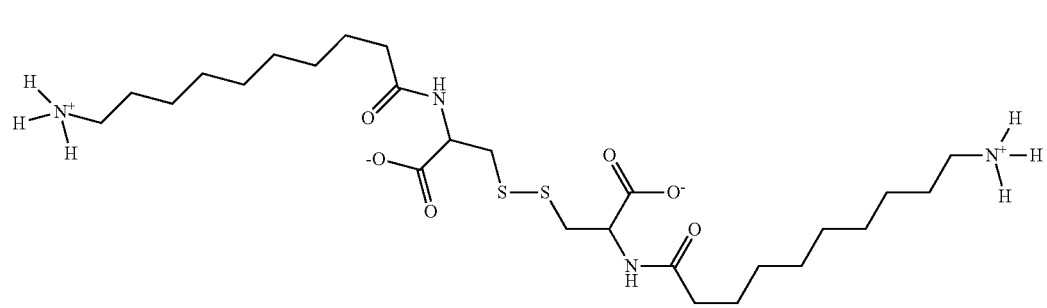
Compound 93
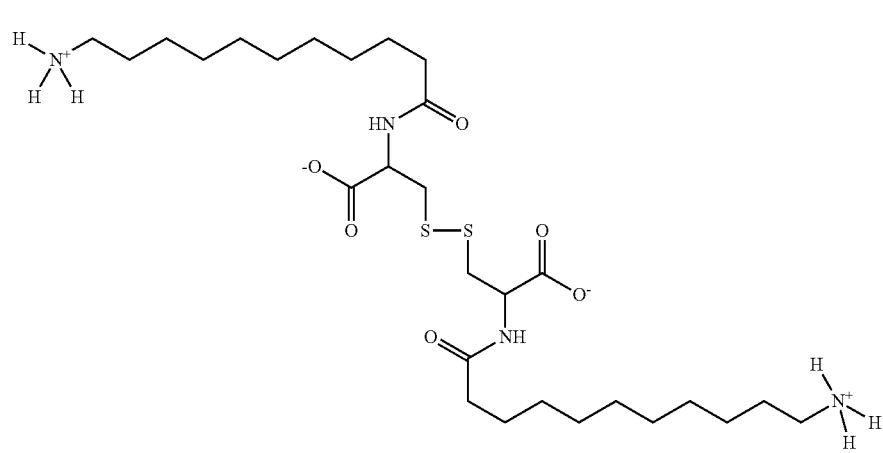
Compound 94
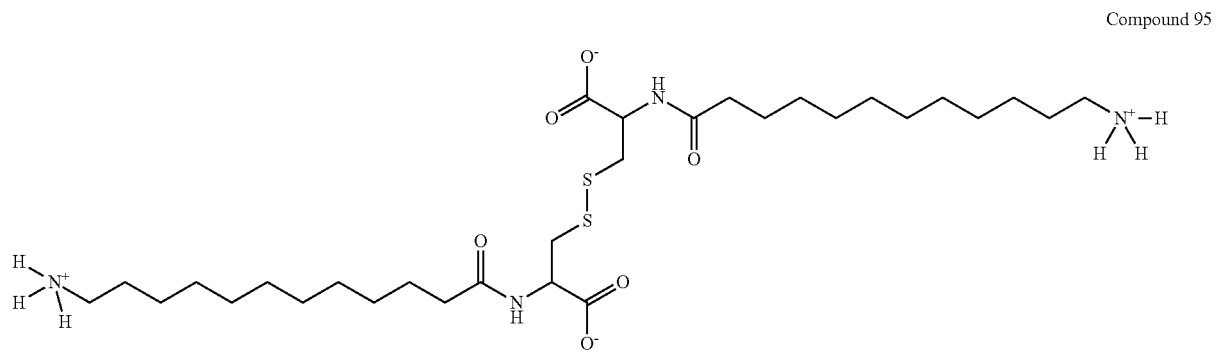
Compound 95

-continued
Compound 96
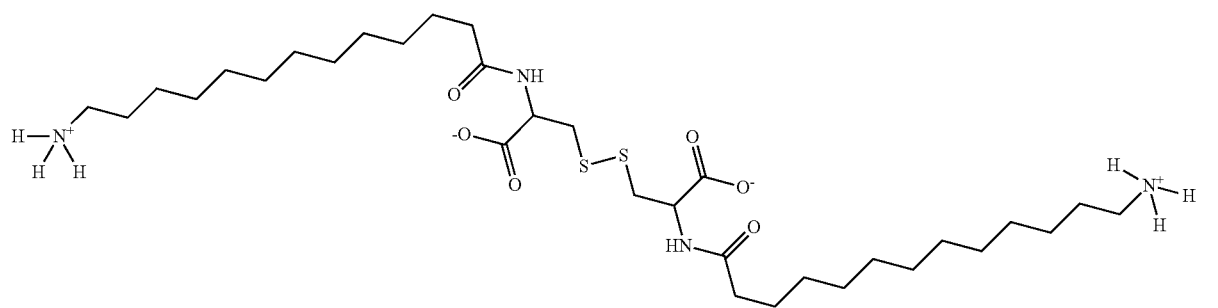
Compound 97
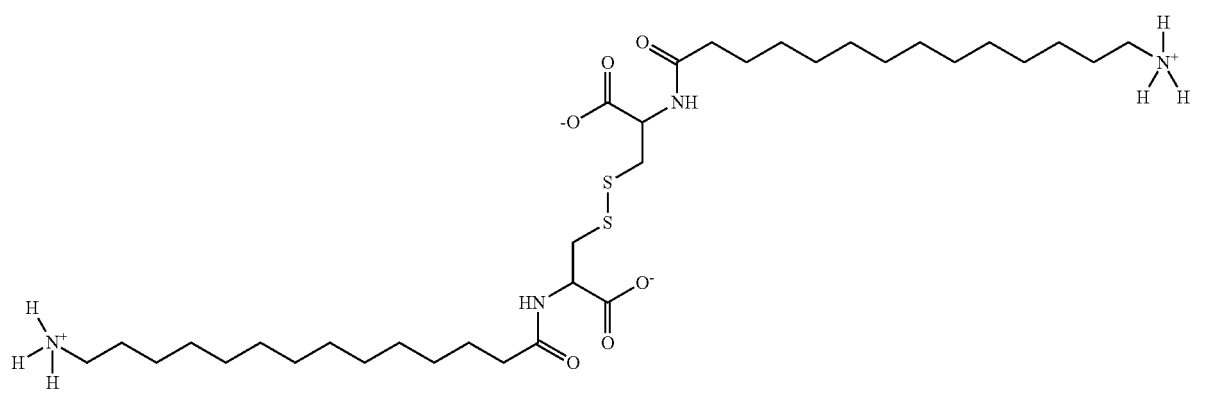
Compound 98
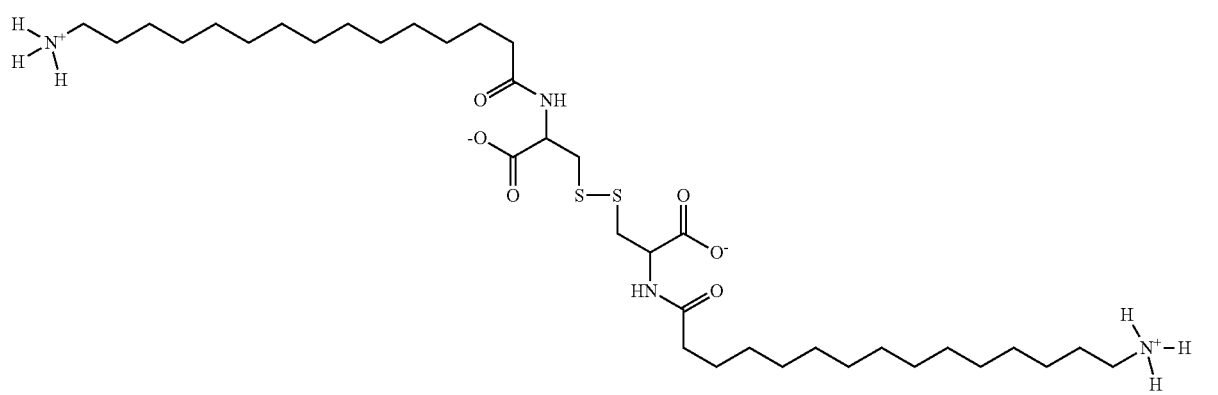
Compound 99
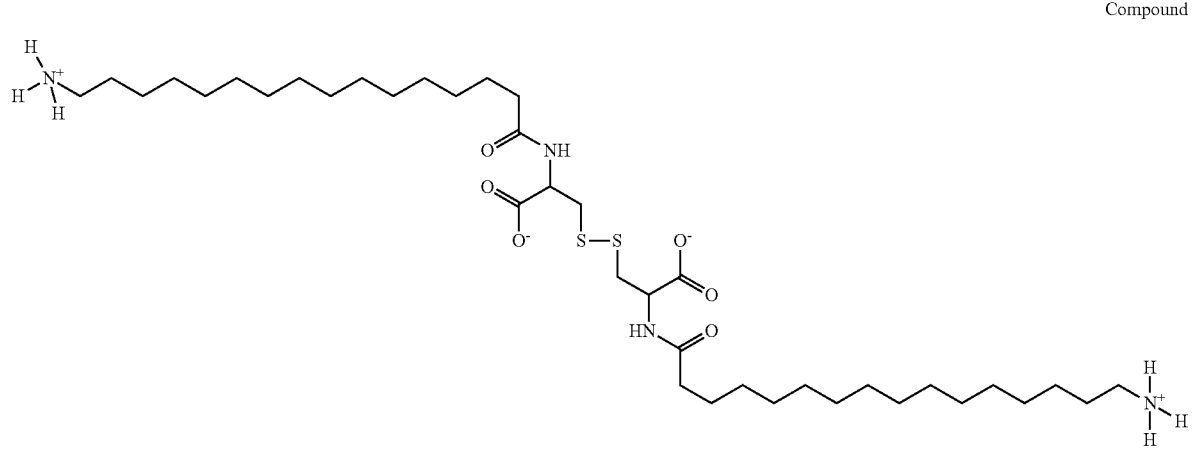

-continued
Compound 100
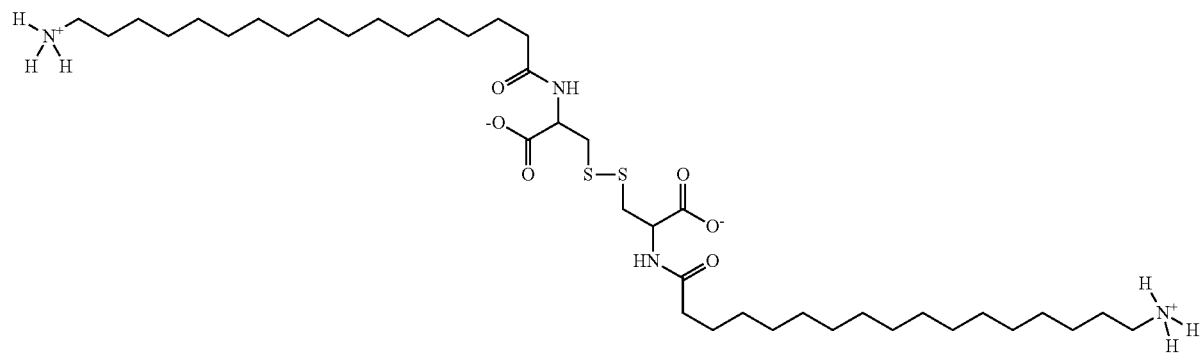
Compound 101
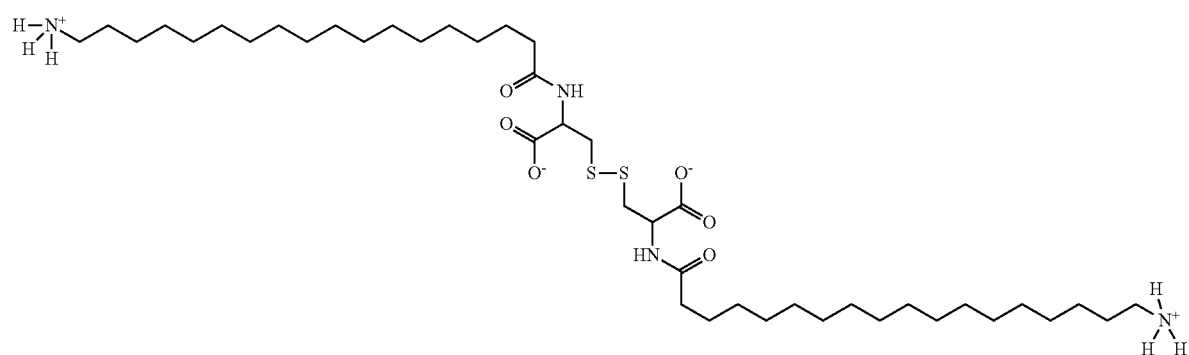
Compound 102
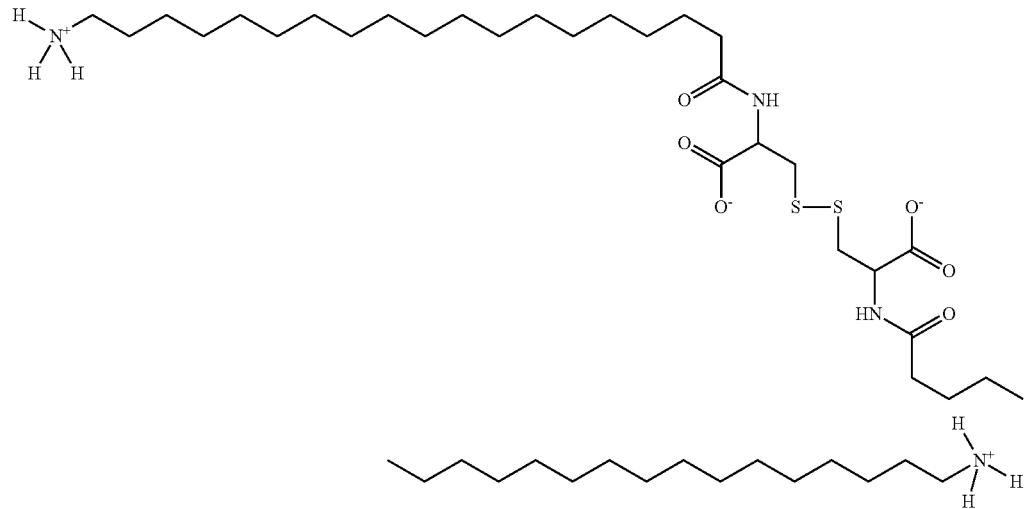
Compound 103
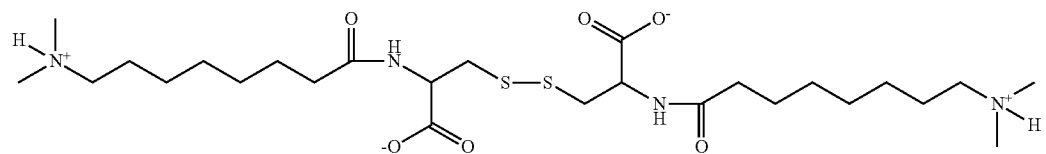

-continued
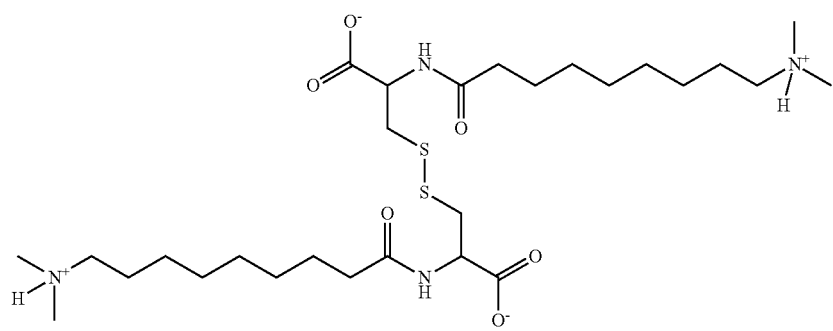
Compound 104
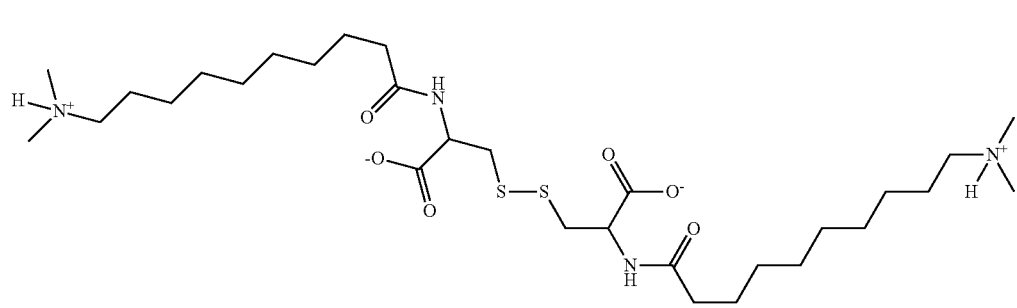
Compound 105
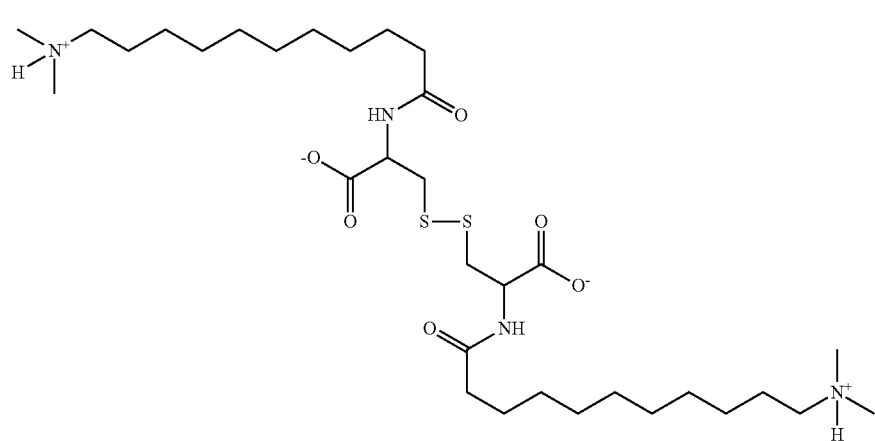
Compound 106
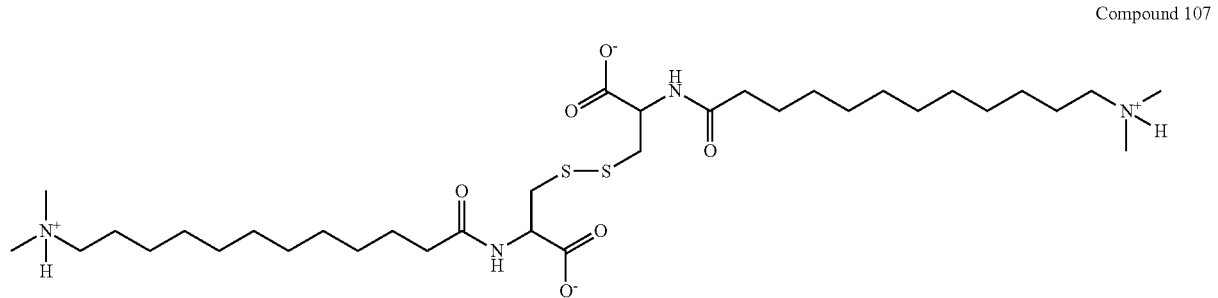
Compound 107

-continued
Compound 108
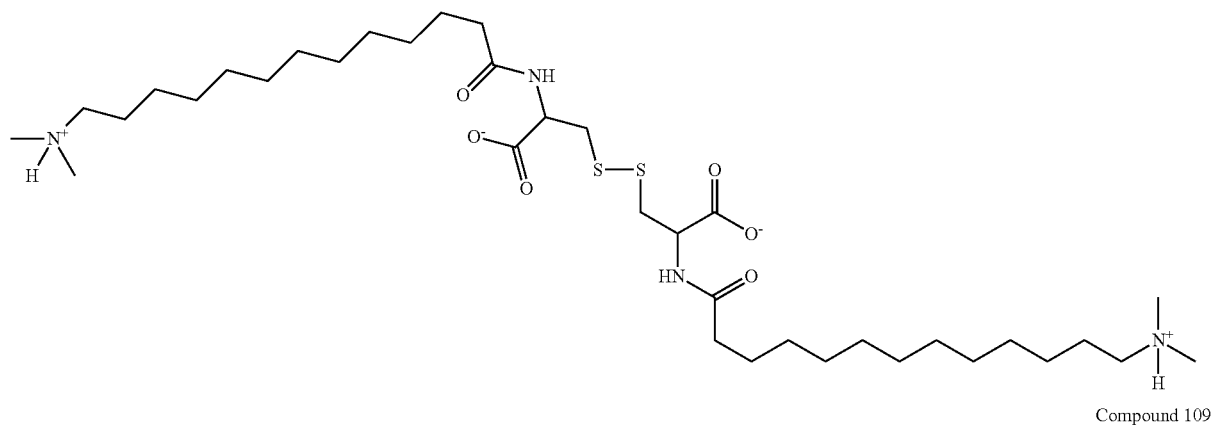
Compound 109
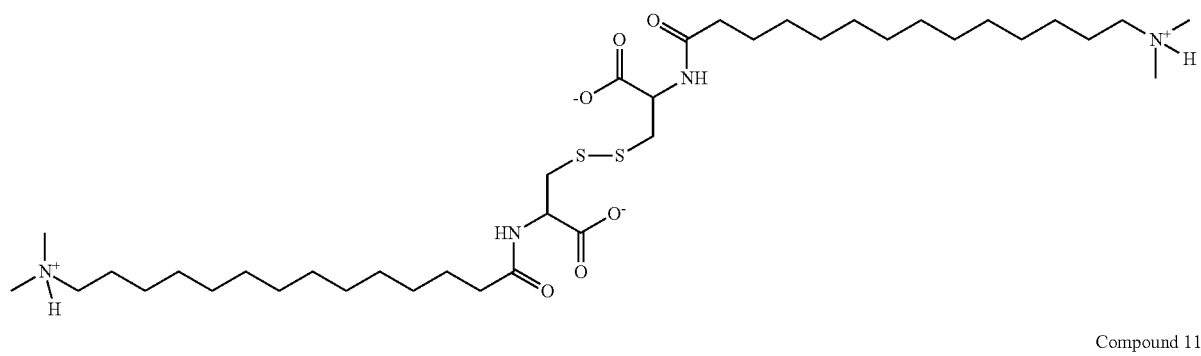
Compound 110
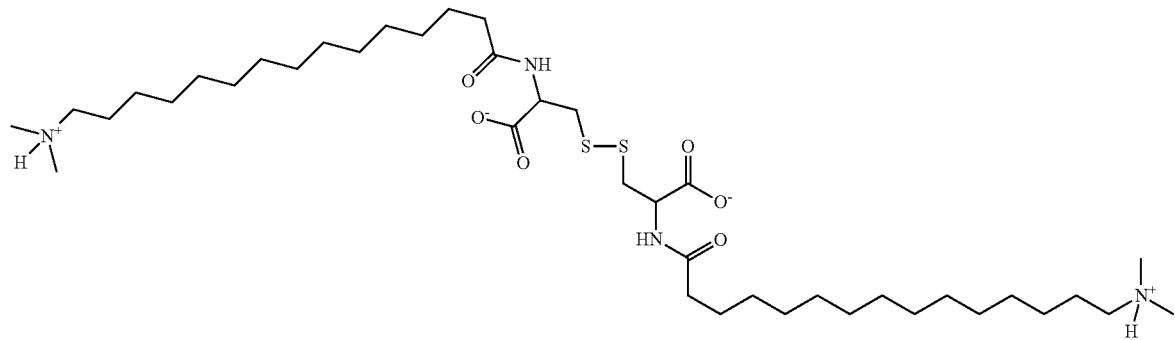
Compound 111
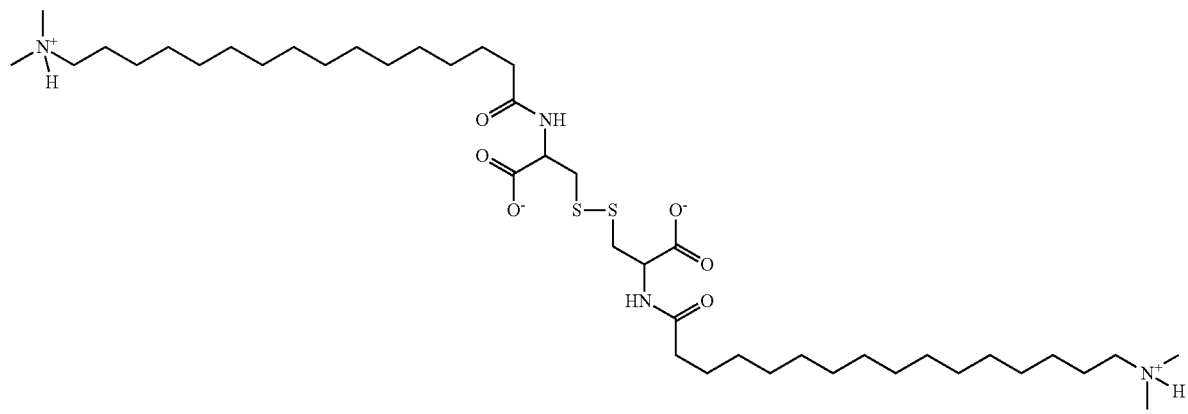

-continued
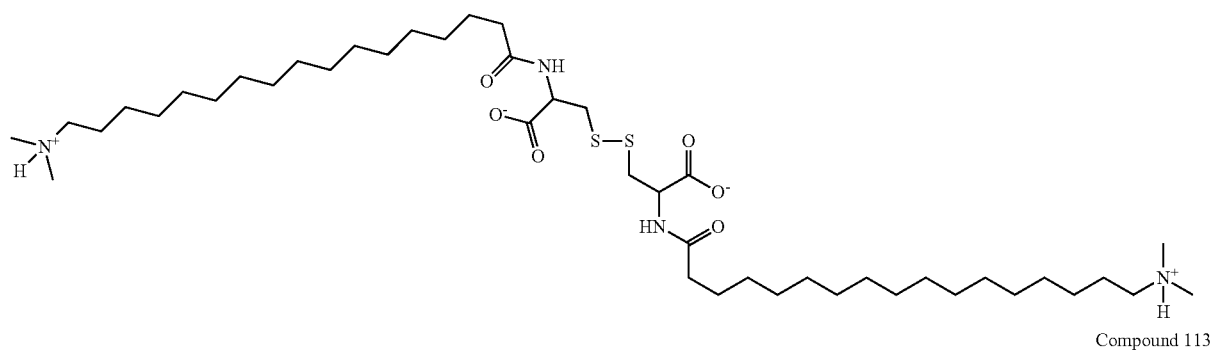
Compound 112
Compound 113
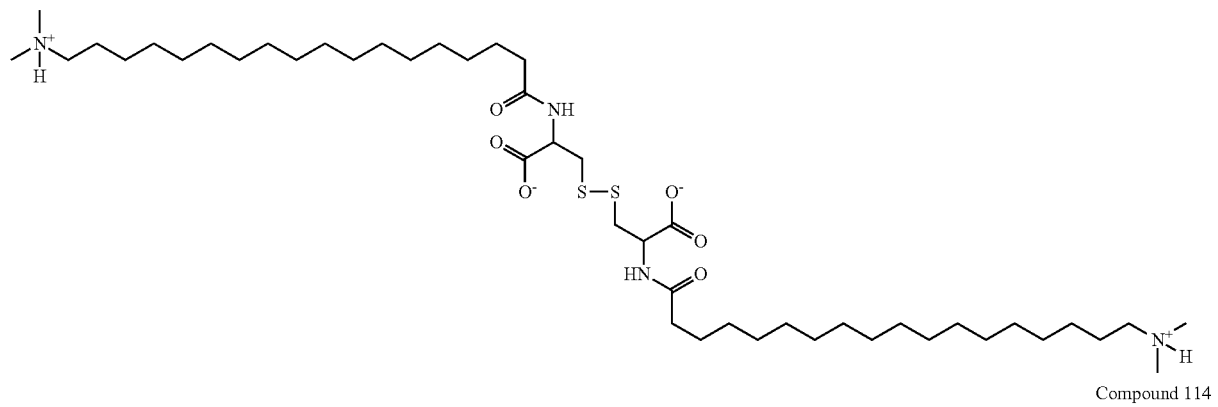
Compound 114
Compound 115
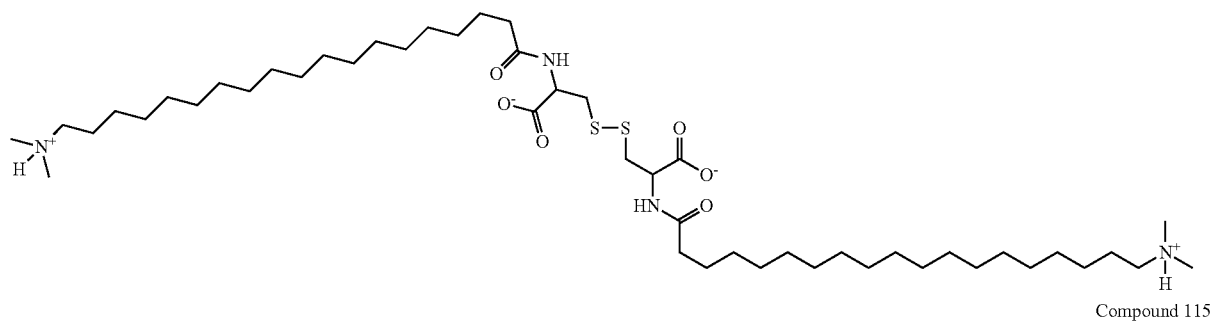
Compound 116
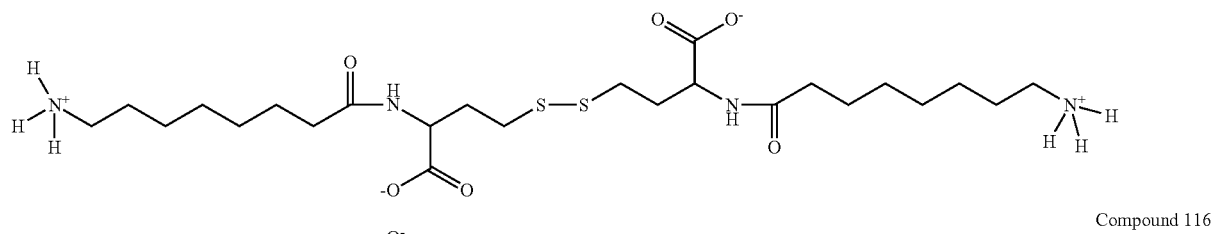
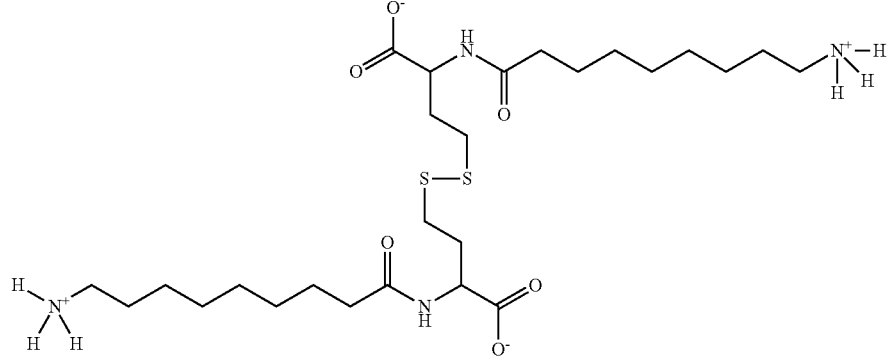

Compound 117
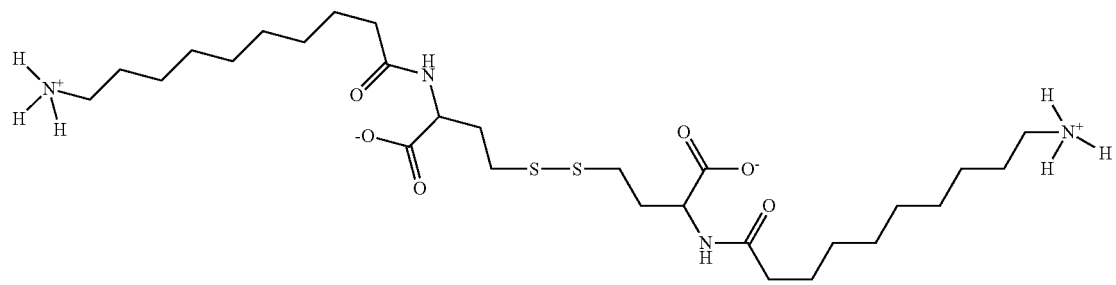
Compound 118
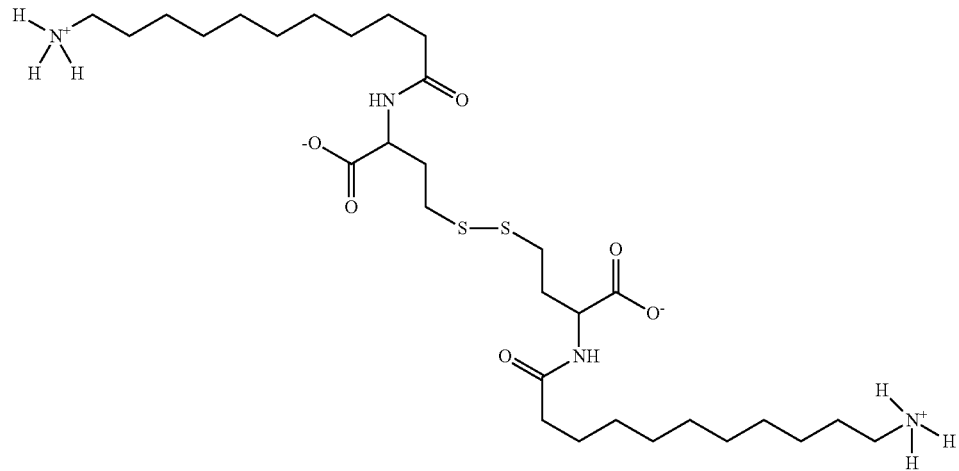
Compound 119
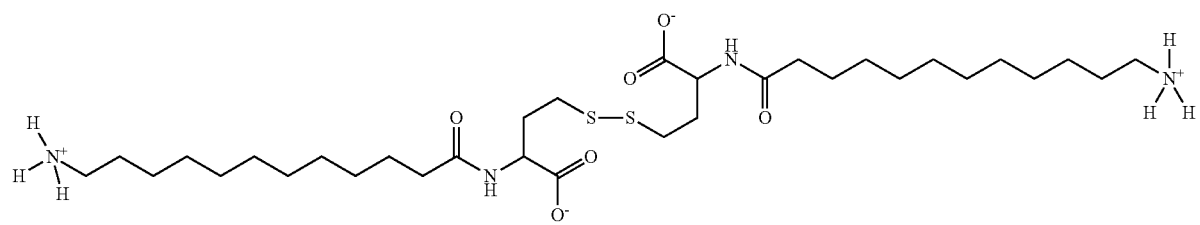
Compound 120
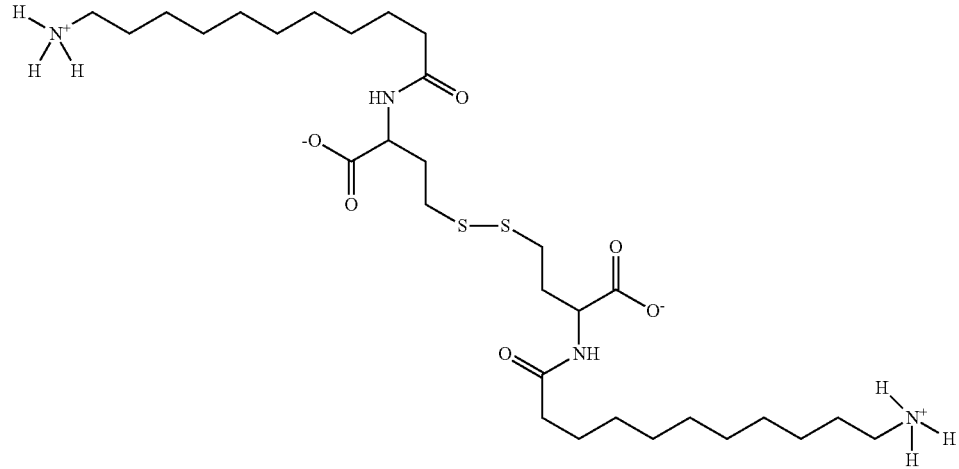

-continued
Compound 121
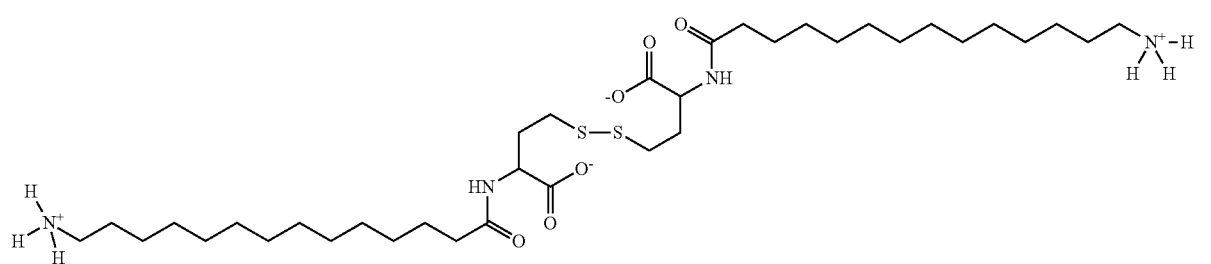
Compound 122
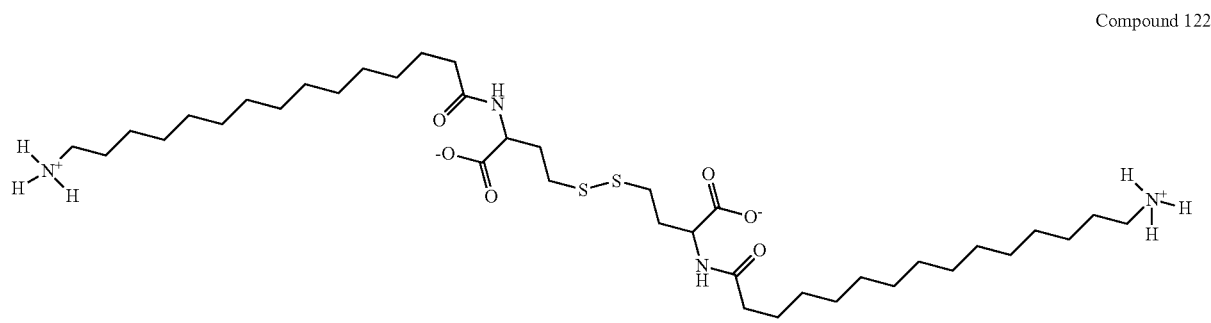
Compound 123
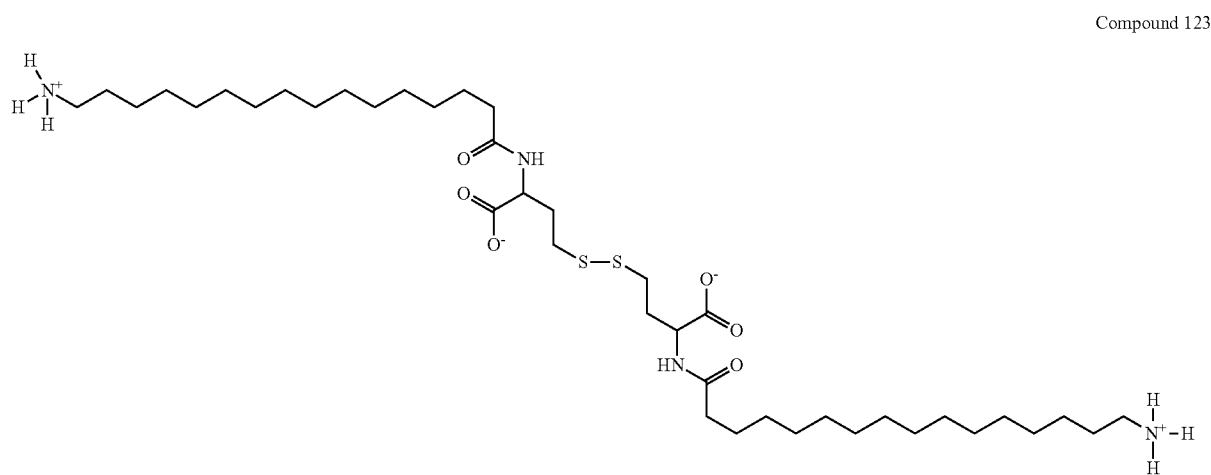
Compound 124
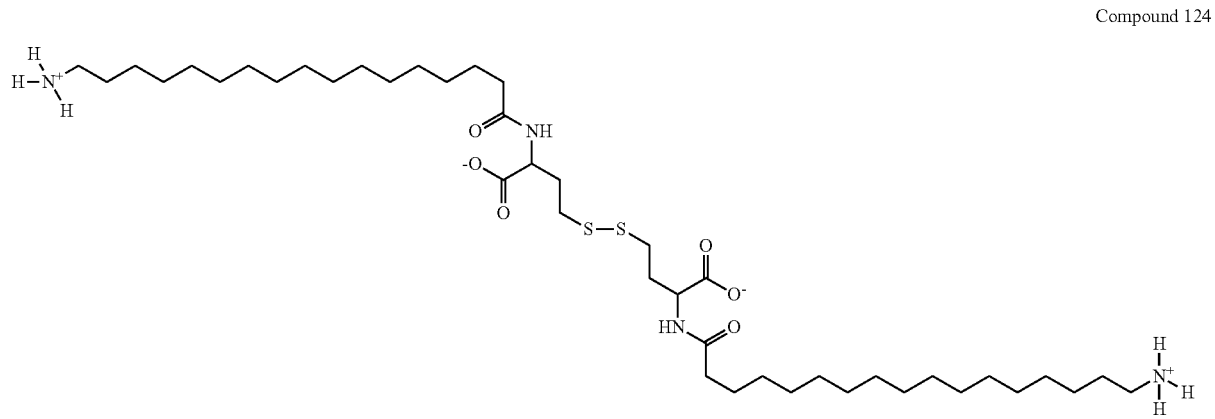

-continued
Compound 125
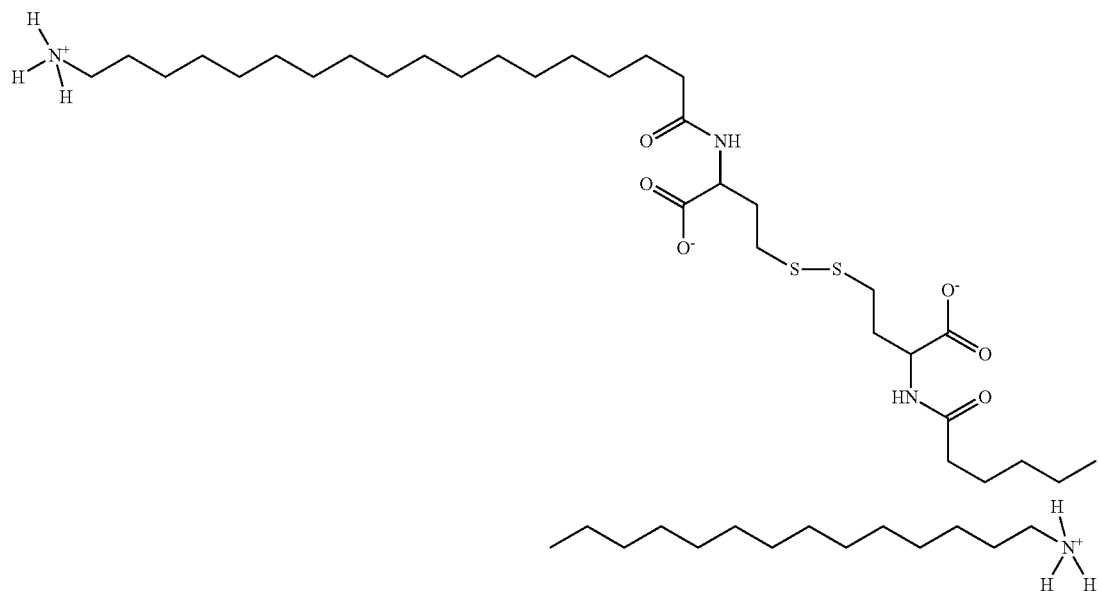
Compound 126
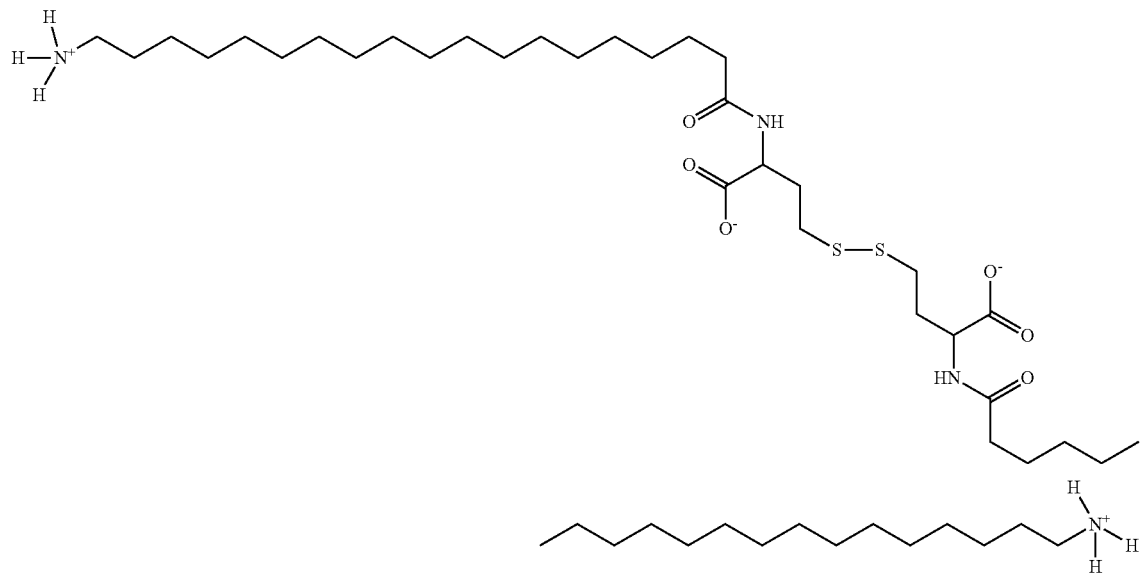
Compound 127
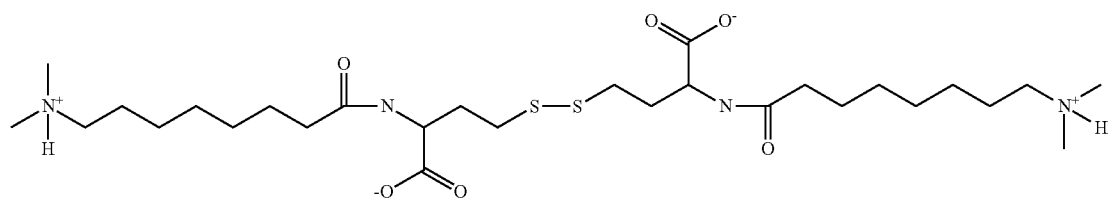

-continued
Compound 128
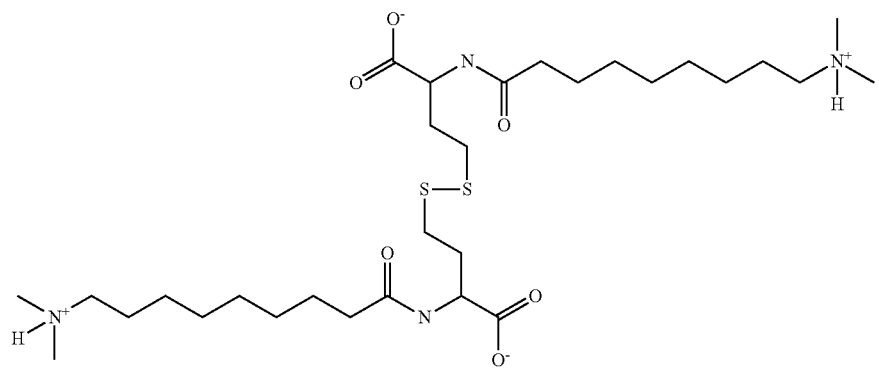
Compound 129
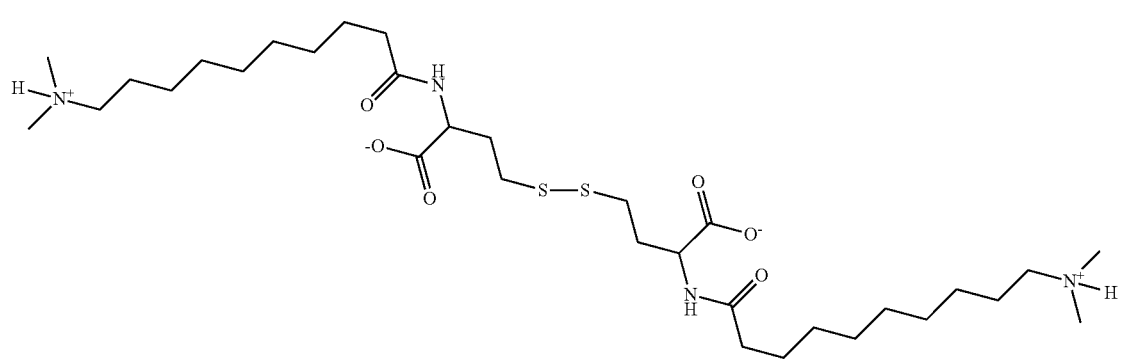
Compound 130
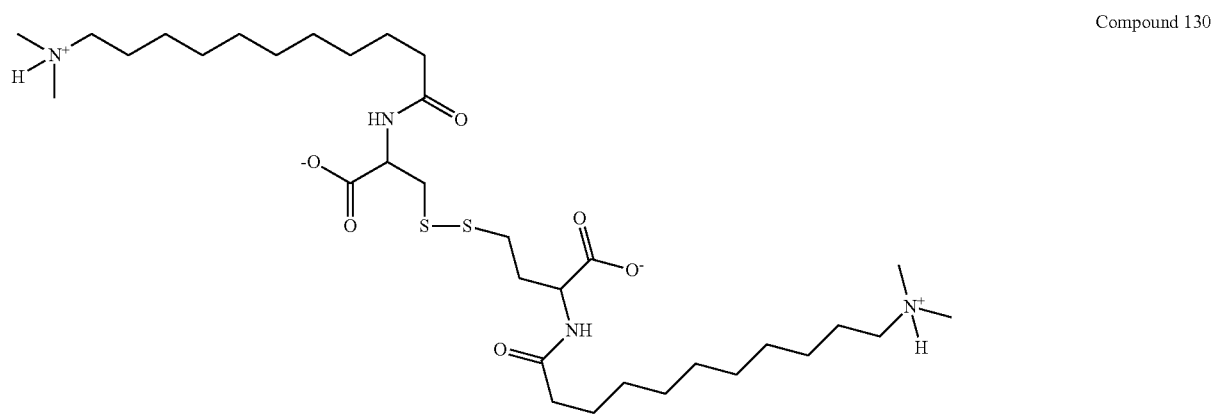
Compound 131
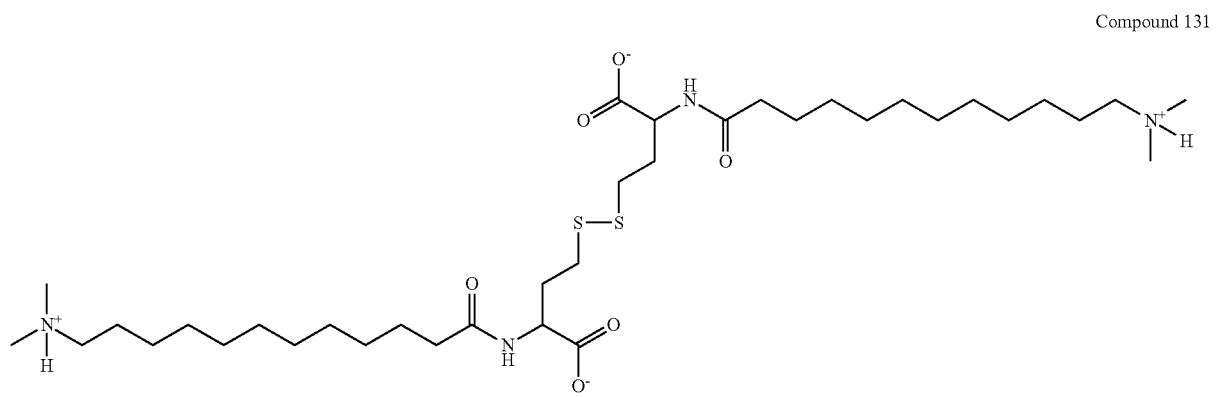

-continued
Compound 132
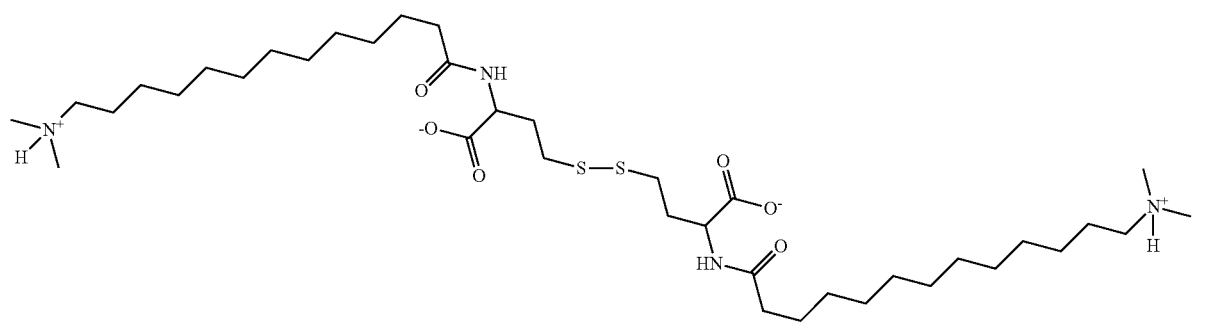
Compound 133
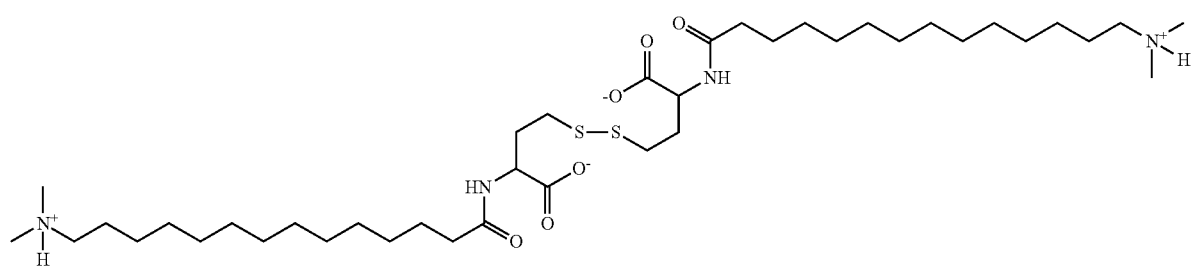
Compound 134
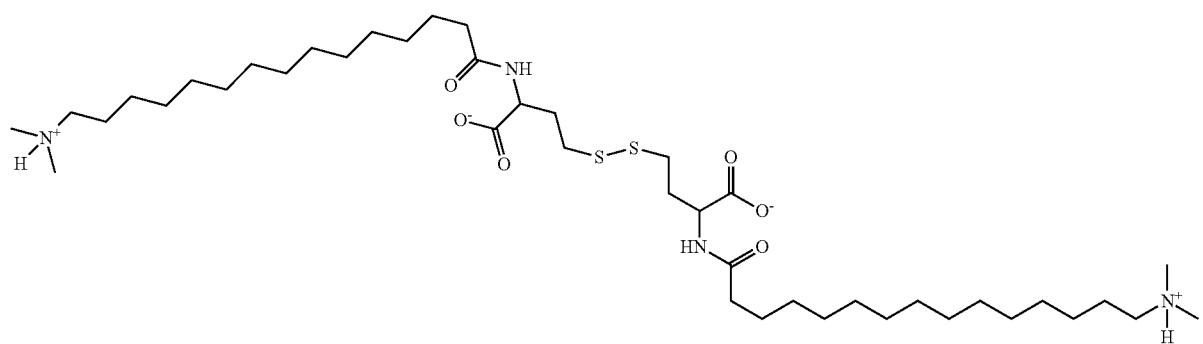
Compound 135
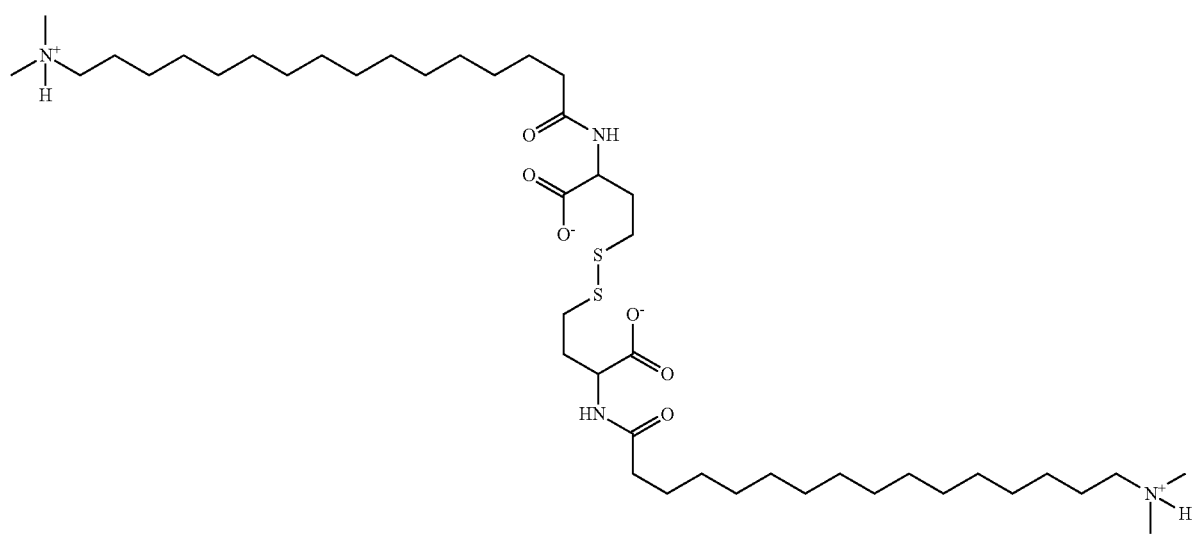

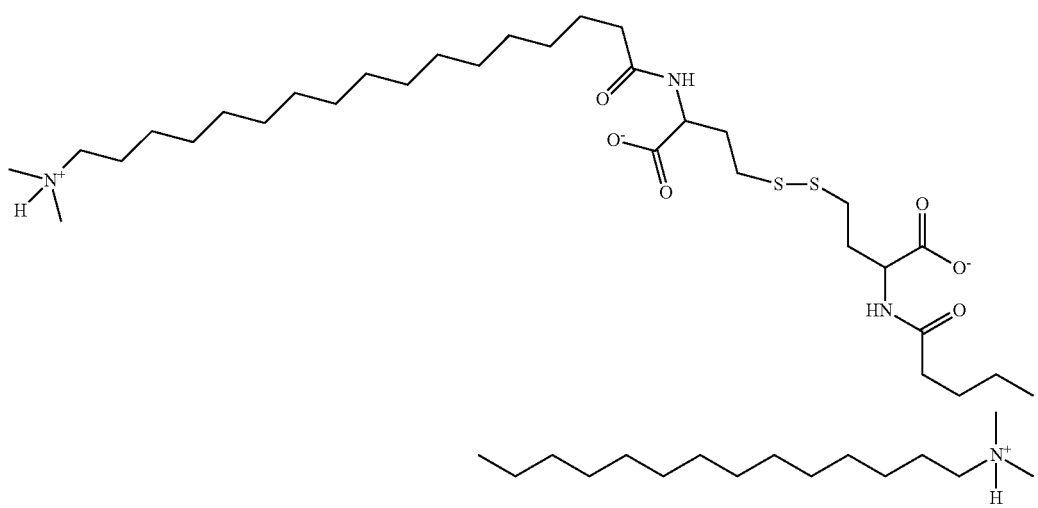

Compound 136

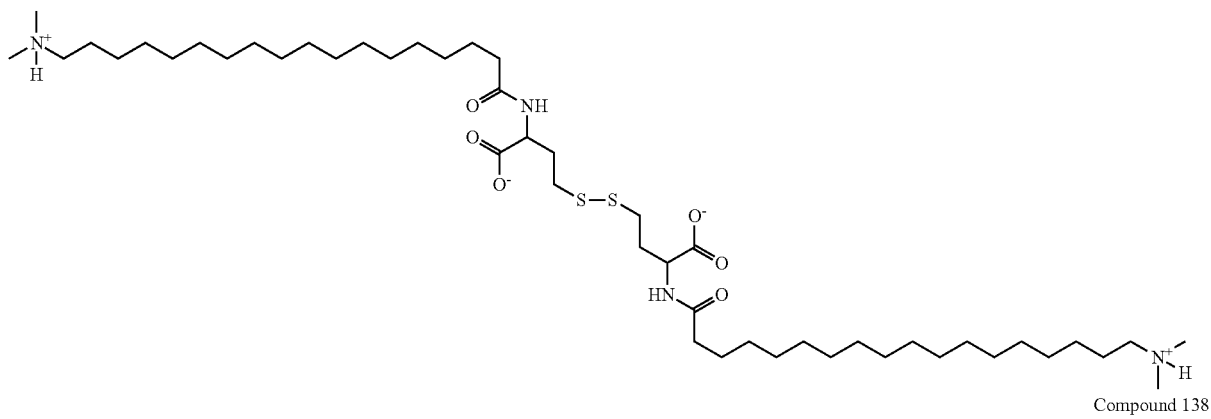

Compound 137

Compound 138

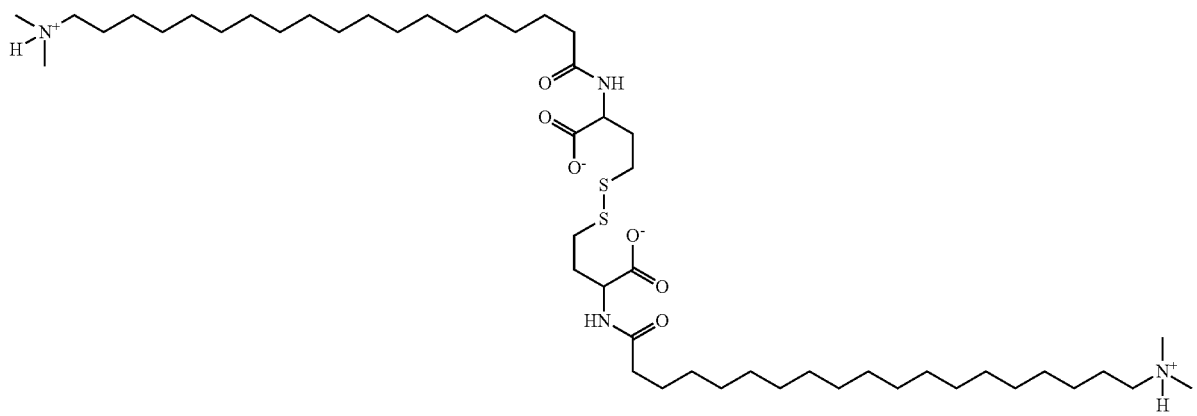

The disulfide compounds of formulae (Id) and (IId) can be prepared according to methods known to those skilled in the art. According to a first possibility, a disulfide compound comprising two primary amine functions can be reacted with a sufficient amount of a compound carrying a carboxylate function (carboxylic acid salt). This reaction to form an amide bond is known to those skilled in the art. The carboxylic acid can be activated via reactions known to those skilled in the art. Mention may be made of the chlorination reaction with thionyl chloride ($SOCl_2$) so as to convert the carboxylic acid (C(=O)OH) into the acyl chloride ((C=O)Cl). These "activated" carboxylic acids are more reactive than the carboxylic acids and make it possible to carry out the reactions at lower temperatures and more rapidly. Reference may in particular be made to the handbook Advanced Organic Chemistry, March 4th Ed., for these reactions. Protective groups for the amines and carboxylic acids can be used in the reactions in order to improve the yield of the reactions. Protective groups for amines and carboxylic acids are known to those skilled in the art. Reference may in particular be made to the handbook Advanced Organic Chemistry, March, 4th Ed., and the article Developments in peptide and amide synthesis, *Curry*

Opin Chem. Biol. 2004 June; 8(3):211-21 for further details on the operating conditions implemented.
Mention may be made, as examples, of the following strategies:
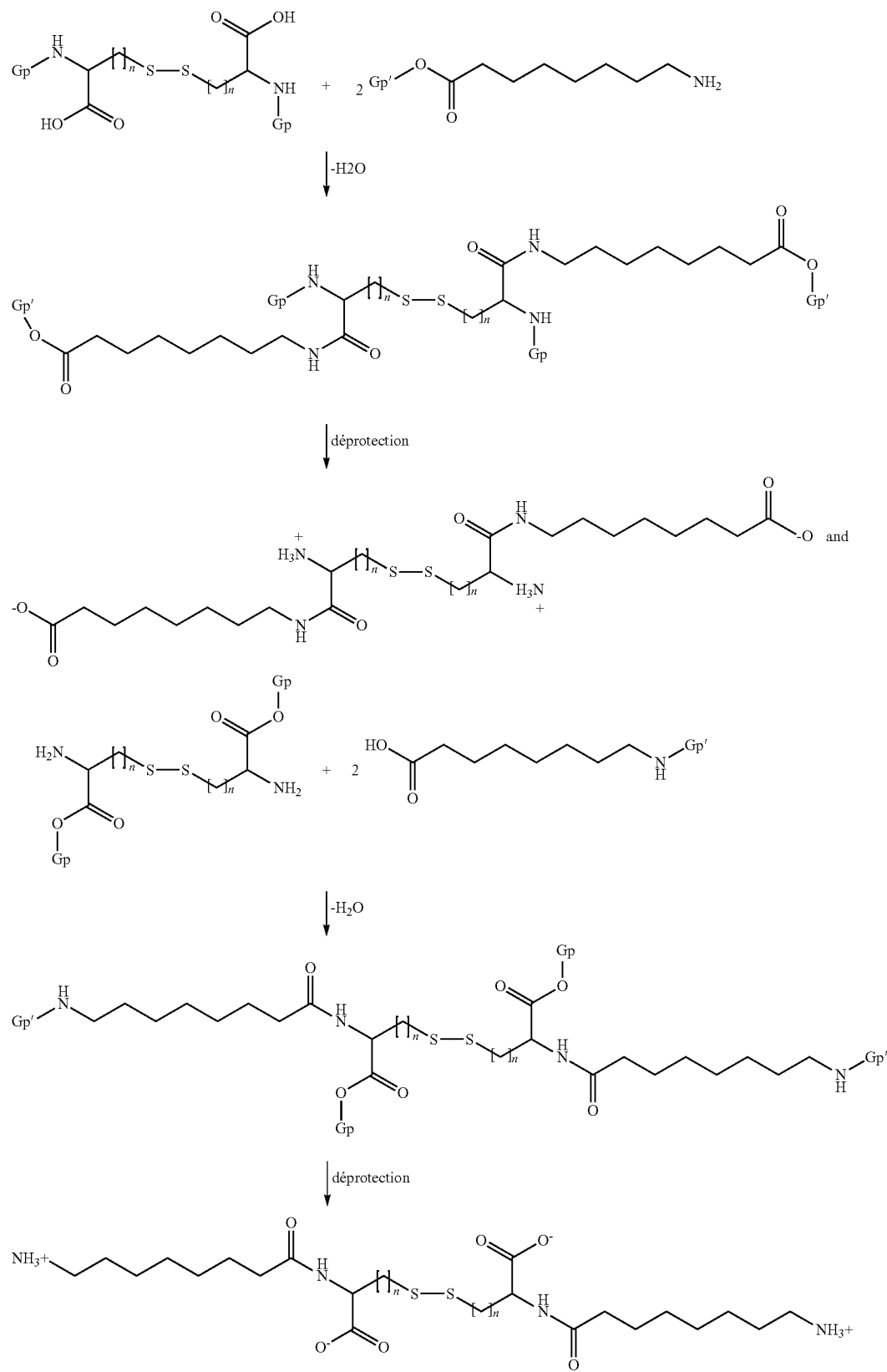

The compounds of formula (I) or (II) in their thiolated form can be synthesised by chemical reduction of the compounds of formula (Id) or (IId) in disulfide form. This is the reduction of a disulfide compound to give a thiolated compound. This reaction to form a thiolated compound is known to those skilled in the art. Reference may in particular be made to the handbook Advanced Organic Chemistry, March 4th Ed., for these reactions. Such an example is shown below.

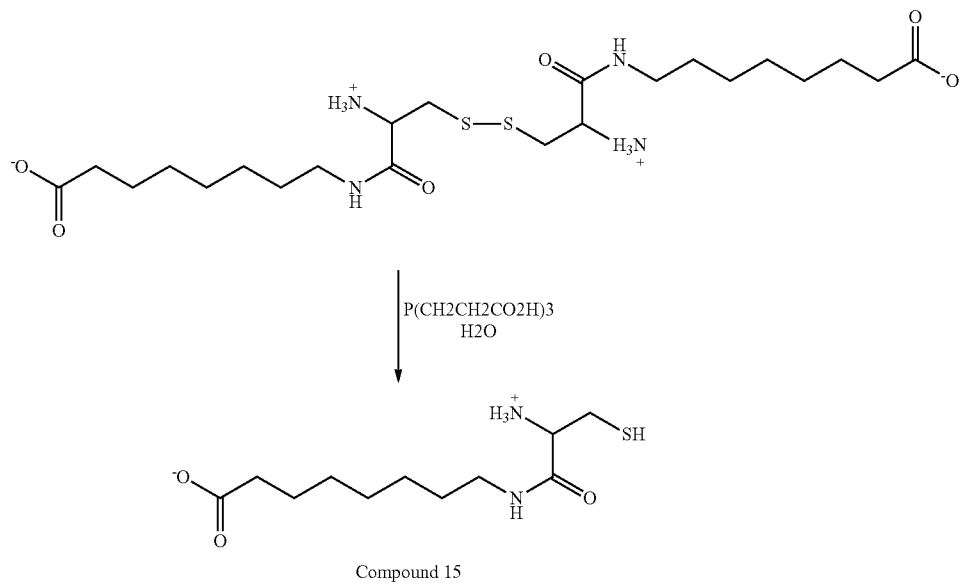

Compound 15

The thiols can be protected with the following functions: alkylcarbonyl, arylcarbonyl, alcoxycarbonyl, aryloxycarbonyl, arylalcoxycarbonyl, (di)-(allyl)amino carbonyl, (alkyl) arylamino carbonyl, aryl optionally substituted with a phenyl, monocyclic heteroaryl comprising 5, 6 or 7 carbon atoms, or oxazolium, or else with an 8 to 11 ring-membered bicyclic heteroaryl such as benzoimidazolium or benzoxazolium. The protected thiols can be synthesised via reactions known to those skilled in the art and described in the handbooks (i) Greene's Protective Groups in Organic Synthesis, Peter G M Wuts and Theodore W Greene, Wiley Science and (ii) Protecting groups by Philip J. Kocienski, 3rd ed.

Composition

The invention also relates to a cosmetic composition comprising, in an aqueous or aqueous-alcoholic cosmetically acceptable medium, one or more compounds of formula (II), as defined above.

In the compositions in accordance with the invention, the total concentration of compounds of formula (II) preferably ranges from 0.05 to 20% by weight, more preferentially from 0.1 to 15% by weight and even more preferentially from 0.25 to 10% by weight relative to the total weight of the composition.

The cosmetically acceptable medium preferably consists of water, and optionally one or more cosmetically acceptable solvents such as alcohols, esters, ketones or cyclic volatile silicones, these solvents preferably being $C_1$-$C_4$ alcohols.

The composition may also contain various adjuvants conventionally used in hair dye compositions, such as anionic, cationic, non-ionic, amphoteric or zwitterionic surfactants or mixtures thereof, anionic, cationic, non-ionic, amphoteric or zwitterionic polymers or mixtures thereof, inorganic or organic thickeners, and in particular anionic, cationic, non-ionic and amphoteric polymeric associative thickeners, antioxidants, penetrants, sequestrants, fragrances, buffers, dispersants, conditioning agents, for instance volatile or non-volatile, modified or unmodified silicones such as amino silicones, film-forming agents, ceramides, preserving agents, opacifiers and conductive polymers.

Needless to say, those skilled in the art will take care to select the adjuvant(s) such that the advantageous properties intrinsically associated with the composition in accordance with the invention are not, or are not substantially, adversely affected by the envisaged addition(s).

The above adjuvants are generally present in an amount, for each of them, of between 0.01 and 20% by weight, relative to the weight of the composition.

The pH of the composition in accordance with the invention is generally between 3 and 12 approximately and preferably between 5 and 11 approximately. It may be adjusted to the desired value by means of acidifying or alkalinizing agents which are customarily used, or alternatively using standard buffer systems.

Among the acidifying agents, mention may be made, by way of example, of inorganic or organic acids other than dicarboxylic acids, such as hydrochloric acid, ortho-phosphoric acid, sulfuric acid, carboxylic acids such as acetic acid, tartaric acid, citric acid or lactic acid, and sulfonic acids.

Among the alkalinizing agents, mention may be made, by way of example, of aqueous ammonia, alkali metal carbonates, alkanolamines such as mono-, di- and triethanolamines and their derivatives, sodium hydroxide or potassium hydroxide, and the compounds of formula:

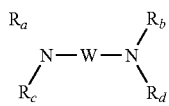

in which W is a propylene residue optionally substituted with a hydroxyl group or a $C_1$-$C_4$ alkyl radical; and Ra, Rb, Rc and Rd, which may be identical or different, represent a hydrogen atom or a $C_1$-$C_4$ alkyl or $C_1$-$C_4$ hydroxyalkyl radical.

The cosmetic composition according to the invention may be present in a variety of forms, such as in the form of liquids, creams, gels, or any other form which is appropriate for carrying out the treatment of keratin fibres, and in particular of human hair.

Process

The invention relates to a process for treating keratin fibres, such as human keratin fibres and in particular the hair, comprising a step of applying the hair composition as defined above to said fibres.

The application of the composition is generally carried out at ambient temperature. However, it may be carried out at temperatures ranging from 20 to 180° C.

According to a first embodiment, the application of the composition containing the compound(s) of formula (II) to be keratin materials is carried out at the same time as a reducing agent.

The reducing agent is as previously defined.

The reducing agent can be added to the composition according to the invention just before the application of the composition, thus allowing application of the composition according to the invention and of the reducing agent simultaneously.

According to a second embodiment of the invention, the application of the reducing agent and the application of the composition according to the invention are carried out in two steps. Preferably, the application of the reducing agent is carried out after the application of the composition according to the invention.

According to a third embodiment, the process of the invention is carried out in the presence of an oxidizing agent post-treatment, when the composition already contains a reducing agent. In other words, according to this embodiment, one or more reducing agents are added to the composition according to the invention prior to use. This ready-to-use composition is applied to the keratin fibres. Then, in a second step, an oxidizing agent is applied to be keratin fibres.

According to a fourth embodiment, the composition according to the invention is applied to keratin materials, i.e. without reducing agent, and then in a second step, an oxidizing agent is applied to the treated fibres.

According to a fifth embodiment, the process comprises, prior to the application of the composition according to the invention, i.e. without reducing agent, a step of reduction by application of a composition comprising one or more agents for breaking keratin disulfide bonds, i.e. reducing agents.

Generally, the reducing agent is in a composition, termed reducing composition. The composition used for breaking the keratin disulfide bonds in the process according to the invention generally comprises one or more agents for breaking keratin disulfide bonds, chosen from thiolated reducing agents, nonthiolated organic reducing agents, inorganic or organic hydroxides, or precursors thereof.

The agent(s) for breaking keratin disulfide bonds generally represent from 0.1 to 50% and preferably from 2% to 10% by weight of the total weight of the reducing composition.

The pH of the reducing composition preferably ranges between 7 and 14.

Preferably, the pH ranges from 8 9.5, when the reducing composition comprises a thiolated reducing agent.

Preferably, the pH ranges from 11 to 14, when the reducing composition comprises an alkaline agent of hydroxide type.

The reducing composition may be in liquid form or in thickened form. It may be applied from a heating bag, by brush or directly from the tube.

Generally, the reducing composition is left on for 5 minutes to 1 hour, preferably for 10 minutes to 30 minutes. After the optional leave-on time, the hair may be rinsed, preferably with water.

Generally, the oxidizing agent is in a composition, termed oxidizing composition. The oxidizing composition used in the process according to the invention generally comprises one or more oxidizing agents chosen from hydrogen peroxide, alkali metal bromates, polythionates, persalts such as perborates, percarbonates and persulfates, adsorbed or non-adsorbed metal salts, and enzymes of the 2-electron oxidase family.

Preferably, the oxidizing agent is hydrogen peroxide in the form of aqueous hydrogen peroxide solution, or alkali metal bromates.

Even more preferentially, the oxidizing agent is hydrogen peroxide in the form of aqueous hydrogen peroxide solution.

The oxidizing agent(s) generally represent(s) from 0.1 to 8% and preferably from 0.2 to 5% by weight relative to the total weight of the oxidizing composition.

Preferably, when the oxidizing agent is hydrogen peroxide in aqueous solution, the oxidizing composition used in the process according to the invention contains at least one stabilizer of aqueous hydrogen peroxide solution.

Mention may be made in particular of alkali metal or alkaline-earth metal pyrophosphates, such as tetrasodium pyrophosphate, alkali metal or alkaline-earth metal stannates, phenacetin or oxyquinoline acid salts, for instance oxyquinoline sulfate (8-hydroxyquinoline sulfate). Even more advantageously, use is made of at least one stannate optionally in combination with at least one pyrophosphate.

The stabilizer(s) of aqueous hydrogen peroxide solution generally represent from 0.0001% to 5% by weight and preferably from 0.01% to 2% by weight relative to the total weight of the oxidizing composition.

The oxidizing composition may be in liquid form or in the thickened form.

Generally, the pH of the oxidizing composition ranges from 1 to 13 and preferably from 1.5 to 8.

When the oxidizing agent is hydrogen peroxide, the pH of the oxidizing composition preferentially ranges from 1.5 to 5.

Generally, the oxidizing composition is left on for 5 minutes to 1 hour, preferably for 10 minutes to 30 minutes.

The compositions according to the invention can be applied to dry or wet hair.

According to another embodiment, the composition according to the invention has a pH of between 5 and 8. This pH can be described according to the invention as neutral. In this medium, the compound of formula (II) according to the invention has a hydrophobic nature owing to the ionic bond present between the group X and the group Y. The compound of formula (II) is then in the cyclic form.

When such a composition is applied to the fibres, it then confers on the grafted fibres a hydrophobic nature which is particularly desired for the disentangling, softness and feel of said fibres.

The latter can subsequently undergo a basic treatment. It is, for example, possible to envision washing the fibres using a basic shampoo, having, for example, a pH above 8.

This treatment then makes it possible to open the ring present in the compounds of formula (II), the latter thus having an extended chain comprising a hydrophilic entity at its end. The presence of such a structure brings about an increase in the hydrophilic nature of the fibre.

This more hydrophilic nature has the advantage of facilitating cleansing of the fibres.

The entire advantage of the invention can be seen here. Said invention aims essentially to modulate the physico-chemical properties of the fibres grafted by means of acid-base treatments.

Use

Another subject of the invention is the use of the composition for the cosmetic treatment of keratin fibres, such as human keratin fibres and in particular the hair.

Kit

Another subject of the invention is a multi-compartment device or kit, comprising:
- a first compartment comprising a composition according to the invention as defined above,
- a second compartment comprising an oxidizing composition.

Another subject of the invention is a second multi-compartment device or kit, comprising:
- a first compartment comprising a composition comprising one or more reducing agents,
- a second compartment comprising a composition according to the invention as defined above, and
- a third compartment comprising an oxidizing composition.

The invention will be illustrated more fully with the aid of the non-limiting example that follows.

EXAMPLES

In the following examples, all the amounts are shown as percentage by weight of active material (AM), relative to the total weight of the composition.

Synthesis of Compound 1:

The compound having the following formula is a precursor compound of a compound of formula (I) described above.

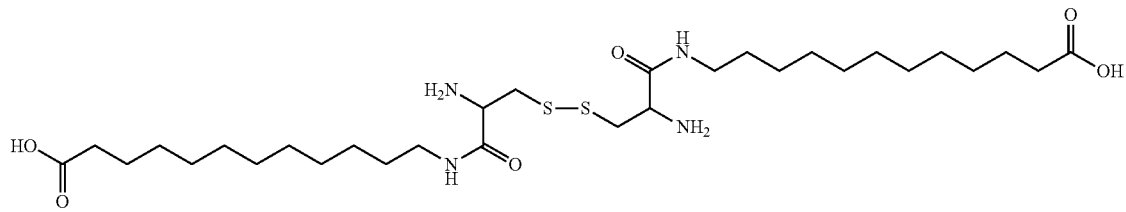

precursor of compound 81

1. Synthesis Scheme:

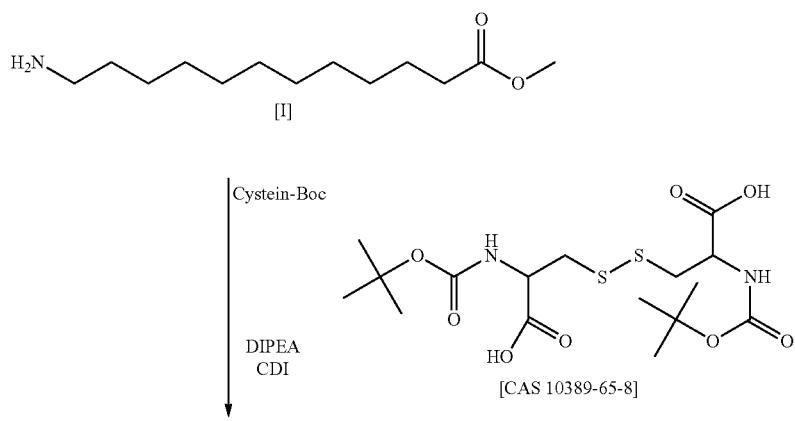

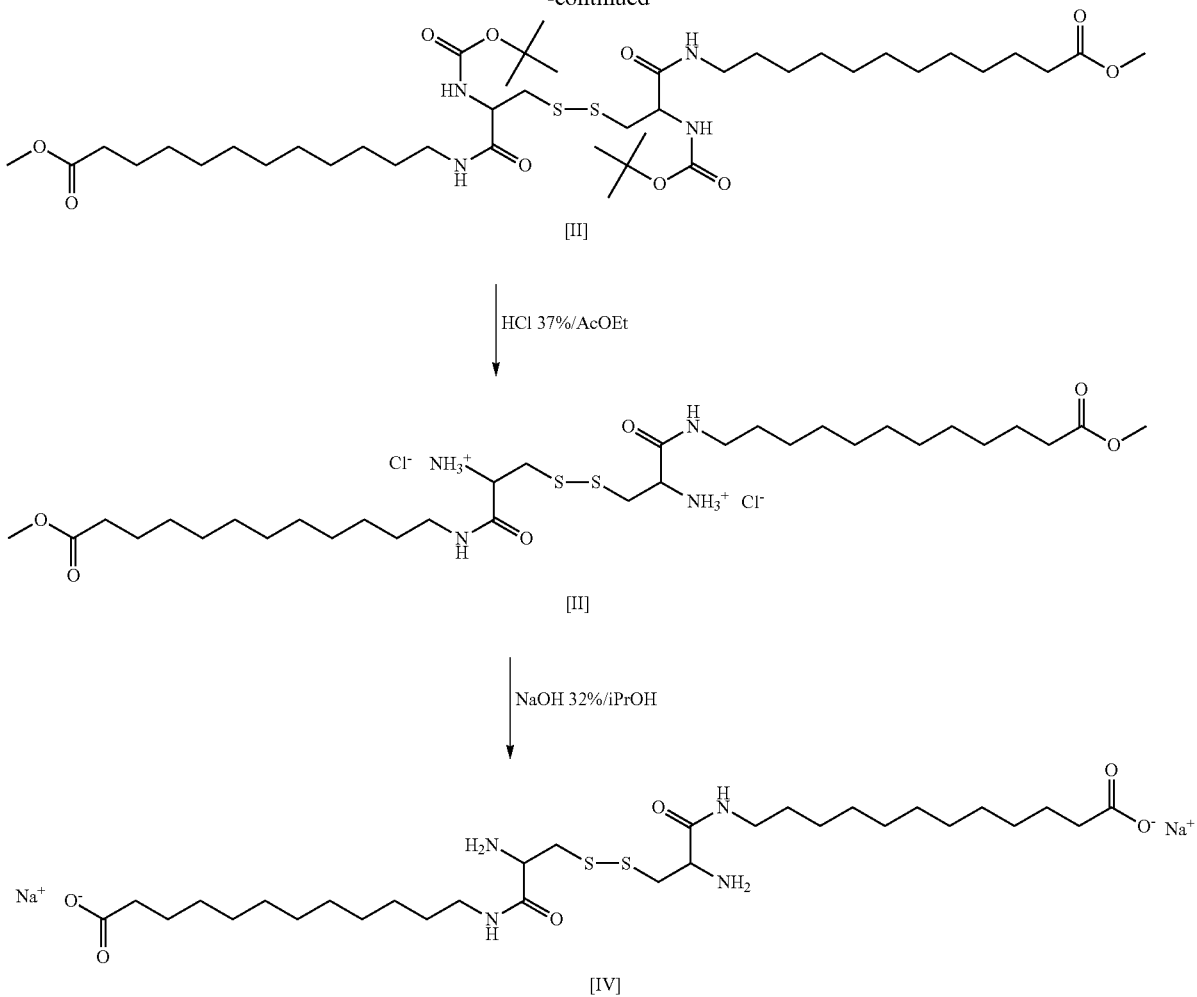

Step 1

The handling is carried out in a three-necked flask provided with magnetic stirring, a condenser, a thermometer and nitrogen inerting. The compound [CAS 10389-65-3] (1.05 g) is dissolved in dichloromethane (10 ml) and placed in the three-necked flask. Carbonyldimidazole (0.916 g) is added and left to stir for 5 min at ambient temperature. The compound II is solubilised in dichloromethane (6 ml), in an Erlenmeyer flask. This solution is added dropwise to the reaction mixture in the three-necked flask. The reaction mixture is left to react for 12 hours and then washed with water (3×10 ml). The organic phase is dried with sodium sulfate, filtered and then evaporated. A yellow powder is obtained. The analyses comply with what is expected (compound II).

Step 2

The compound II, ethyl acetate (30 ml) and 37% hydrochloric acid (2 ml) are added to a three-necked flask provided with magnetic stirring, a condenser and a thermometer. The reaction mixture is refluxed for 6 hours and then cooled. The reaction mixture is filtered, and the solid is washed with ethyl acetate (3×20 ml) and then air-dried. A yellow powder is obtained. The analyses comply with what is expected (compound III).

Step 3

The compound II, diisopropyl alcohol (30 ml) and sodium hydroxide (100 mg) are added to a three-necked flask provided with magnetic stirring, a condenser and a thermometer. The reaction mixture is refluxed for 6 hours and then cooled. The reaction mixture is added to diethyl ether, and the precipitate is filtered, washed with diethyl ether (3×50 ml) and then air-dried. A white powder is obtained. The analyses comply with what is expected (compound IV).

2. Application Protocol

The composition of formula A according to the invention and comparative composition of formula B are prepared according to the formulations of the table below:

Immediately after they have been prepared, the compositions are applied to natural 90% white hair in a proportion of 5 g of formula per 1 g of hair, at ambient temperature for 30 minutes. The locks are rinsed with water, wrung dry and then soaked for 5 minutes in a hydrogen peroxide solution (8 vol) a pH 3. The locks are then washed with shampoo (pH 6) and then dried under a hood for 30 minutes.

| (g %) | A | B |
|---|---|---|
| Hydroxyethylcellulose Natrosol 250MR | 0.72 | 0.72 |
| $C_8/C_{10}$ (50:50) Alkyl hydroxyethylcellulose CG 110 | 5 | 5 |
| Benzyl alcohol | 4 | 4 |

-continued

| (g %) | A | B |
|---|---|---|
| Polyethylene glycol 400 | 4 | 4 |
| Compound 81 | 1.5 | — |
| L'Oréal Dulcia Vital 2-force1 ® (thioglycolic acid at 9%) | 5 | 5 |
| Water | qs for 100 | qs for 100 |
| pH | 8.5 | 8.5 |

3. Shampooing Protocol

The lock is taken in the hand containing 0.4 g/g of lock of "Ultra doux à la camomille et miel de Fleurs®" [Ultra soft with camomile and flower honey] shampoo and the lock is passed between the fingers ten times to simulate shampooing. The lock is then rinsed with water at ambient temperature for 15 seconds.

A control lock is prepared using composition B, as described above. This lock corresponds to an embrittled hair and serves as a comparison for the tests.

4. Methods for Evaluating the Locks of Hair 4.1. Microscopy Studies

Several hairs extracted from the locks are fixed for characterisation of the hydrophobic forces using an atomic force microscope (AFM).

The AFM is capable of measuring the interaction of a microscopic probe with a surface. There is a correlation, described in the scientific literature, between the adhesion force measured by the AFM and the hydrophobic nature of the hair surface in an aqueous medium. The greater the interaction between an AFM probe (with a hydrophobic functionalisation) and the hair surface, the more hydrophobic the hair surface is.

Several cycles of approach and separation of this tip are carried out on all the samples. "Force curve" measurements are thus carried out. On the basis of these curves, adhesion values are obtained as a function of the pH of the medium. The method is detailed in the publications J. of Phys.: Conf. Ser.s 100, 052034 (2008) and *Cosmetics & Toiletries*, 101, 37, (1986).

In these experiments, the pHs of the solutions are 7 for the neutral solution, and the spontaneous pH of sodium hydroxide, i.e. approximately 10, for the basic solution.

The experiment is carried out on individual hairs (three hairs) and zones of 10×10 μm.

4.2 Wettability Test (Wilhelmy Balance)

The technique for measuring wettability consists in immersing a piece of hair vertically in a container of water and in measuring, using a tensiometer, the force generated by the displacement of the hair fibre during the immersion (wetting force) and during the withdrawal from the water. This force varies according to the affinity of the hair for the liquid and makes it possible to give an account of the surface condition of the fibre. The method is described in Cosmetics & Toiletries, 101, 37, (1986).

When the value of the wetting force is positive, this means that the hair is attracted by the water and has a more hydrophilic nature. When the value of the wetting force is negative, this means that the hair has a more hydrophobic nature.

4.3 Results 4.3.1 Atomic Force Microscopy

The results of the adhesion force (indication of the hydrophobic nature) on two different types of hair at different pH values are given in FIG. 1:
  comparative: treated with composition B represented on the left of the graph, and
  according to the invention: treated with composition A represented on the right of the graph.

It is observed that, in fact, the hydrophobic interaction force is greater for the hair treated with composition A using compound 81, under all the pH conditions. This effect confirms the grafting of compound 81 onto the hair and the effect of the exposed and uncurved hydrophobic chain in a neutral medium. Depending on the pH, it is possible to go from a hair where these interactions are less in a basic (more hydrophilic) medium to a hair where these interactions are exacerbated in a neutral (more hydrophobic) medium. The results show mainly that this effect can be modulated and, in addition, is reversible.

4.3.2 Wettability Test (Wilhelmy Balance)

Figure 2:
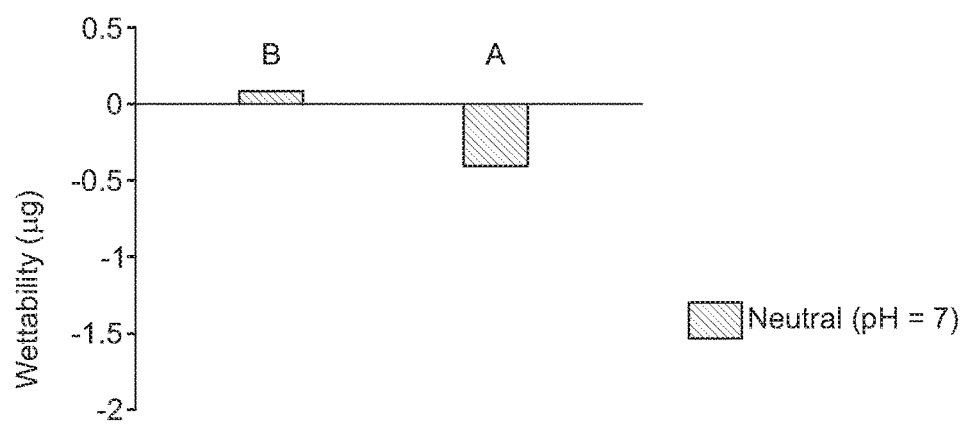
FIG. 2 illustrates results of wettability on various types of hair at different pH values: results obtained for comparative composition B are represented on the left of the figure, while the results obtained for composition A according to the invention are represented on the right of the figure.

The results of the wettability on the various types of hair at different pH values are given in FIG. 2. The results obtained for comparative composition B are represented on the left of the figure, while the results obtained for composition A according to the invention are represented on the right of the figure.

An effect similar to those obtained with the AFM is noted. The hair treated with the composition according to the invention becomes more hydrophobic than the hair treated with composition B. The hydrophobic nature of the surface of the hair is increased in all cases after the treatment step.

The invention claimed is:

1. A cosmetic composition comprising, in an aqueous or aqueous-alcoholic cosmetically acceptable medium, one or more compounds chosen from the following compounds:

Compound 1

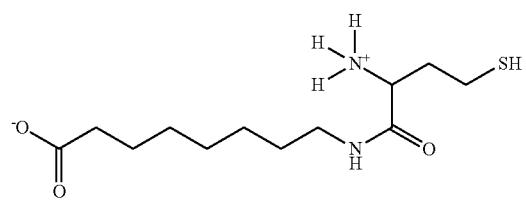

Compound 2

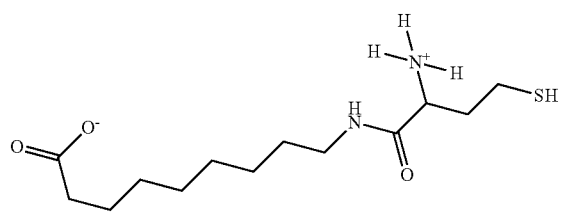

-continued
Compound 3
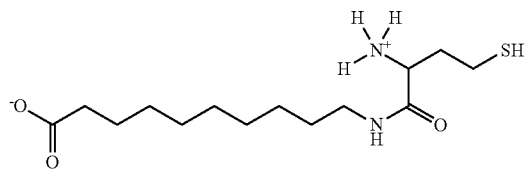
Compound 4
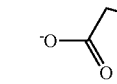
Compound 5
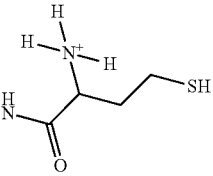
Compound 6
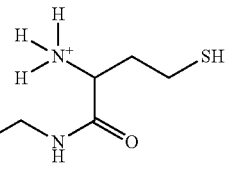
Compound 7
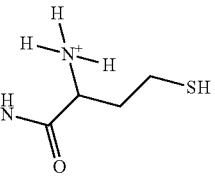
Compound 8
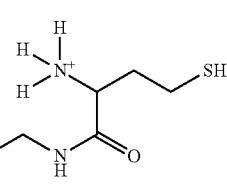
Compound 9

-continued
Compound 10
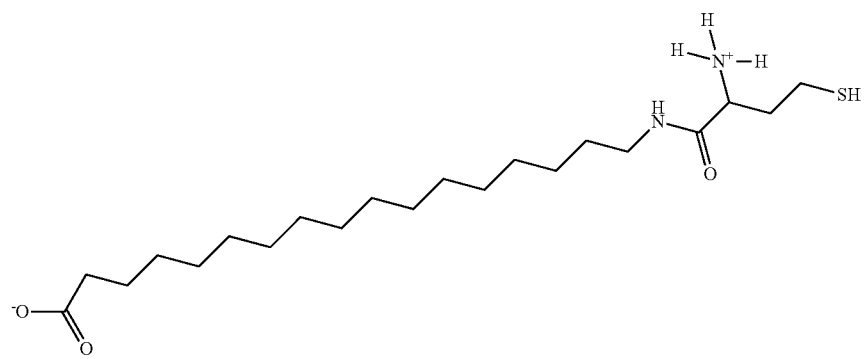
Compound 11
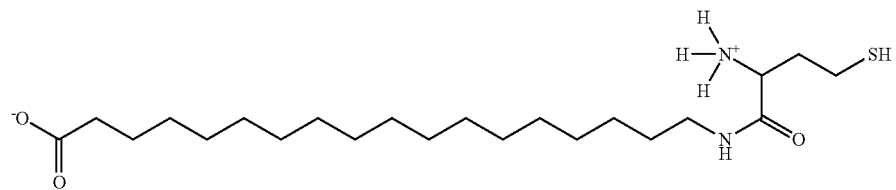
Compound 12
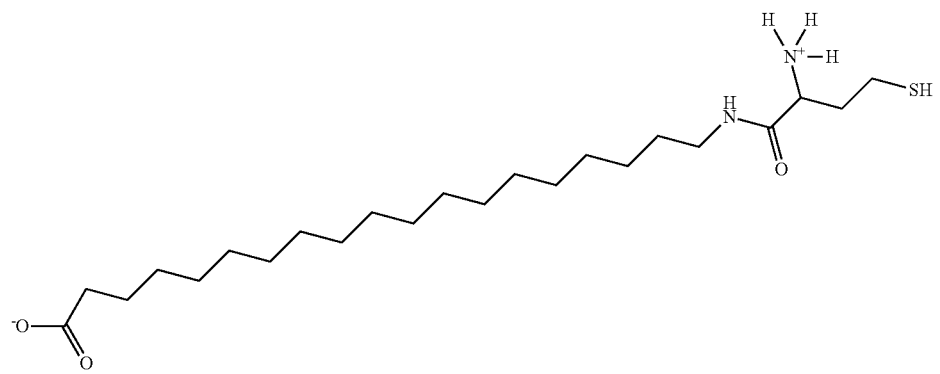
Compound 13
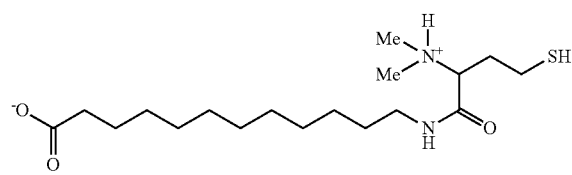
Compound 14
Compound 15
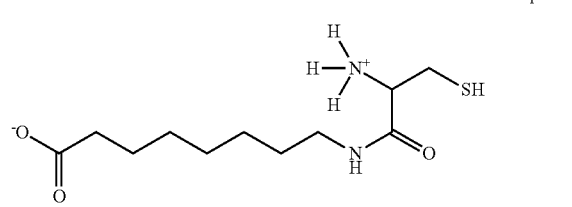
Compound 16
Compound 17
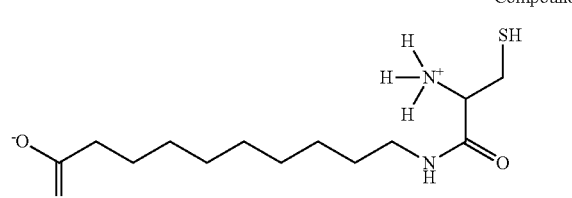
Compound 20
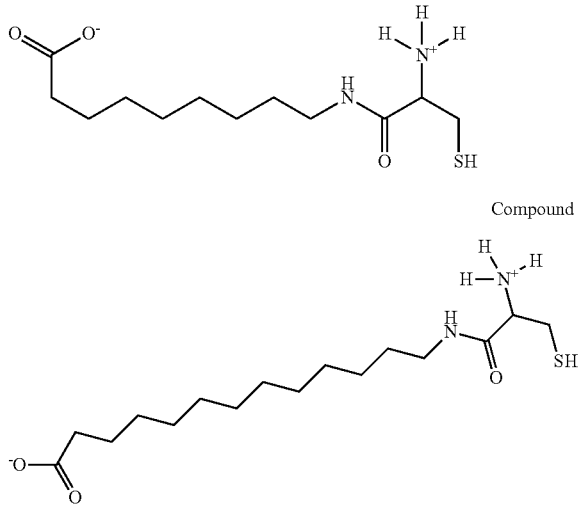

-continued
Compound 21
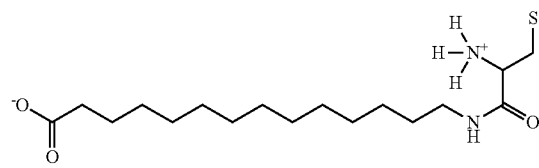
Compound 22
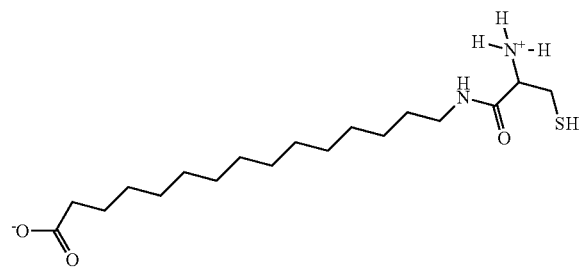
Compound 23
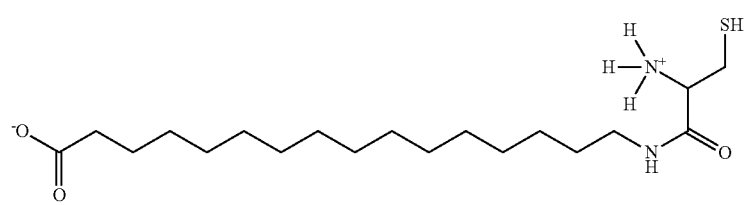
Compound 24
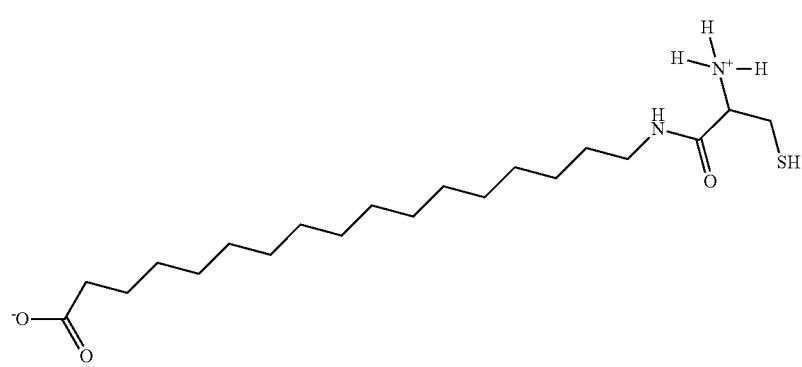
Compound 25
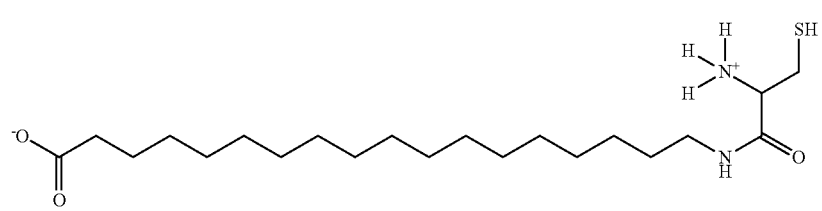
Compound 26
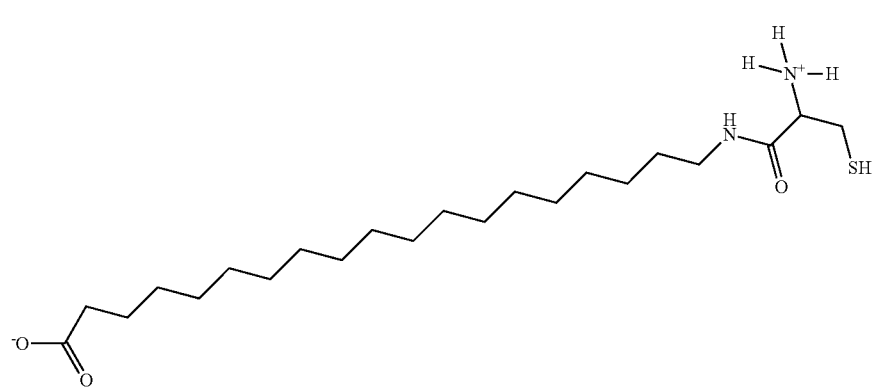
Compound 27
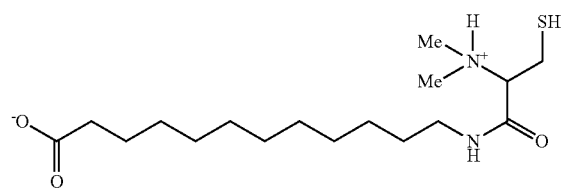
Compound 28
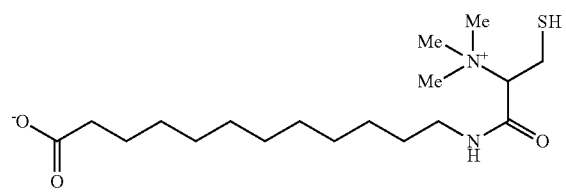

Compound 29
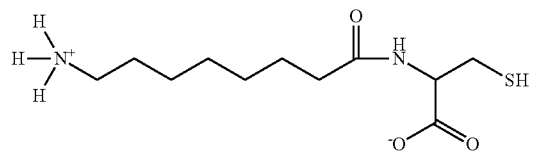
Compound 30
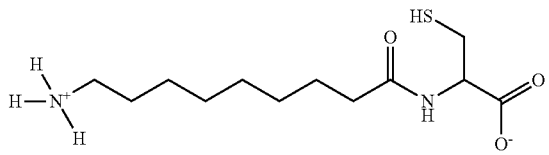
Compound 31
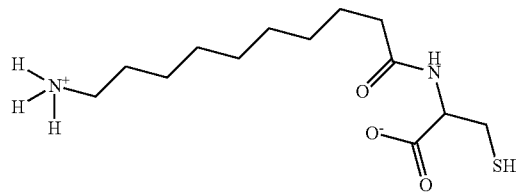
Compound 32
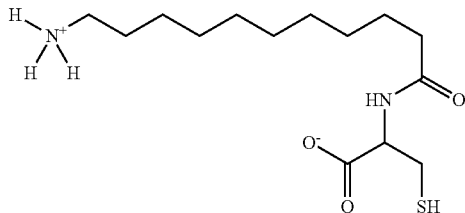
Compound 33
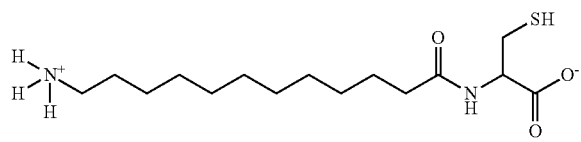
Compound 34
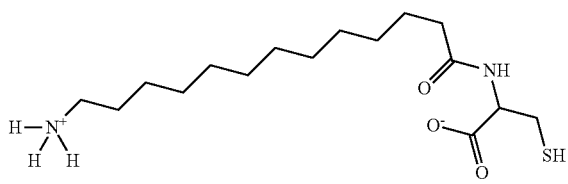
Compound 35
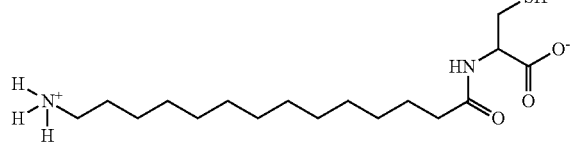
Compound 36
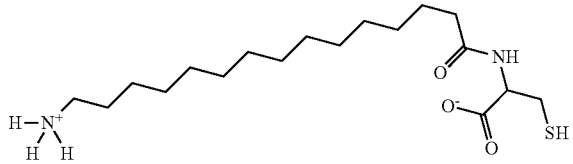
Compound 37
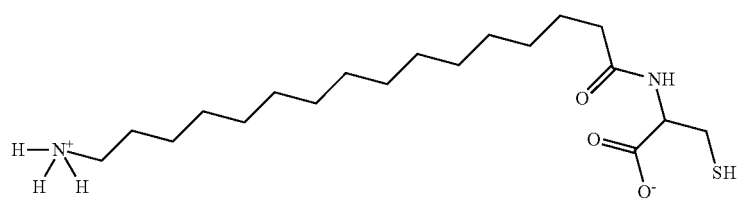
Compound 38
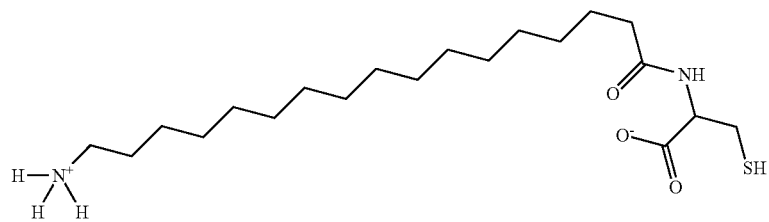
Compound 39
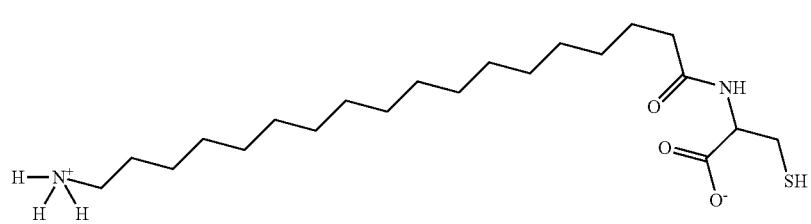

-continued
Compound 40
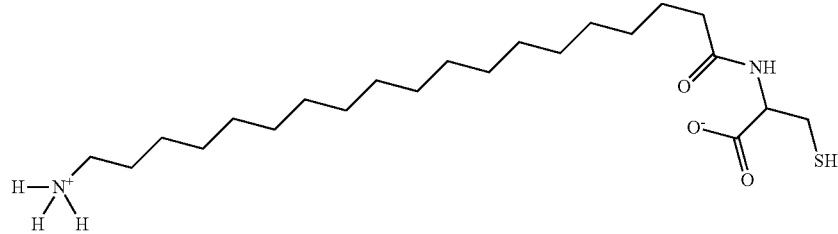
Compound 41
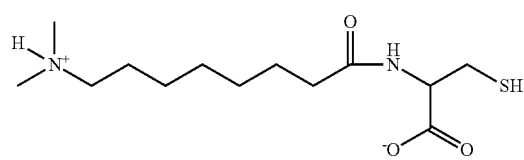
Compound 42
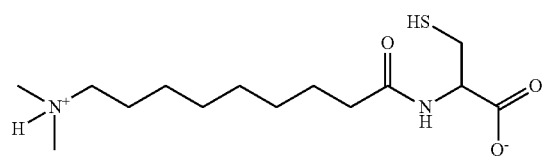
Compound 43
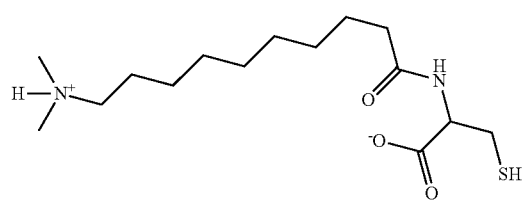
Compound 44
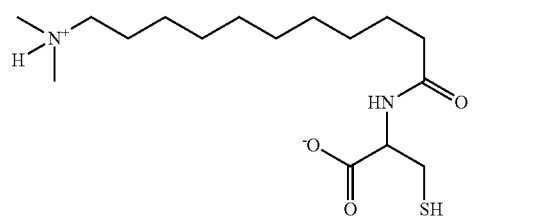
Compound 45
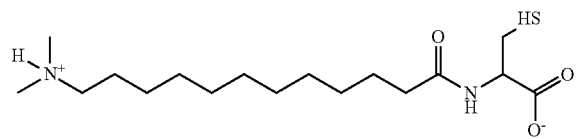
Compound 46
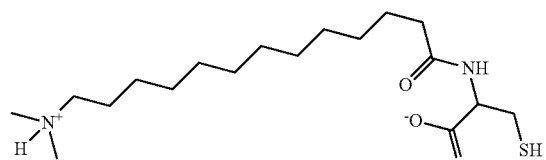
Compound 47
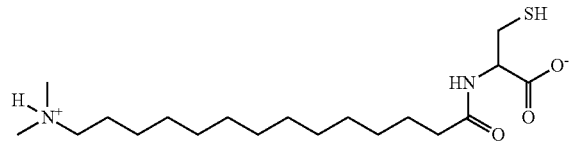
Compound 48
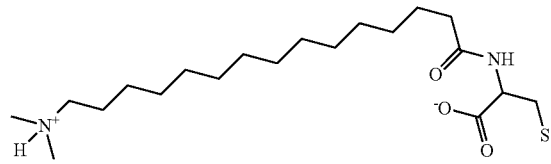
Compound 49
Compound 50
Compound 51
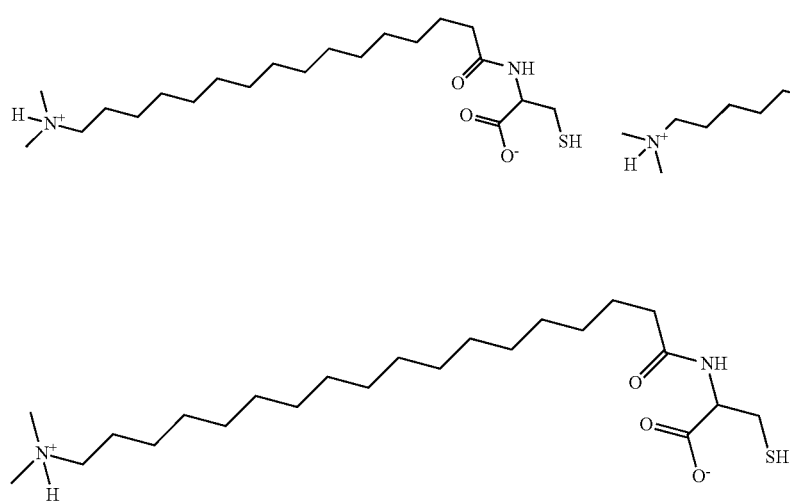

-continued
Compound 52
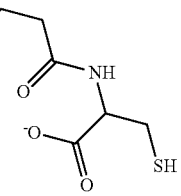
Compound 53
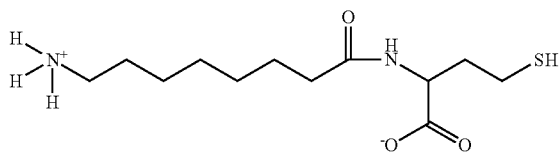
Compound 54
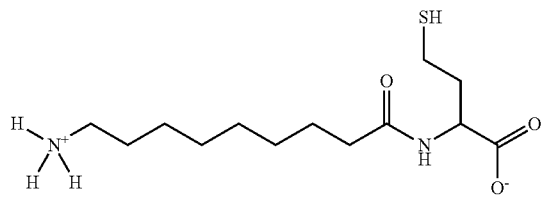
Compound 55
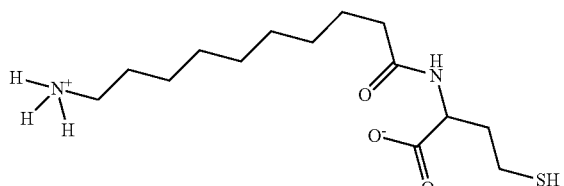
Compound 56
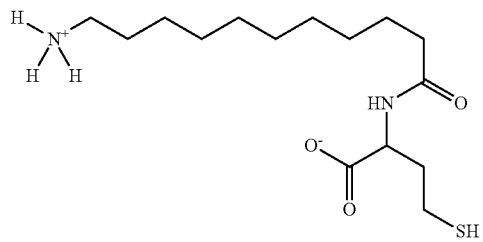
Compound 57
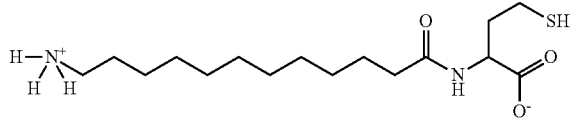
Compound 58
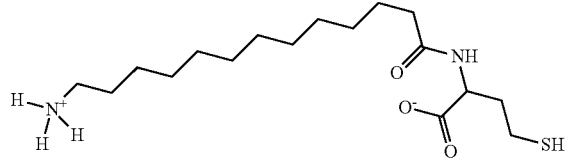
Compound 59
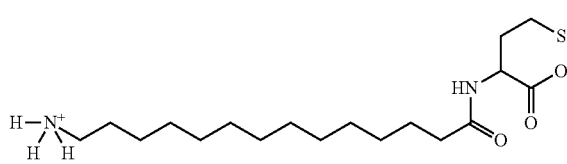
Compound 60
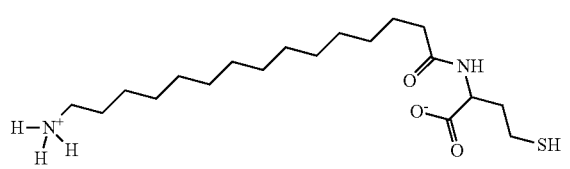
Compound 61
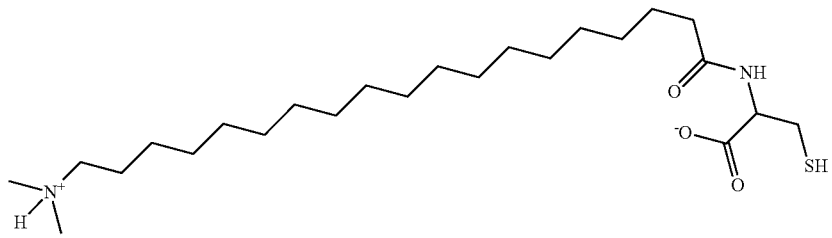
Compound 62
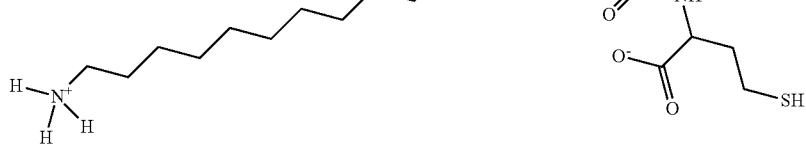

-continued
Compound 63
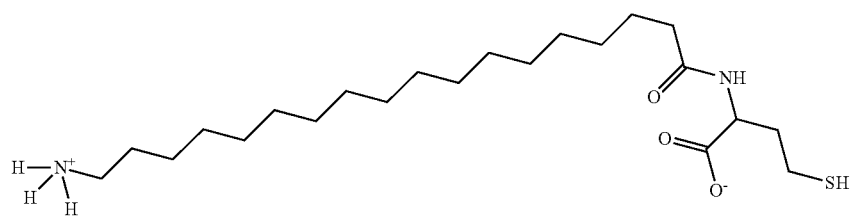
Compound 64
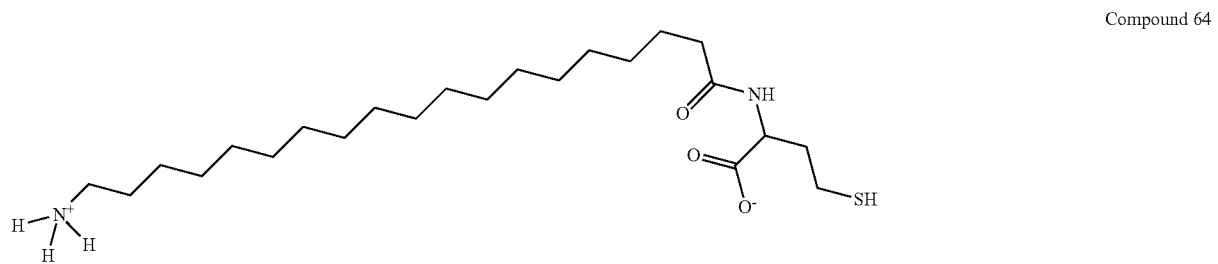
Compound 65 Compound 66
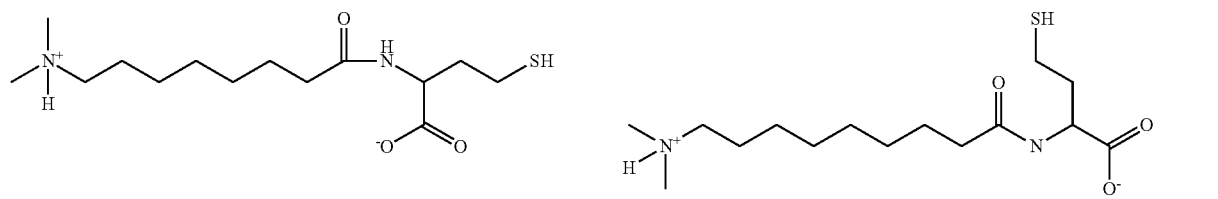
Compound 67 Compound 68
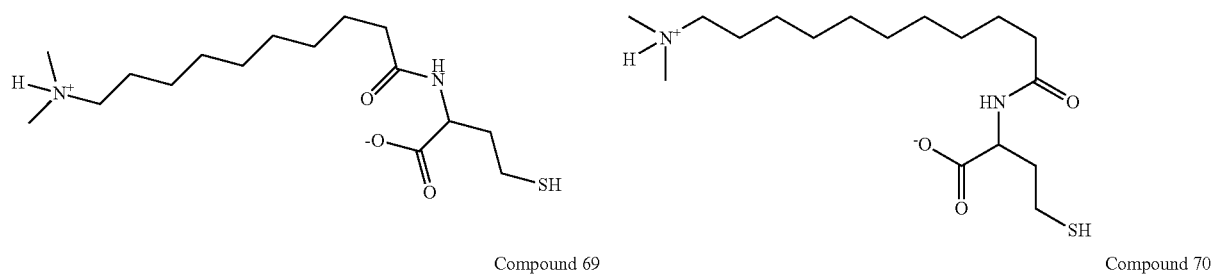
Compound 69 Compound 70
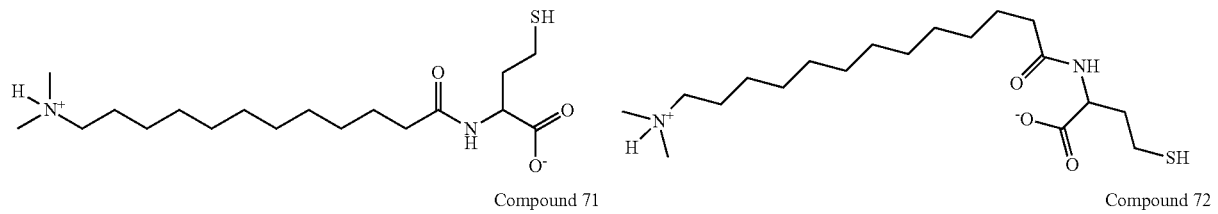
Compound 71 Compound 72
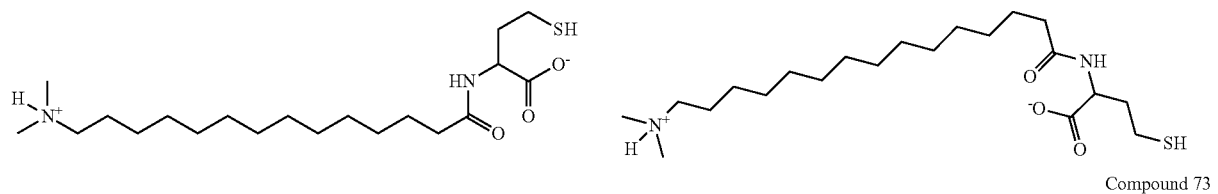
Compound 73
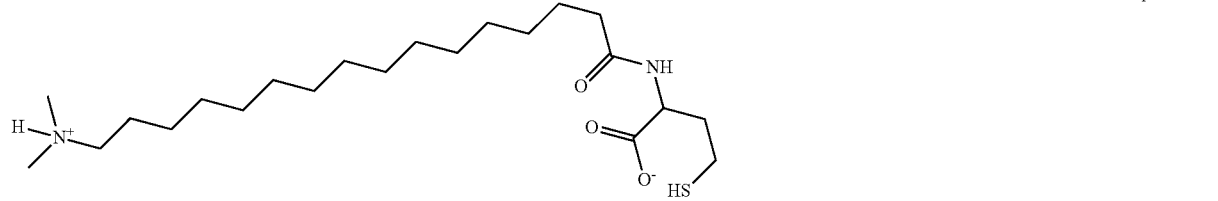

-continued
Compound 74
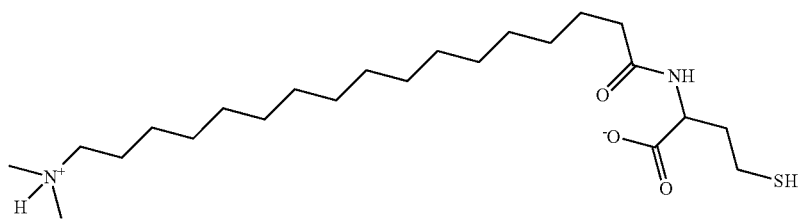
Compound 75
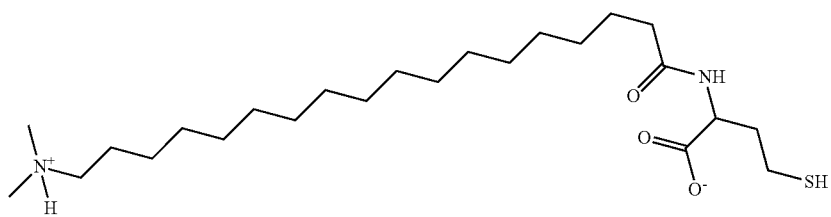
Compound 76
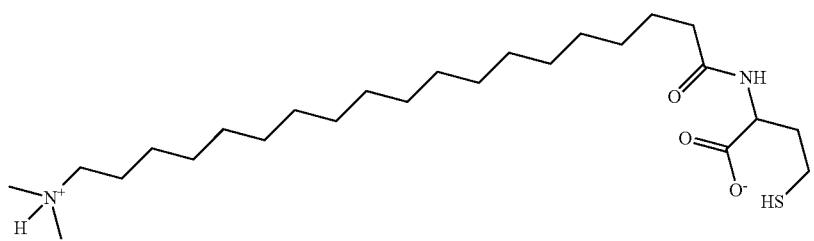
Compound 77
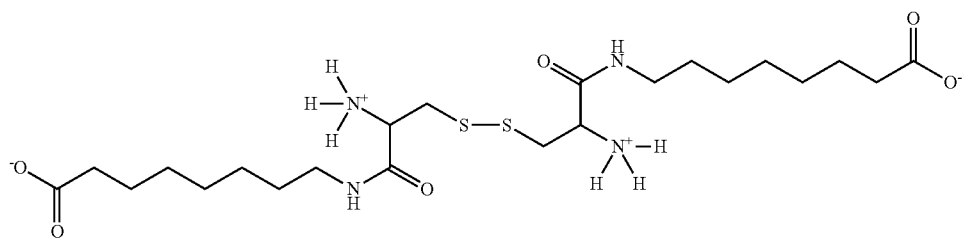
Compound 78
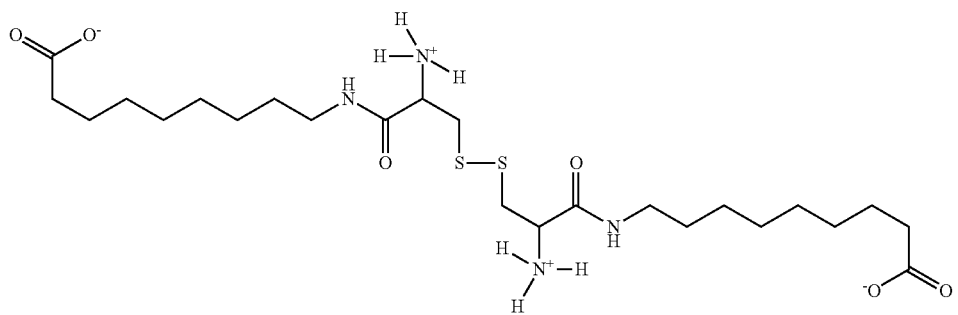
Compound 79
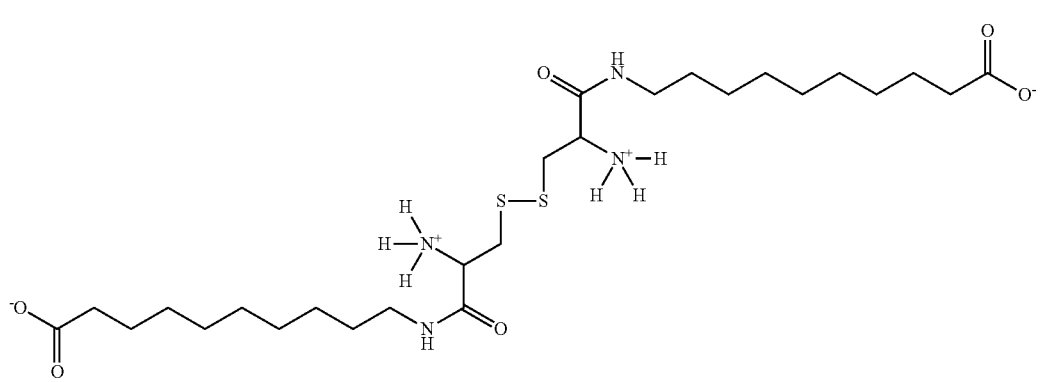

Compound 80
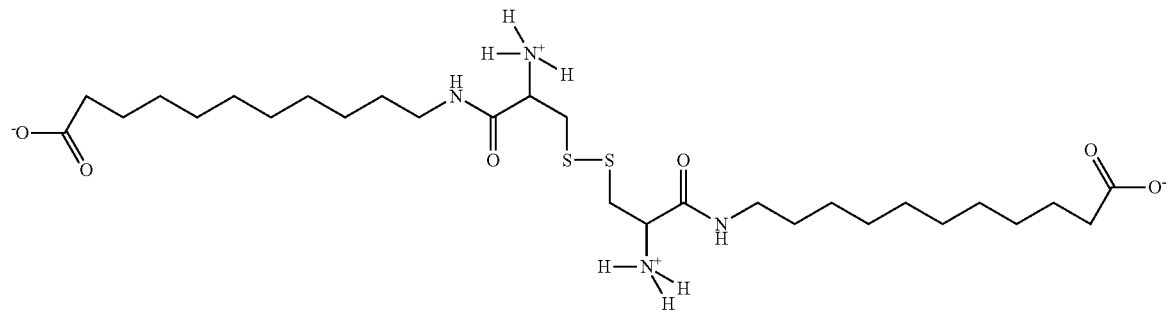
Compound 81
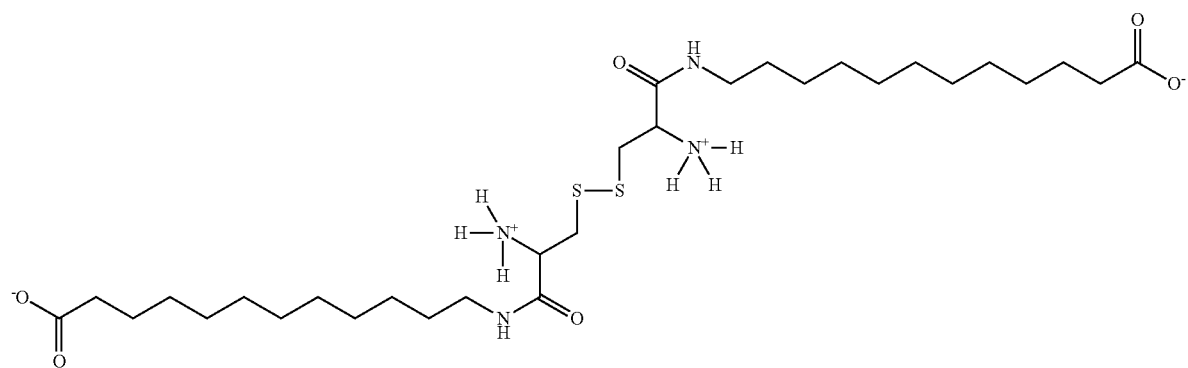
Compound 82
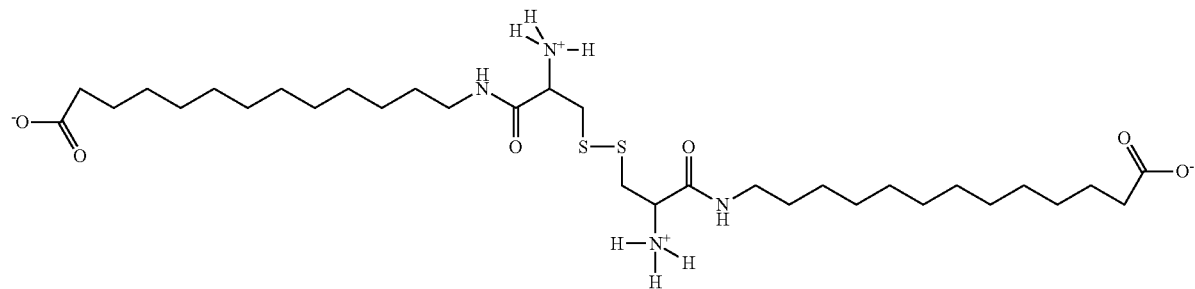
Compound 83
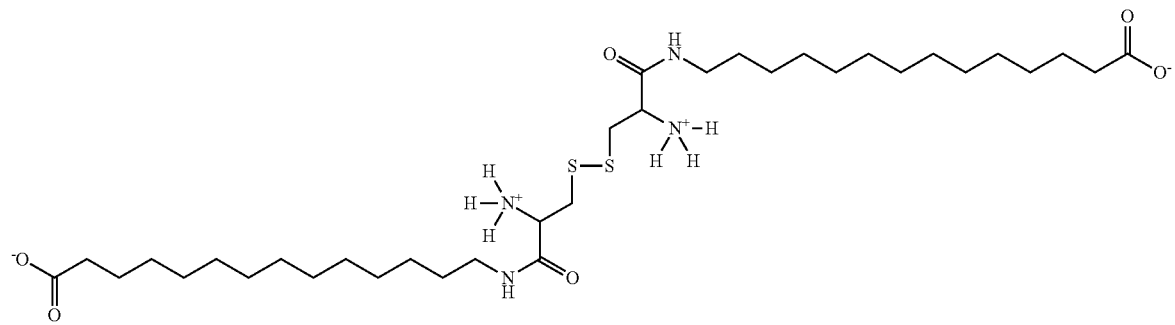

-continued
Compound 84
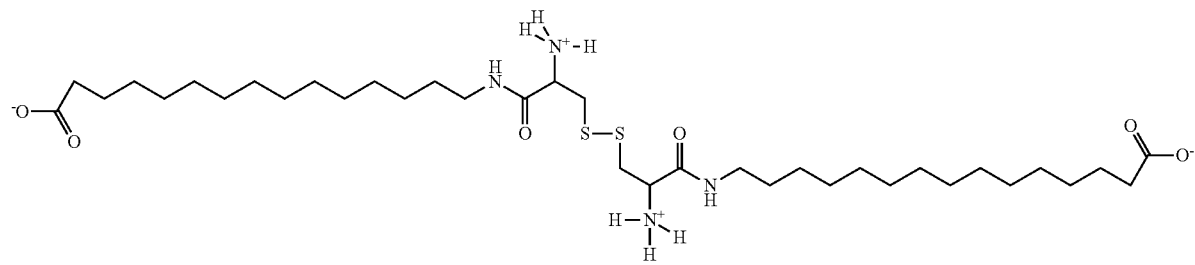
Compound 85
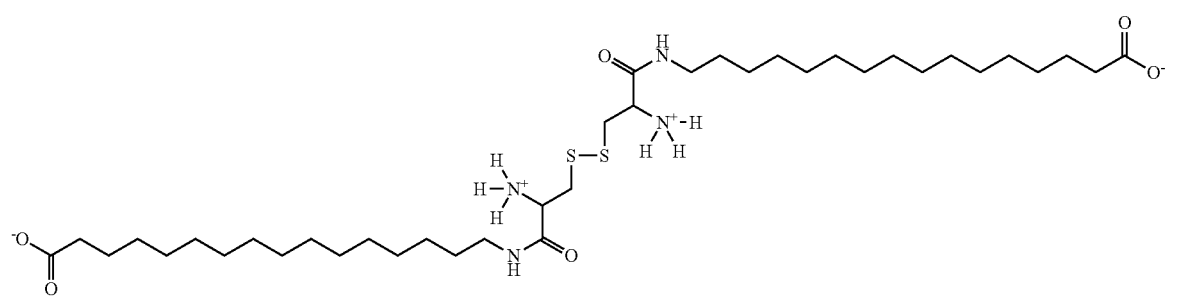
Compound 86
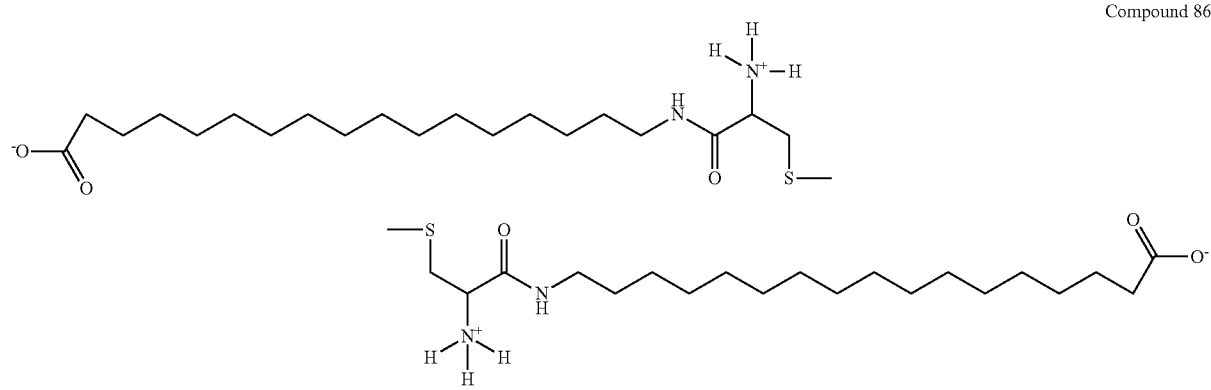
Compound 87
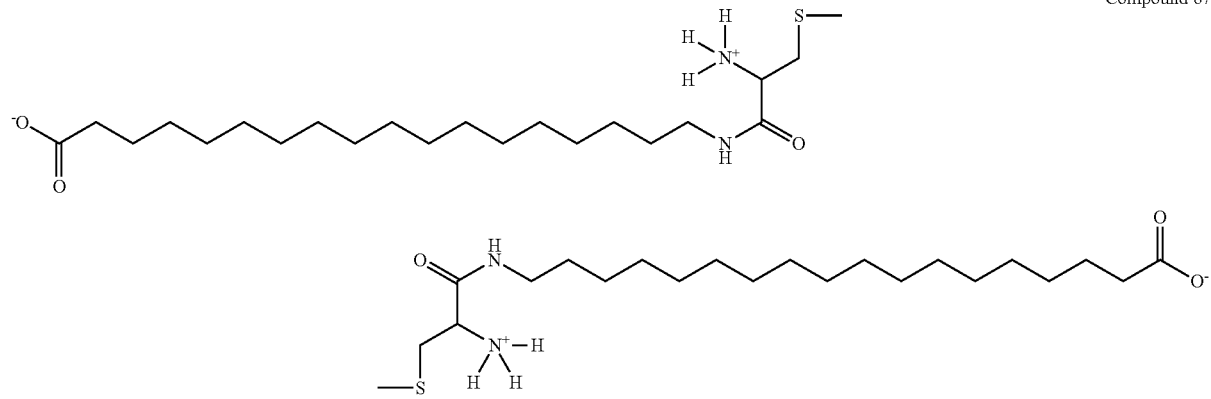
Compound 88
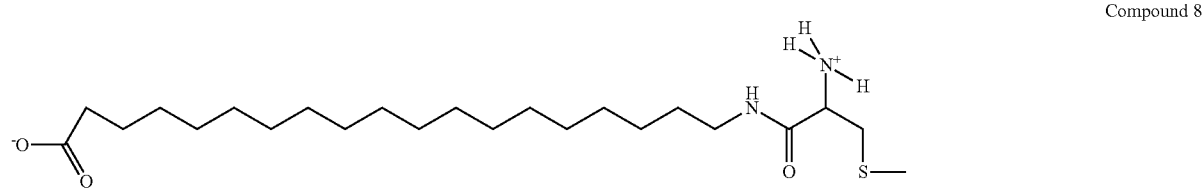

-continued
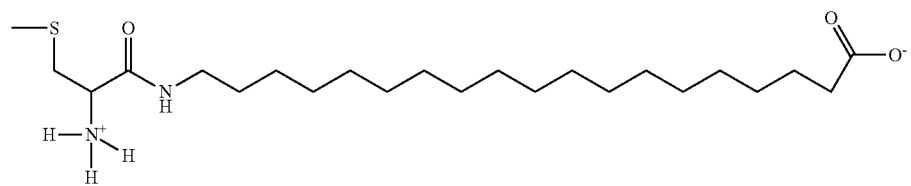
Compound 89
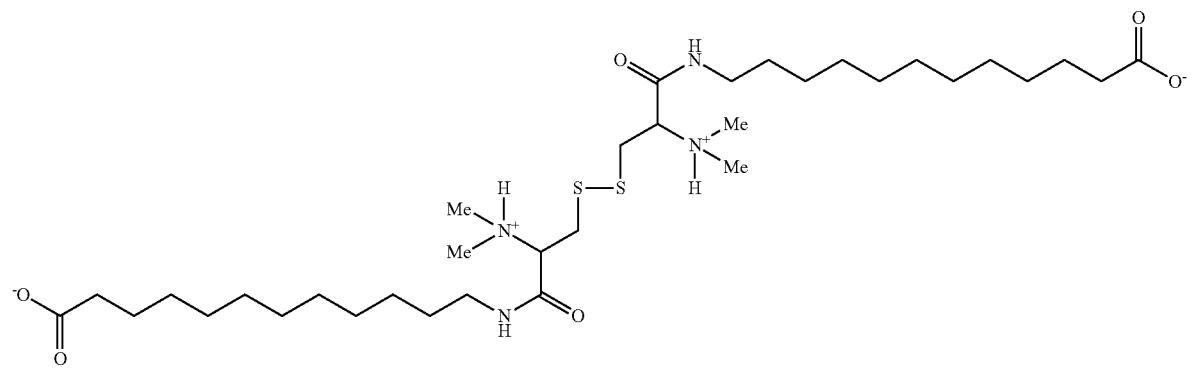
Compound 90
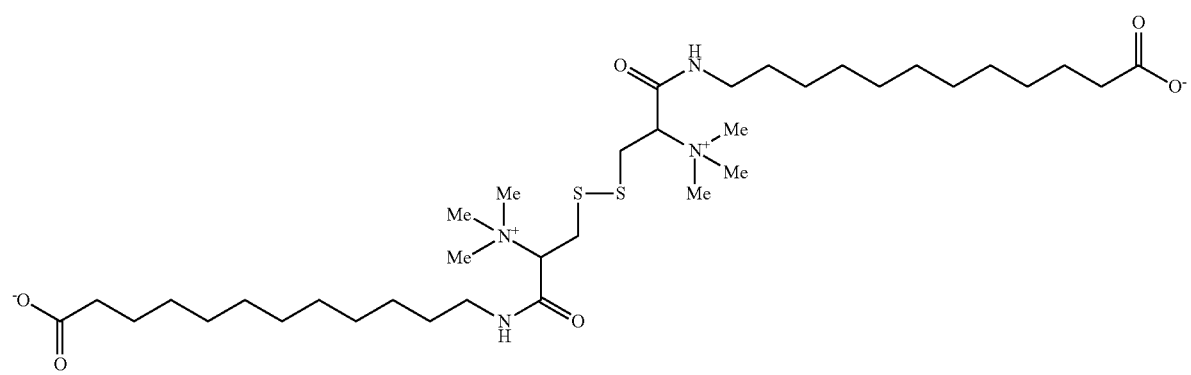
Compound 91
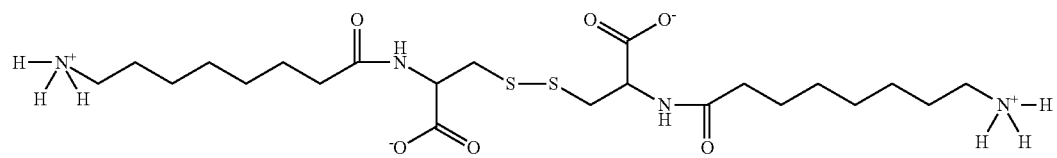
Compound 92
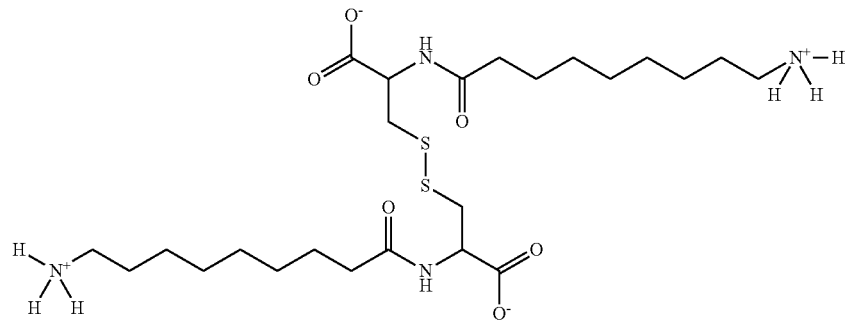

-continued
Compound 93
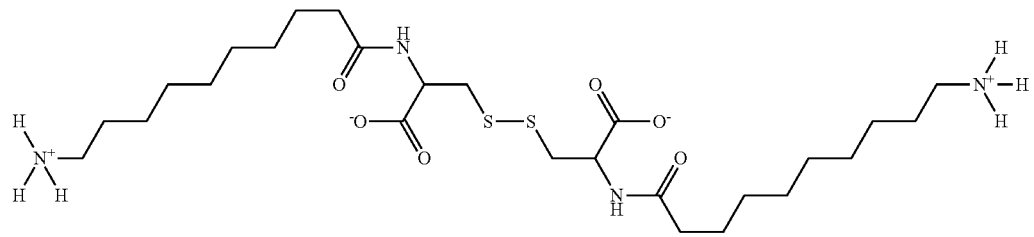
Compound 94
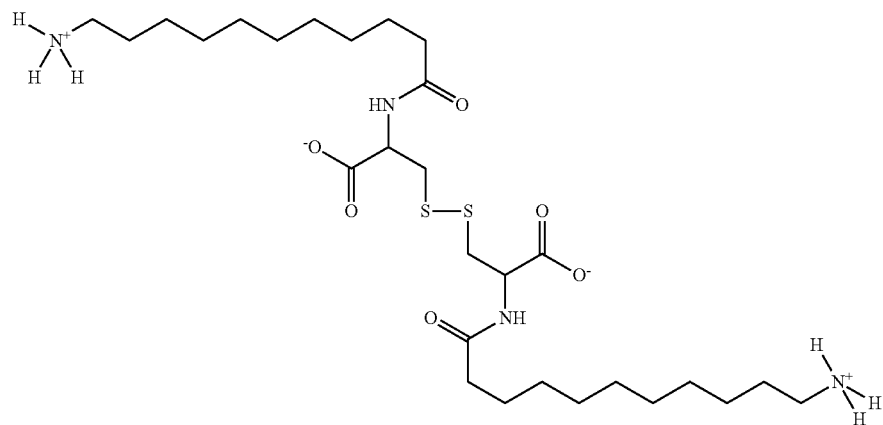
Compound 95
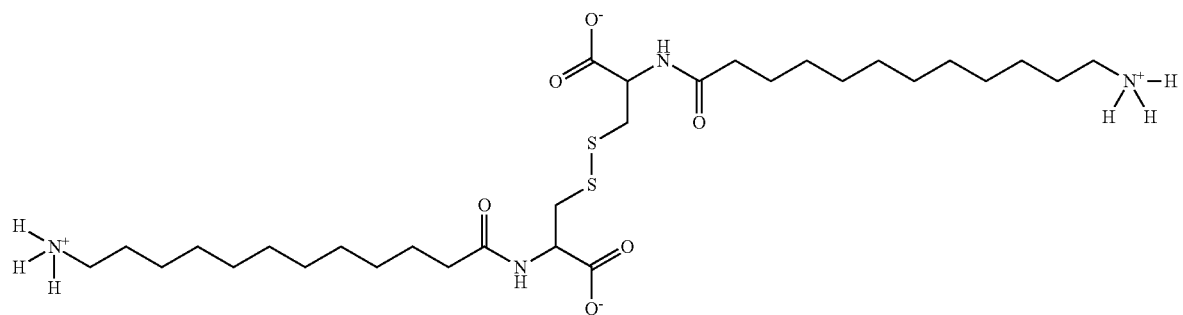
Compound 96
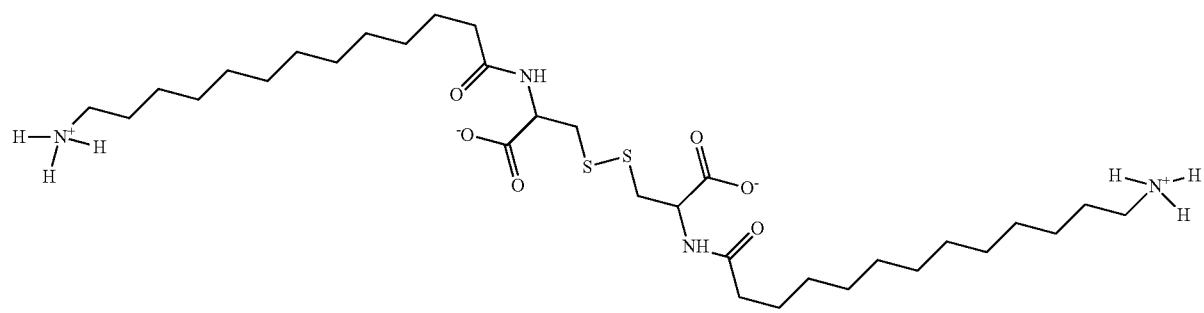

-continued
Compound 97
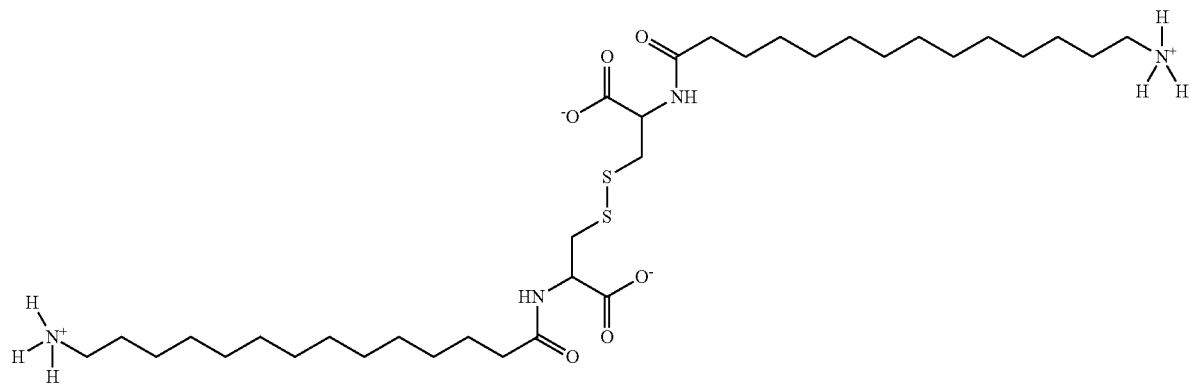
Compound 98
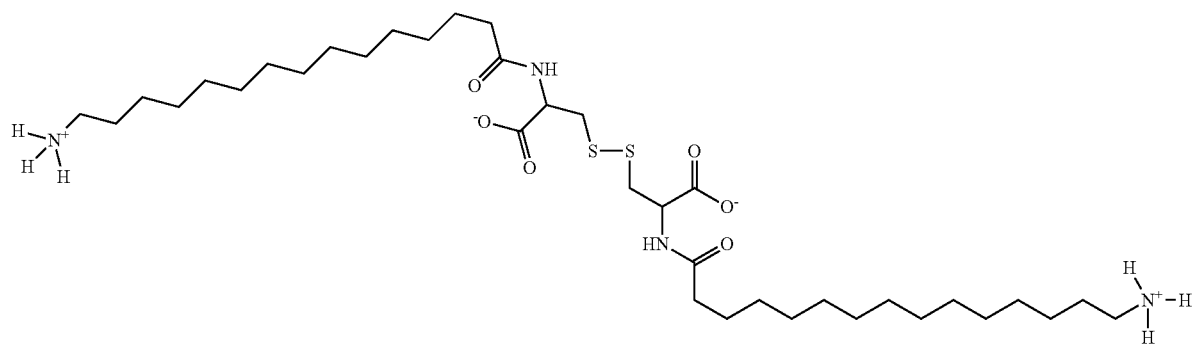
Compound 99
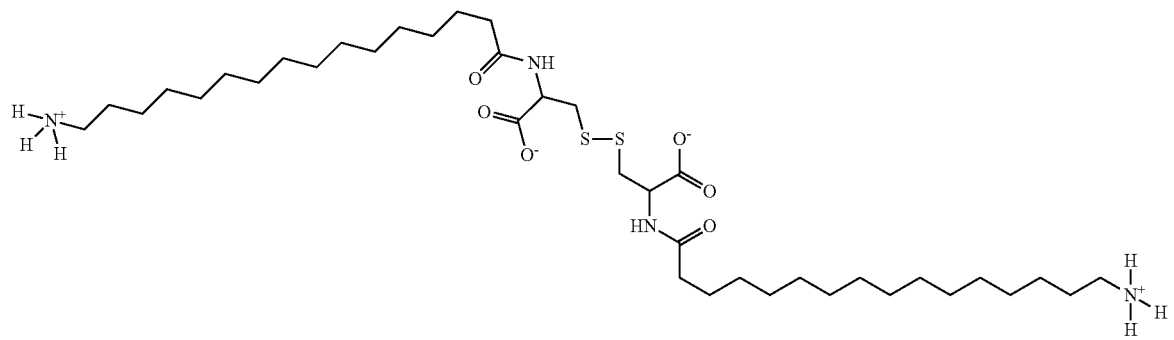
Compound 100
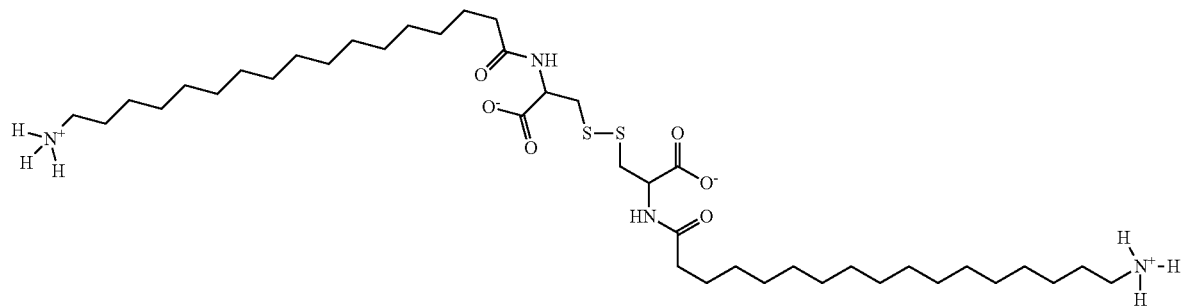

-continued
Compound 101
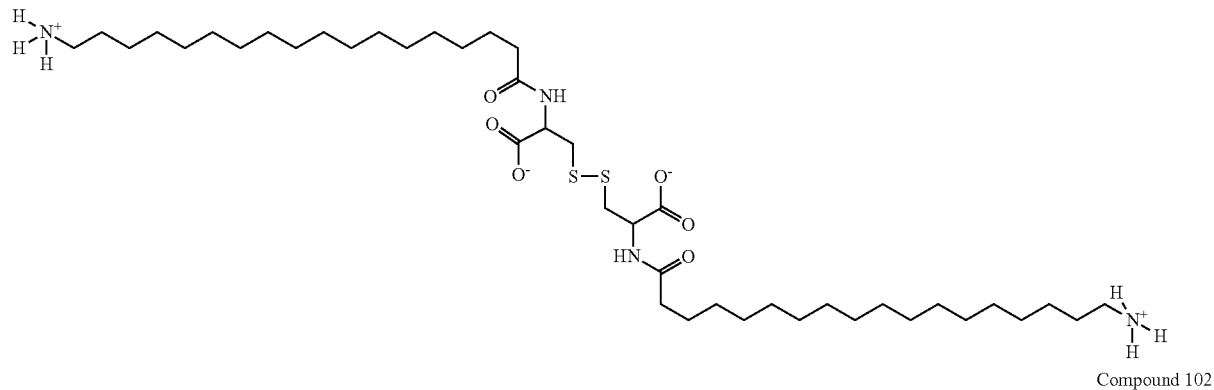
Compound 102
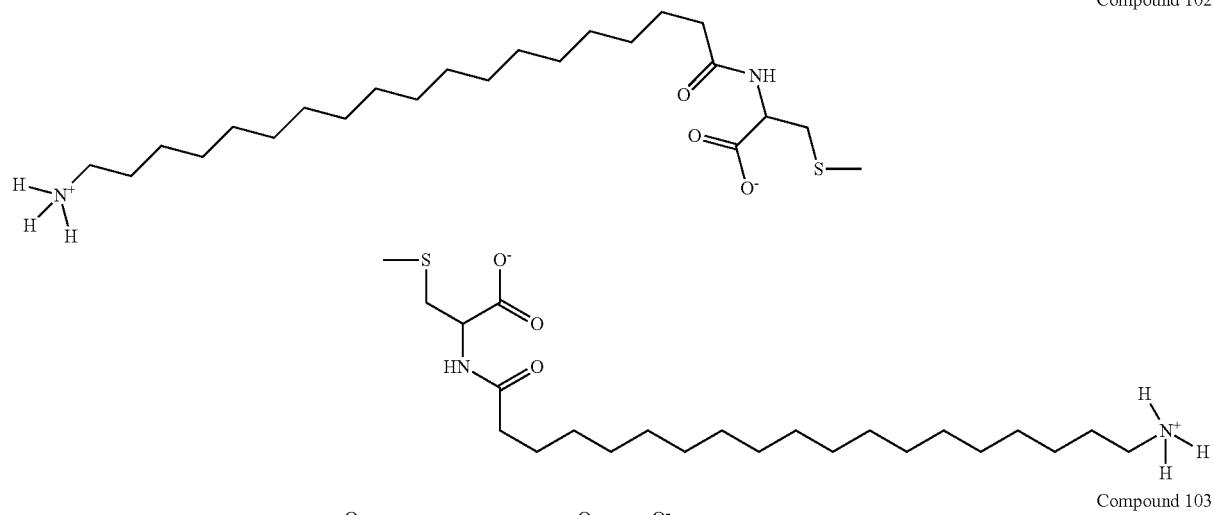
Compound 103
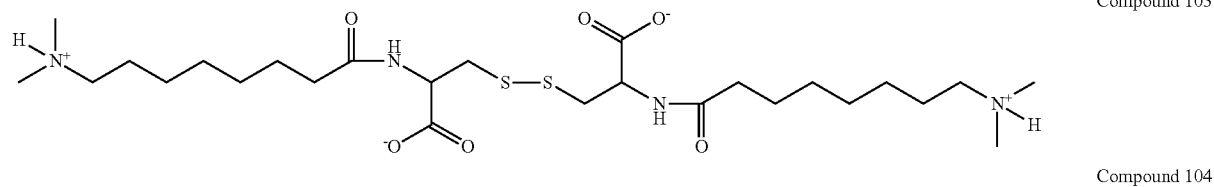
Compound 104
Compound 105
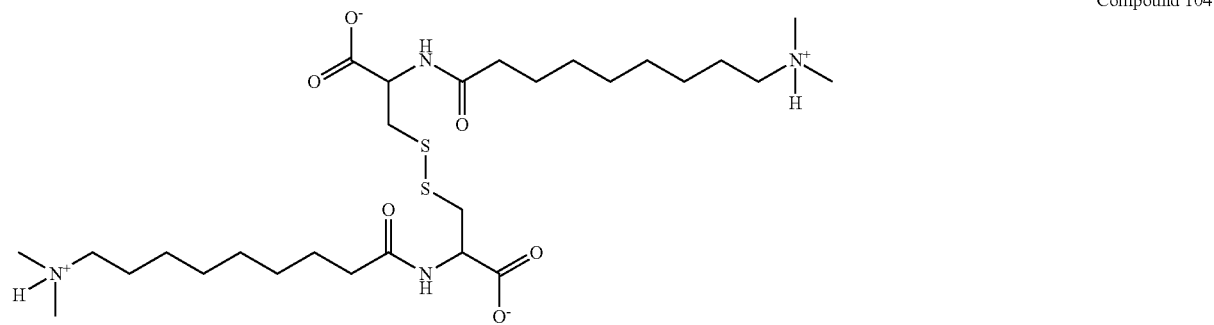

-continued
Compound 106
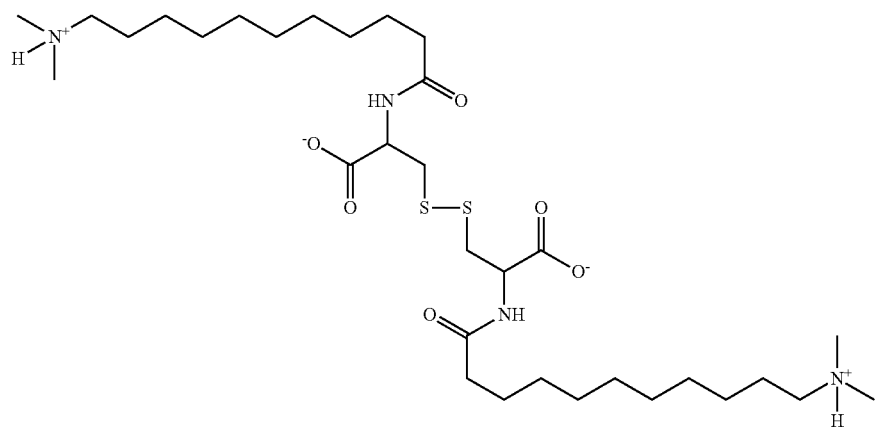
Compound 107
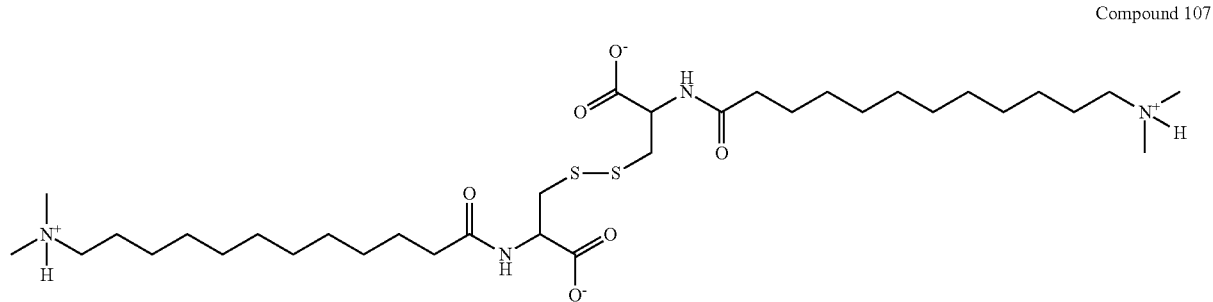
Compound 108
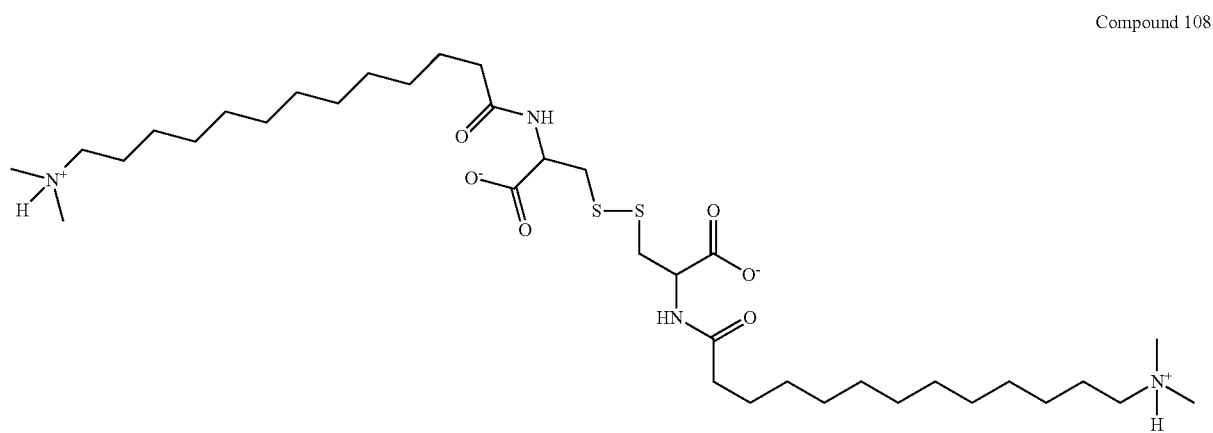
Compound 109
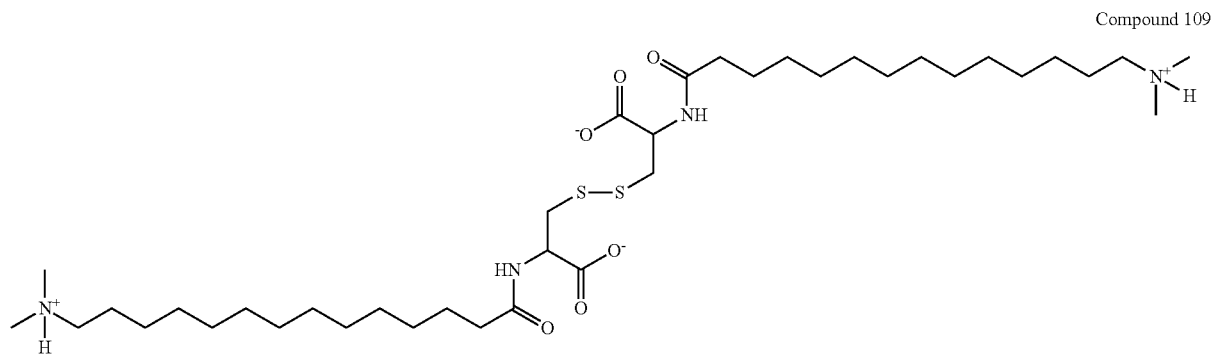

-continued
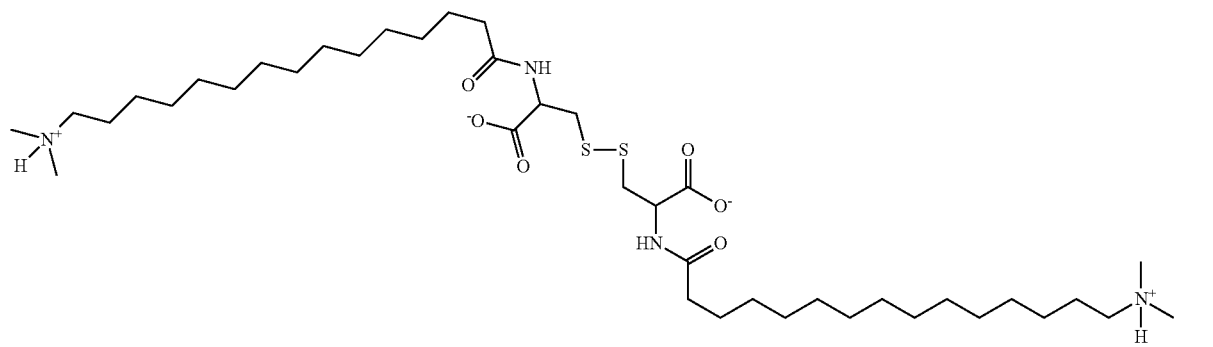
Compound 110
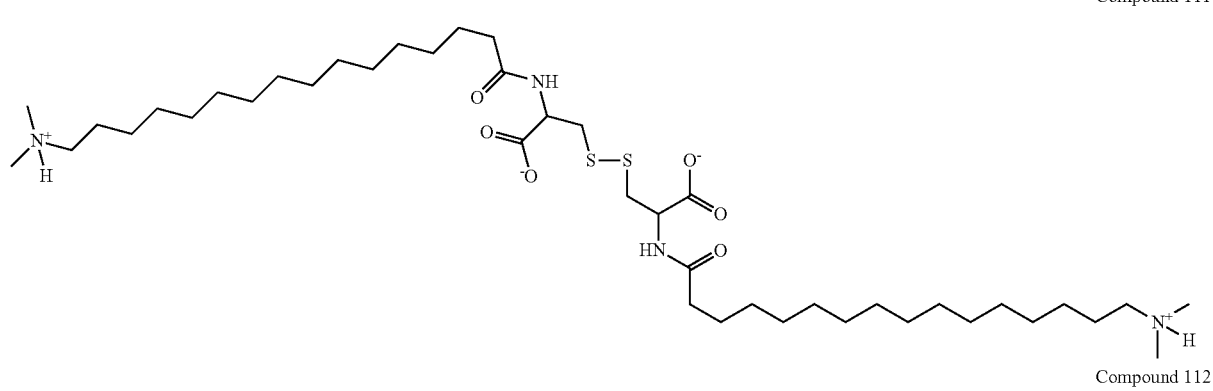
Compound 111
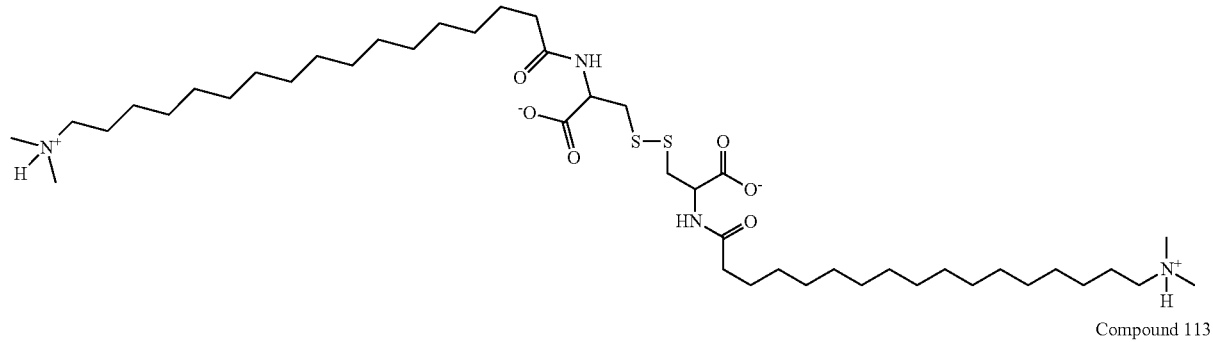
Compound 112
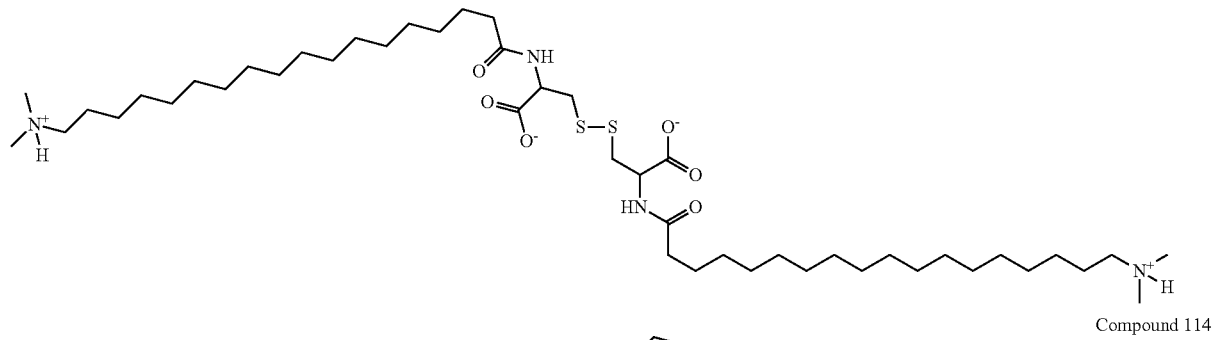
Compound 113
Compound 114
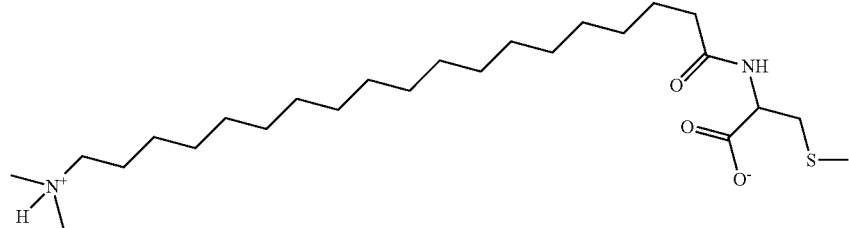

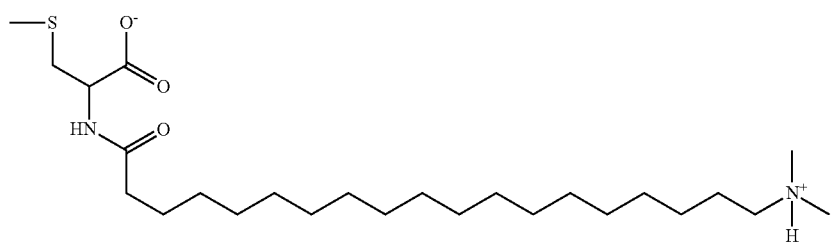
Compound 115
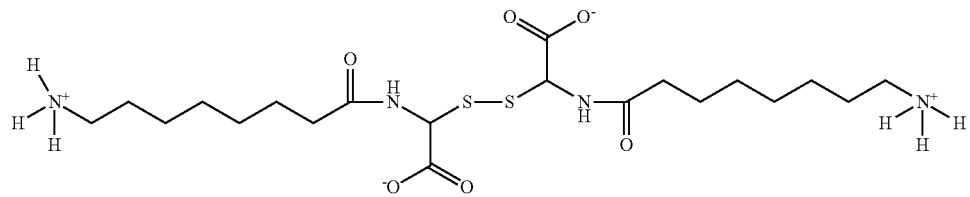
Compound 116
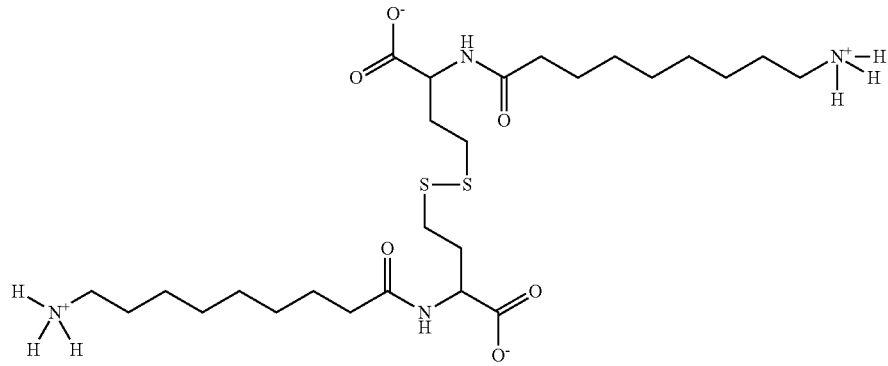
Compound 117
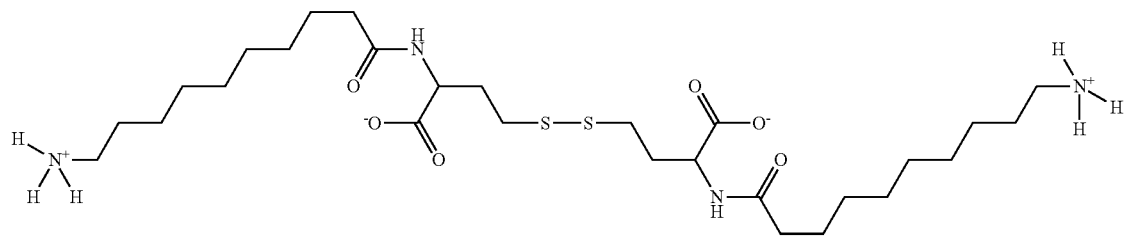
Compound 118
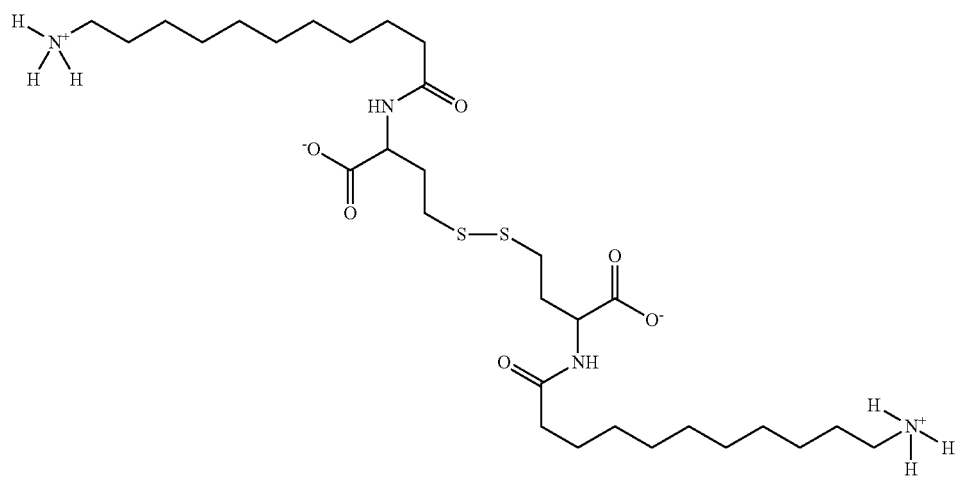

-continued
Compound 119
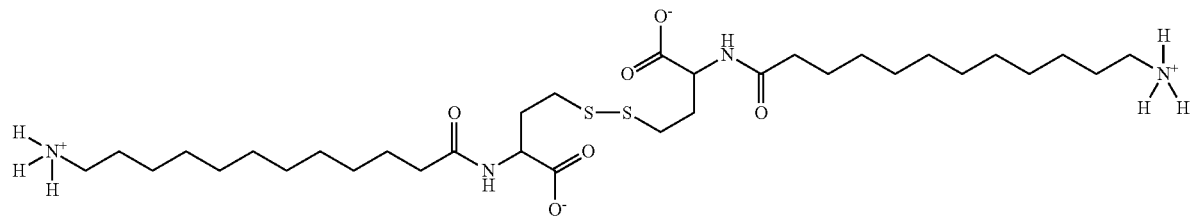
Compound 120
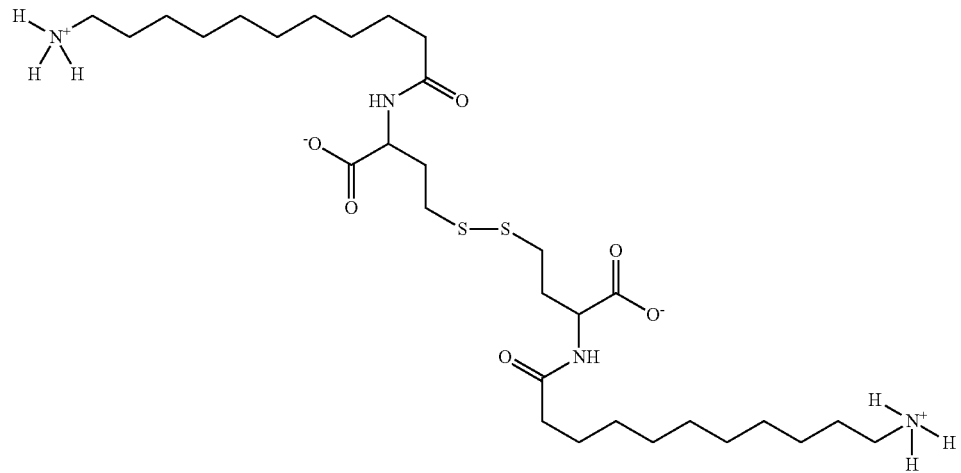
Compound 121
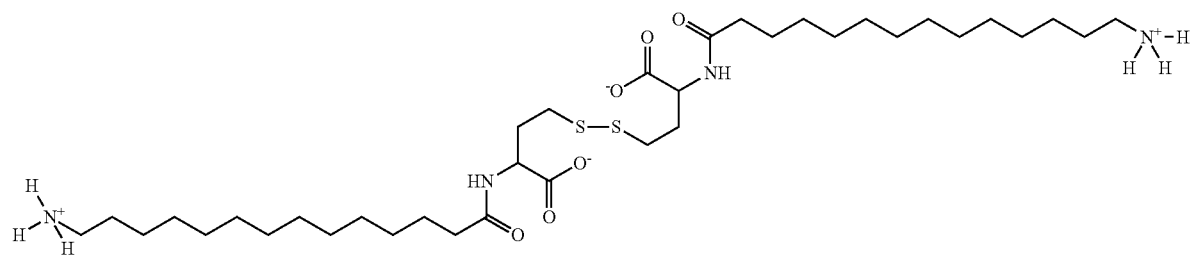
Compound 122
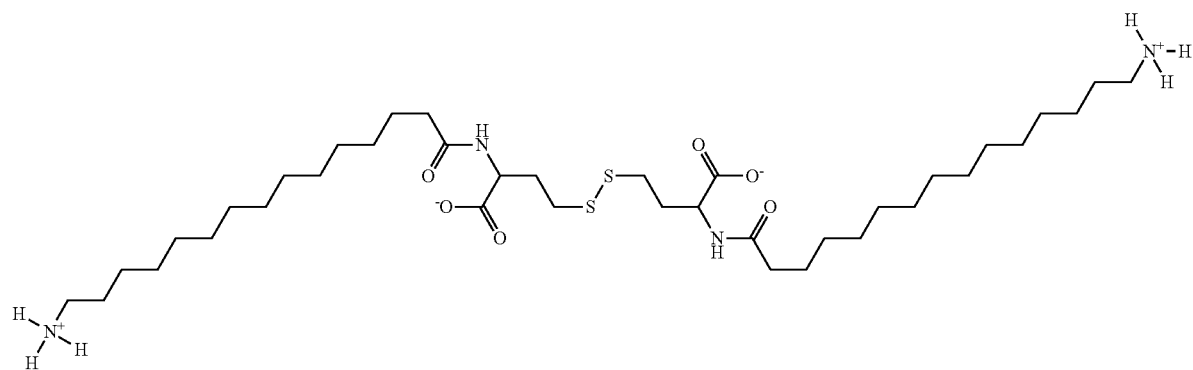

-continued
Compound 123
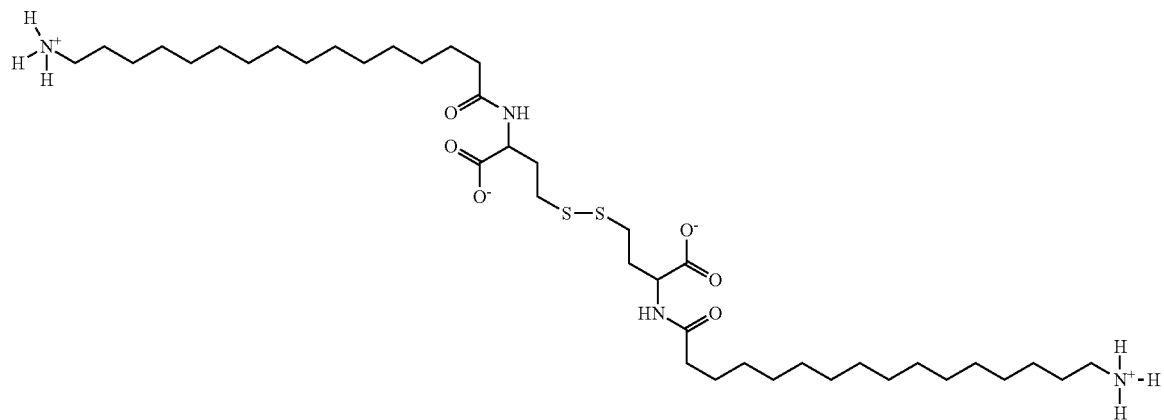
Compound 124
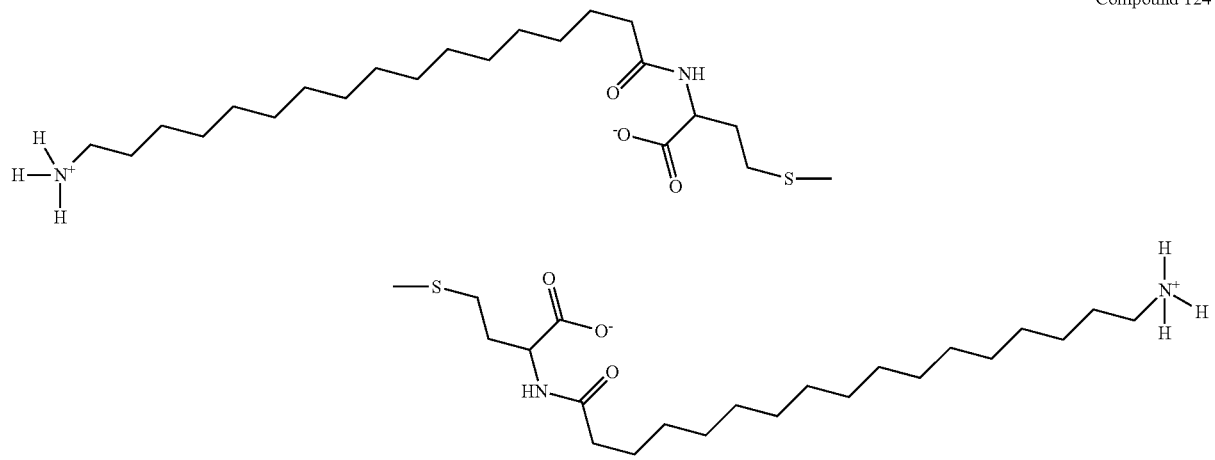
Compound 125
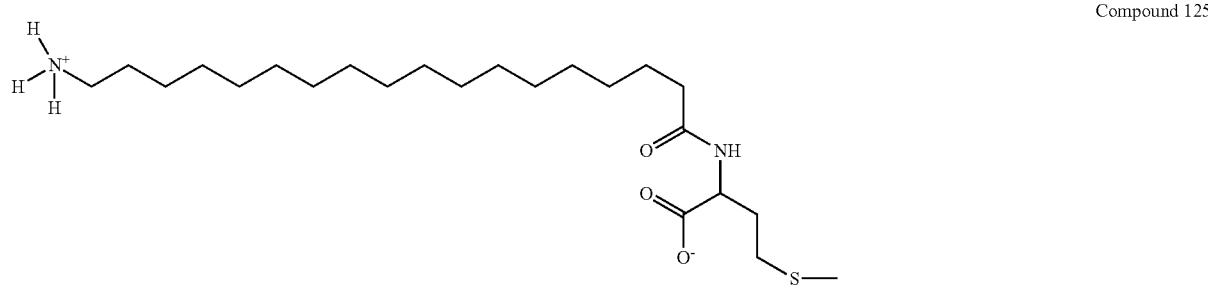
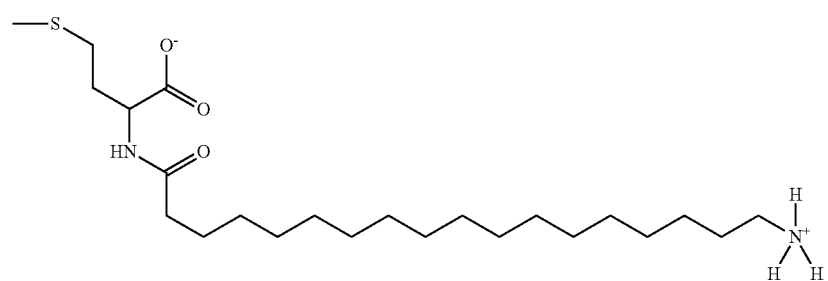

-continued
Compound 126
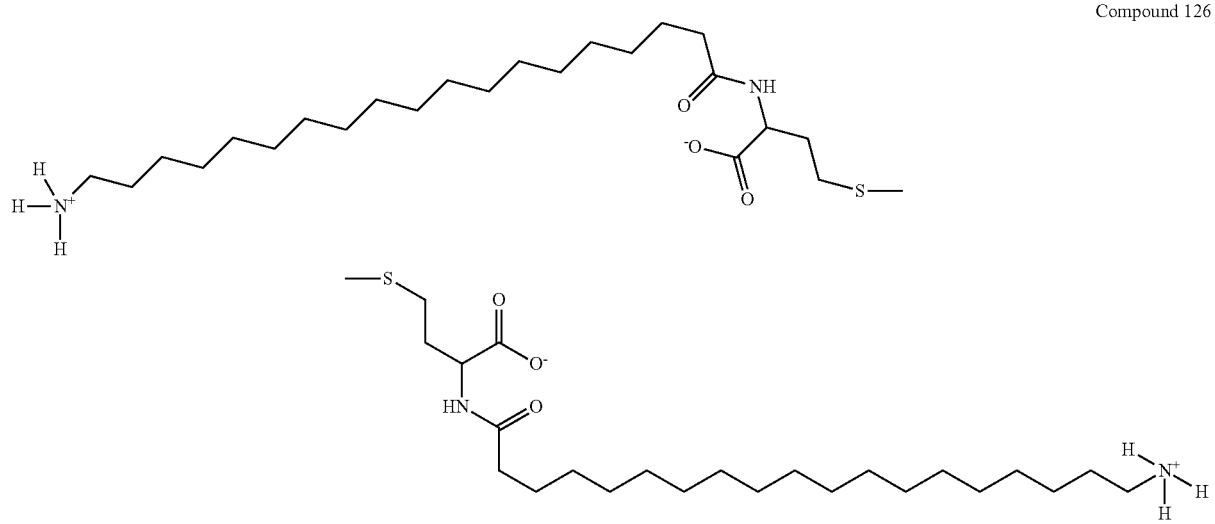
Compound 127
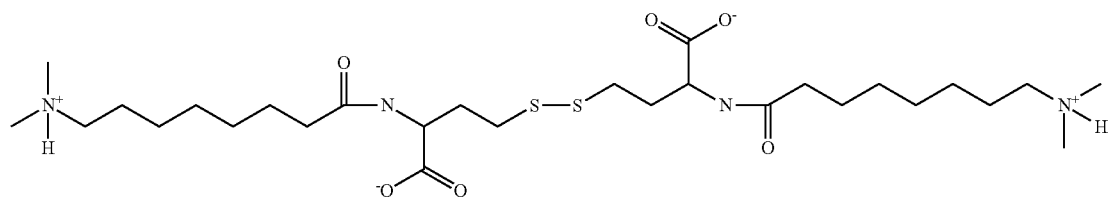
Compound 128
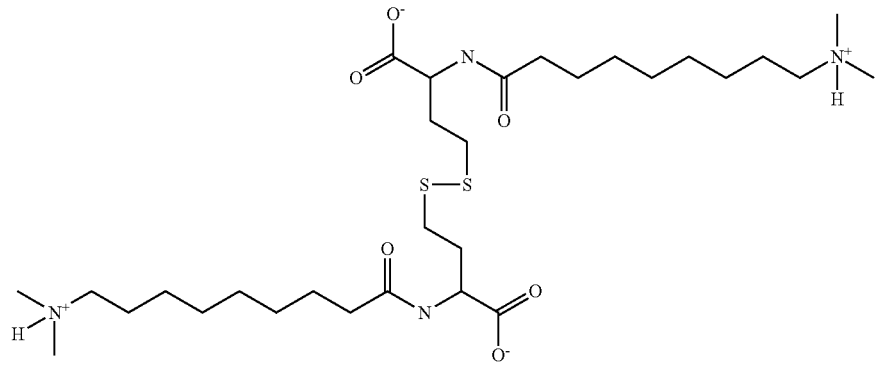
Compound 129
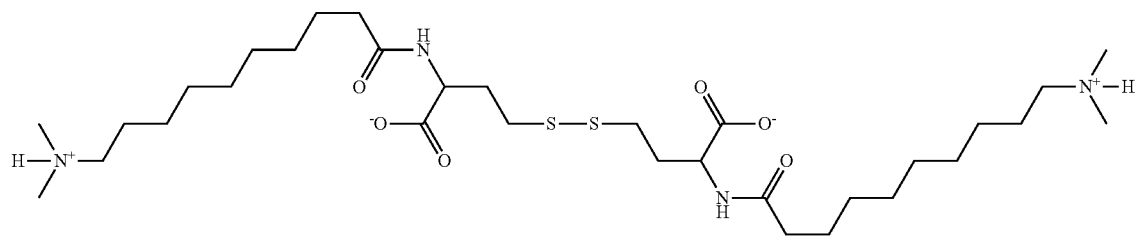

-continued
Compound 130
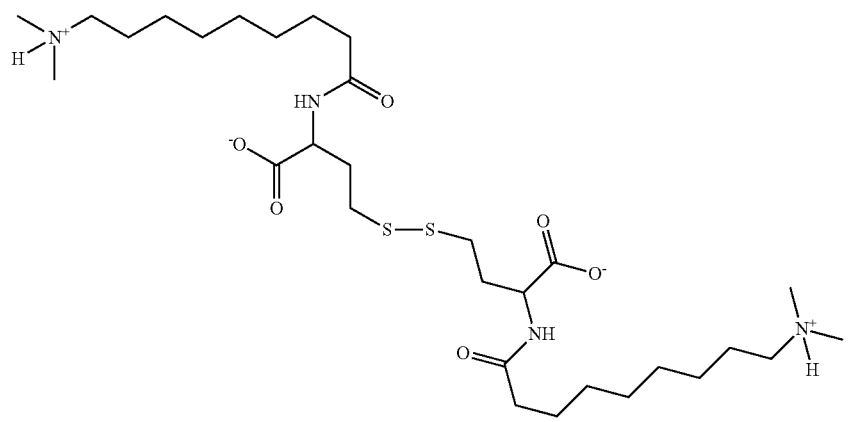
Compound 131
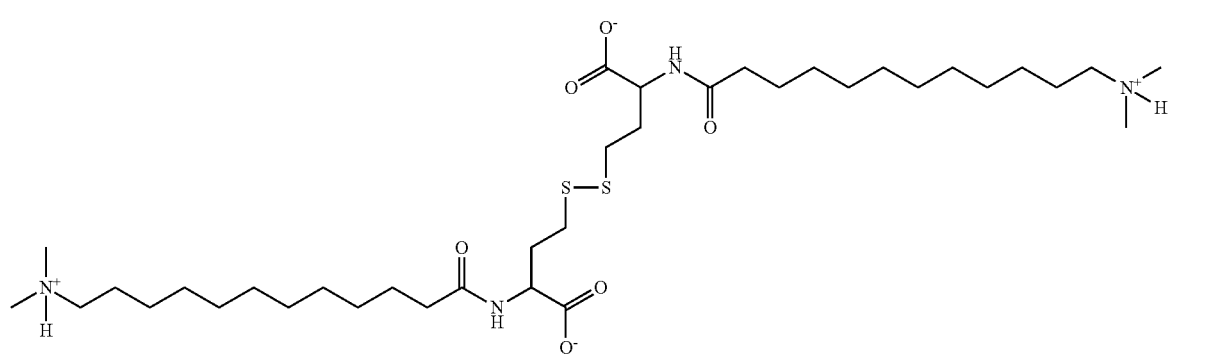
Compound 132
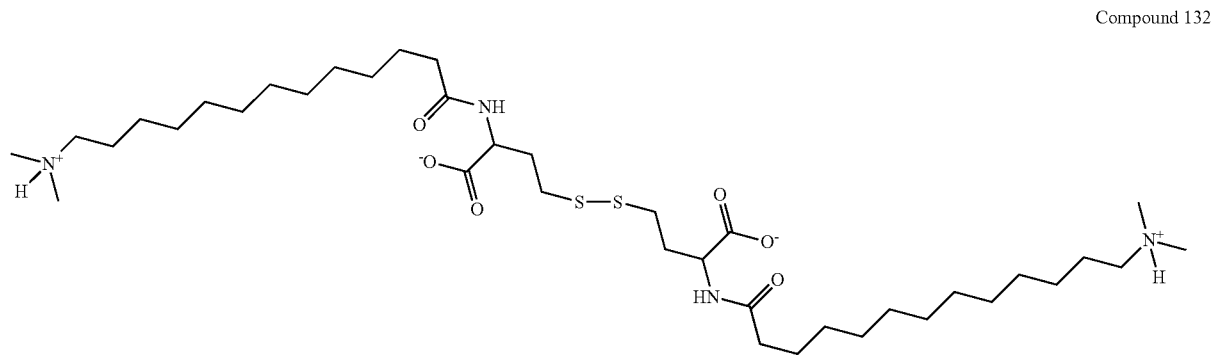
Compound 133
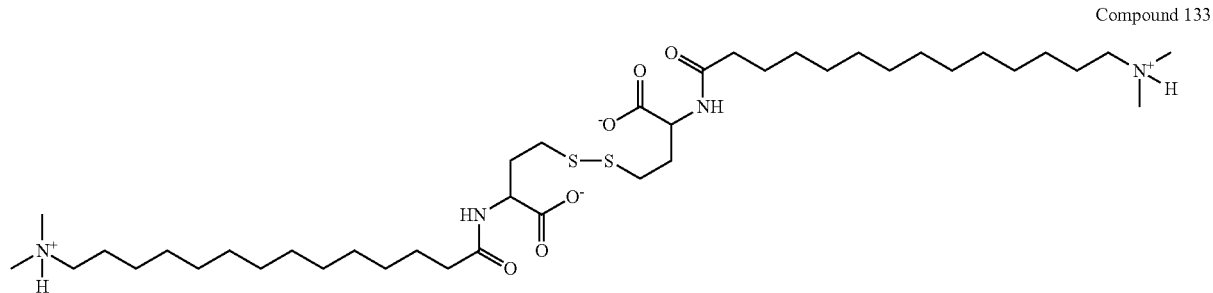

Compound 134
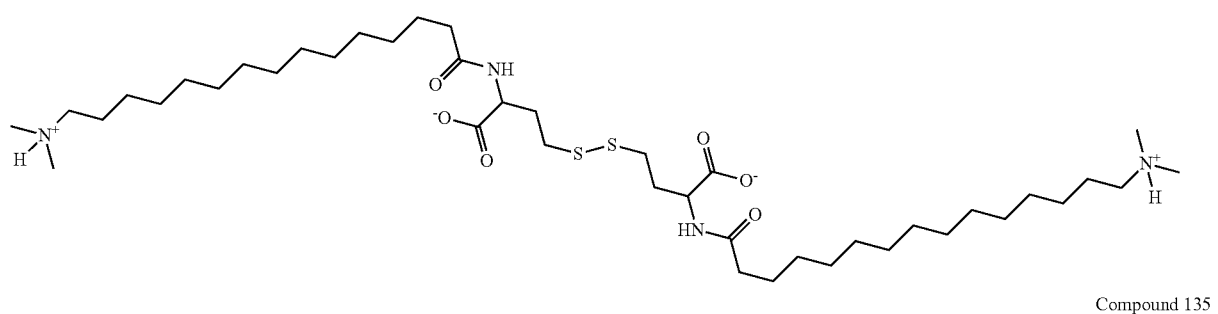
Compound 135
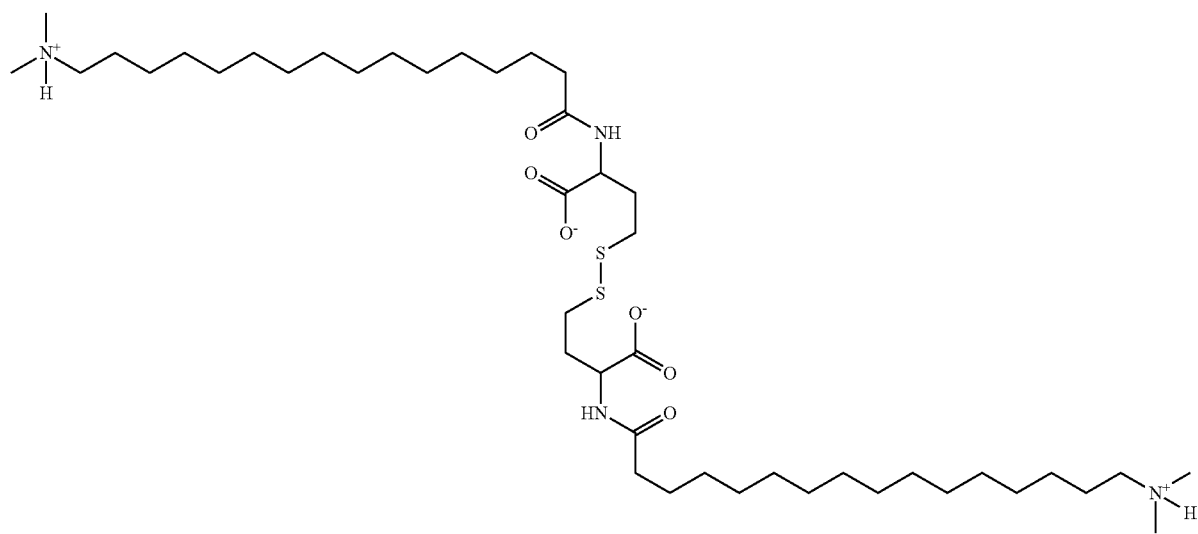
Compound 136
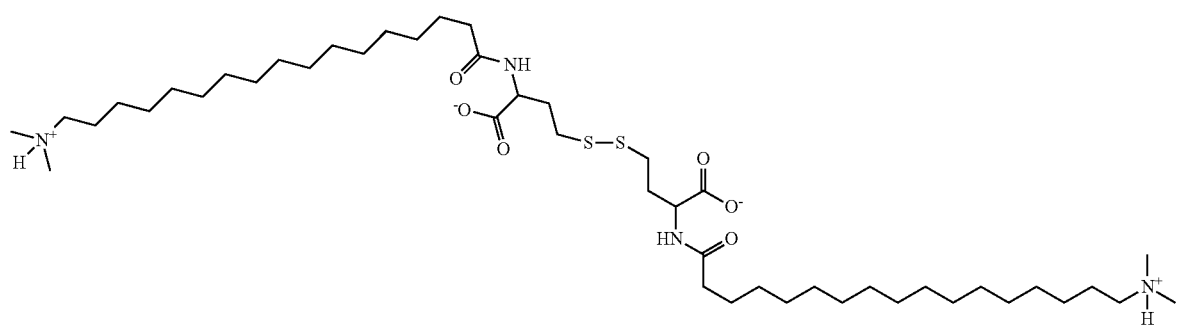
Compound 137
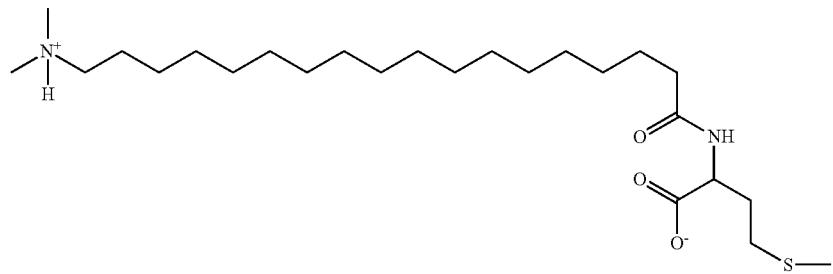

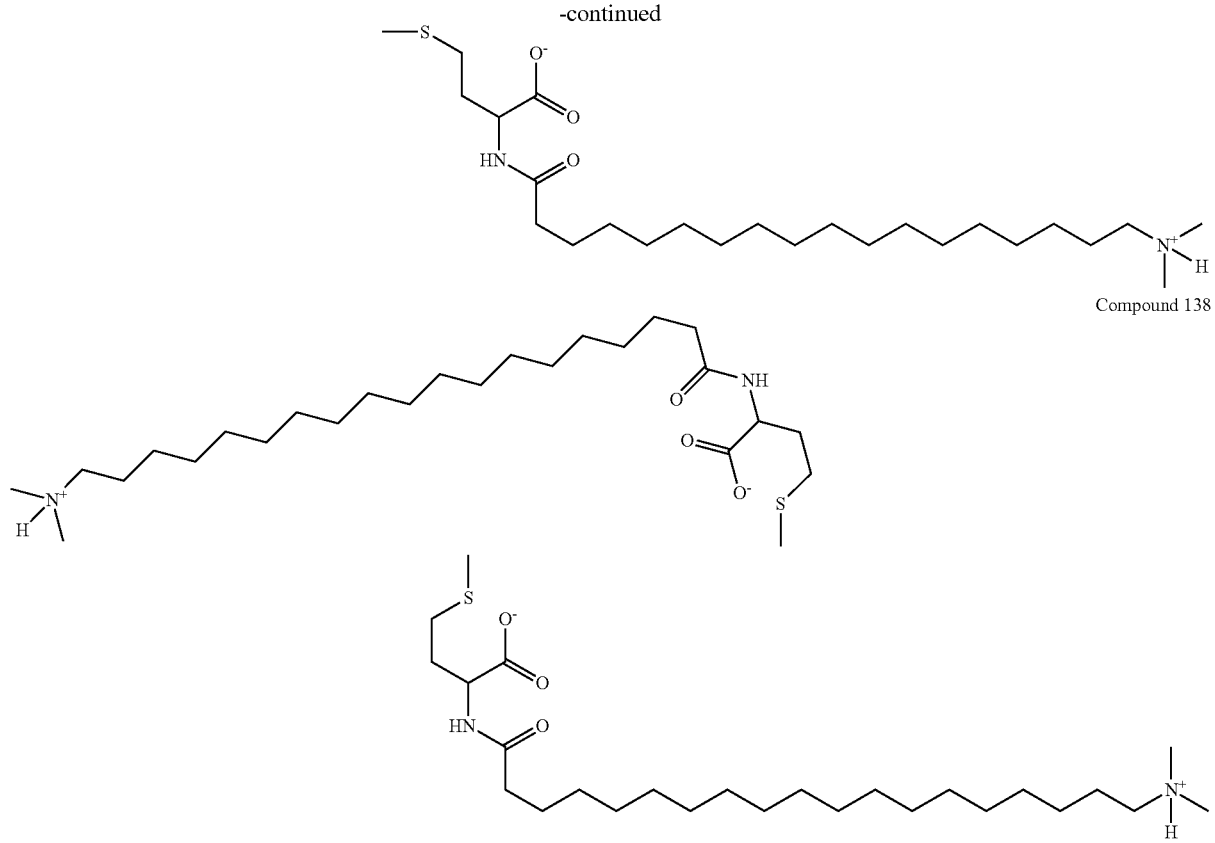

Compound 138 wherein the cosmetic composition modulates a hydrophobic nature of human keratin fibres and wherein the composition comprises one or more inorganic or organic thickeners.

2. The composition according to claim 1, characterized in that the total concentration of the said compounds ranges from 0.05 to 20% by weight relative to the total weight of the composition.

3. A process for treating keratin fibres comprising a step of applying the composition as defined in claim 1 or 2 to said fibres.

4. The process according to claim 3, characterized in that the composition contains one or more reducing agents.

5. The process according to claim 3 or 4, further comprising an additional step of applying an oxidizing agent, after the step of applying the composition.

6. A method of treating human keratin fibers, comprising applying the composition of claim 1 to a human keratin fiber, wherein the human keratin fiber is hair.

7. The method of claim 4, wherein applying the composition of claim 1 to hair modulates the hydrophobic nature of hair.

8. A multi-compartment device or kit, comprising:
a first compartment comprising a composition as defined in claim 1 or 2,
a second compartment comprising an oxidizing composition.

9. The cosmetic composition of claim 1, wherein the human keratin fibre is hair.

* * * * *